(12) United States Patent
Yang et al.

(10) Patent No.: US 12,029,112 B2
(45) Date of Patent: Jul. 2, 2024

(54) COMPOSITION FOR OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Yongtak Yang, Suwon-si (KR); Dong Min Kang, Suwon-si (KR); Hyung Sun Kim, Suwon-si (KR); Jinhyun Lui, Suwon-si (KR); Seungin Park, Suwon-si (KR); Jaejin Oh, Suwon-si (KR); Sung-Hyun Jung, Suwon-si (KR); Ho Kuk Jung, Suwon-si (KR); Youngkyoung Jo, Suwon-si (KR); Pyeongseok Cho, Suwon-si (KR); Dalho Huh, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 556 days.

(21) Appl. No.: 16/791,205

(22) Filed: Feb. 14, 2020

(65) Prior Publication Data

US 2020/0266358 A1 Aug. 20, 2020

(30) Foreign Application Priority Data

Feb. 15, 2019 (KR) .................. 10-2019-0018239

(51) Int. Cl.
| | |
|---|---|
| *H10K 85/60* | (2023.01) |
| *C07D 403/10* | (2006.01) |
| *C07D 403/14* | (2006.01) |
| *C07D 405/14* | (2006.01) |
| *C07D 487/04* | (2006.01) |
| *C07F 15/00* | (2006.01) |
| *C09K 11/06* | (2006.01) |

(Continued)

(52) U.S. Cl.
CPC ......... *H10K 85/654* (2023.02); *C07D 403/10* (2013.01); *C07D 403/14* (2013.01); *C07D 405/14* (2013.01); *C07D 487/04* (2013.01); *C07F 15/0033* (2013.01); *C07F 15/0086* (2013.01); *C09K 11/06* (2013.01); *H10K 85/342* (2023.02); *H10K 85/346* (2023.02); *H10K 85/6572* (2023.02); *H10K 85/6574* (2023.02); *C09K 2211/1029* (2013.01);

(Continued)

(58) Field of Classification Search
CPC . H01L 51/0067; C07D 403/14; C07D 405/14; C07D 487/04; C07D 209/82
See application file for complete search history.

(56) References Cited

U.S. PATENT DOCUMENTS

| | | | |
|---|---|---|---|
| 5,061,569 | A | 10/1991 | VanSlyke |
| 9,893,290 | B2 | 2/2018 | Min |

(Continued)

FOREIGN PATENT DOCUMENTS

| | | |
|---|---|---|
| CN | 104277824 A | 1/2015 |
| CN | 106537634 A | 3/2017 |

(Continued)

OTHER PUBLICATIONS

U.S. Appl. No. 16/788,552, filed Feb. 12, 2020.

(Continued)

*Primary Examiner* — Noble E Jarrell
(74) *Attorney, Agent, or Firm* — Lee IP Law, P.C.

(57) ABSTRACT

A composition for an organic optoelectronic device, an organic optoelectronic device, and a display device, the composition including a first compound; a second compound; and a third compound, the first compound, the second compound, and the third compound are different from each other, the first compound is represented by Chemical Formula I, the second compound is represented by Chemical Formula II or Chemical Formula III, and the third compound is represented by Chemical Formula II or Chemical Formula III,

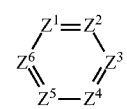

[Chemical Formula I]

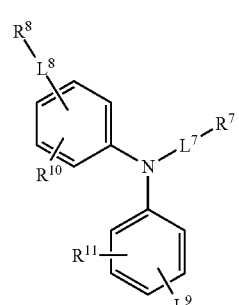

[Chemical Formula II]

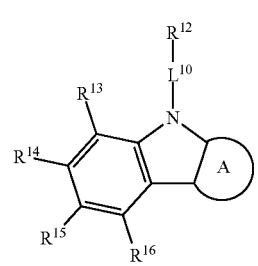

[Chemical Formula III]

22 Claims, 1 Drawing Sheet

(51) Int. Cl.
  *H10K 50/11*   (2023.01)
  *H10K 85/30*   (2023.01)
  *H10K 101/10*  (2023.01)

(52) U.S. Cl.
  CPC .............. *C09K 2211/1044* (2013.01); *C09K 2211/185* (2013.01); *H10K 50/11* (2023.02); *H10K 2101/10* (2023.02)

(56) References Cited

U.S. PATENT DOCUMENTS

| | | | |
|---|---|---|---|
| 2004/0086743 | A1 | 5/2004 | Brown et al. |
| 2015/0001488 | A1 | 1/2015 | Min |
| 2016/0181548 | A1* | 6/2016 | Parham ............... H10K 85/615 548/440 |
| 2017/0237017 | A1* | 8/2017 | Parham ............... H01L 51/0074 252/500 |
| 2017/0317293 | A1 | 11/2017 | Kim et al. |
| 2018/0019409 | A1 | 1/2018 | Ryu et al. |
| 2019/0189927 | A1 | 6/2019 | Lee et al. |

FOREIGN PATENT DOCUMENTS

| | | |
|---|---|---|
| CN | 106554771 A | 4/2017 |
| CN | 106929005 A | 7/2017 |
| CN | 107001930 A | 8/2017 |
| CN | 107623073 A | 1/2018 |
| JP | 05-009471 A | 1/1993 |
| JP | 07-126615 A | 5/1995 |
| JP | 10-095973 A | 4/1998 |
| JP | 4550160 B2 | 9/2010 |
| KR | 10-2016-0026661 A | 3/2016 |
| KR | 10-2016-0050614 A | 5/2016 |
| KR | 10-2017-0037277 A | 4/2017 |
| KR | 10-2018-0002351 A | 1/2018 |
| KR | 10-2018-0035196 A | 4/2018 |
| KR | 10-2018-0069475 A | 6/2018 |
| KR | 10-2018-0117919 A | 10/2018 |
| TW | 201903122 A | 1/2019 |
| WO | WO 95/09147 | 4/1995 |
| WO | WO 2016/068458 A1 | 5/2016 |
| WO | WO 2018/021737 A1 | 2/2018 |
| WO | WO 2018/110958 A1 | 6/2018 |
| WO | WO 2018/217067 A1 | 11/2018 |

OTHER PUBLICATIONS

Cas, reg No. 2231621-00-2, Jul. 25, 2018.
U.S. Office action received in copending U.S. Appl. No. 16/788,552, dated Dec. 13, 2022.
Chinese Search Report dated Oct. 28, 2022.
Zhenguo et al. "Synthesis and Properties of tert-Butylphenyl etc . . . " China Academic Journal, vol. 40, No. 6, Nov. 2010.
Chinese Office action and Search Report.
Chinese Notice of Allowance dated Dec. 29, 2023.
Chinese Office action dated May 9, 2023.
U.S. Office action received in copending related U.S. Appl. No. 16/788,552 dated May 22, 2023.

* cited by examiner

COMPOSITION FOR OPTOELECTRONIC DEVICE AND ORGANIC OPTOELECTRONIC DEVICE AND DISPLAY DEVICE

CROSS-REFERENCE TO RELATED APPLICATION

Korean Patent Application No. 10-2019-0018239, filed on Feb. 15, 2019, in the Korean Intellectual Property Office, and entitled: "Composition for Optoelectronic Device and Organic Optoelectronic Device and Display Device," is incorporated by reference herein in its entirety.

BACKGROUND

1. Field

Embodiments relate to a composition for an organic optoelectronic device, an organic optoelectronic device, and a display device.

2. Description of the Related Art

An organic optoelectronic device (e.g., organic optoelectronic diode) is a device that converts electrical energy into photoenergy, and vice versa.

An organic optoelectronic device may be classified as follows in accordance with its driving principles. One is a photoelectric device in which excitons are generated by photoenergy, separated into electrons and holes, and transferred to different electrodes to generate electrical energy. Another is a light emitting device where a voltage or a current is supplied to an electrode to generate photoenergy from electrical energy.

Examples of the organic optoelectronic device may include an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light, and the performance of organic light emitting diode is greatly influenced by the organic materials disposed between electrodes.

SUMMARY

The embodiments may be realized by providing a composition for an organic optoelectronic device, the composition including a first compound; a second compound; and a third compound, wherein the first compound, the second compound, and the third compound are different from each other, the first compound is represented by Chemical Formula I, the second compound is represented by Chemical Formula II or Chemical Formula III, and the third compound is represented by Chemical Formula II or Chemical Formula III:

[Chemical Formula I]

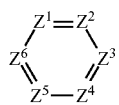

wherein, in Chemical Formula I, $Z^1$ is N or C-$L^1$-$R^1$, $Z^2$ is N or C-$L^2$-$R^2$, $Z^3$ is N or C-$L^3$-$R^3$, $Z^4$ is N or C-$L^4$-$R^4$, $Z^5$ is N or C-$L^5$-$R^5$, $Z^6$ is N or C-$L^6$-$R^6$, at least two of $Z^1$ to $Z^6$ are N, $L^1$ to $L^6$ are independently a single bond, a substituted or unsubstituted C6 to C20 arylene group, a substituted or unsubstituted C2 to C20 heterocyclic group, or a combination thereof, $R^1$ to $R^6$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^1$ to $R^6$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, and when $R^1$ to $R^6$ are separate, at least one of $R^1$ to $R^6$ is a substituted or unsubstituted C2 to C30 heterocyclic group;

[Chemical Formula II]

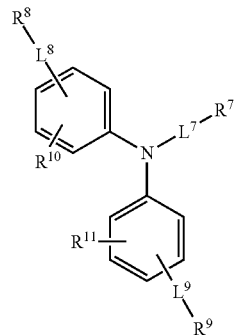

wherein, in Chemical Formula II, $L^7$ to $L^9$ are independently a single bond, a substituted or unsubstituted C6 to C20 arylene group, a substituted or unsubstituted C2 to C20 heterocyclic group, or a combination thereof, $R^7$ to $R^{11}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^8$ to $R^{11}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring;

[Chemical Formula III]

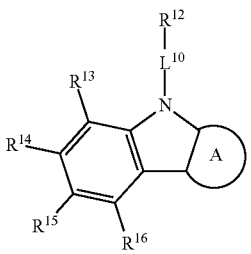

wherein, in Chemical Formula III, $L^{10}$ is a single bond, a substituted or unsubstituted C6 to C20 arylene group, a substituted or unsubstituted C2 to C20 heterocyclic group, or a combination thereof, $R^{12}$ to $R^{16}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{12}$ to $R^{16}$ are separate or adjacent groups thereof are linked with each other to form a substituted or unsubstituted aromatic monocyclic or polycyclic ring, and A is a moiety represented by one of Chemical Formulae A-1 to A-7,

[Chemical Formula A-1]

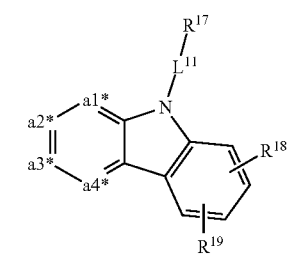

[Chemical Formula A-2]

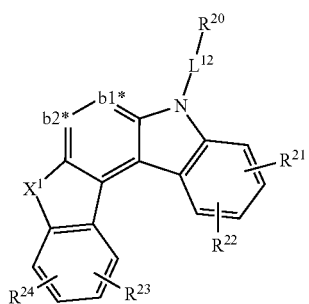

[Chemical Formula A-3]

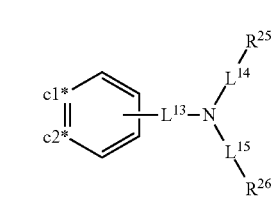

[Chemical Formula A-4]

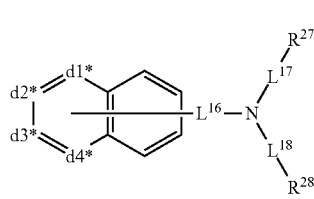

[Chemical Formula A-5]

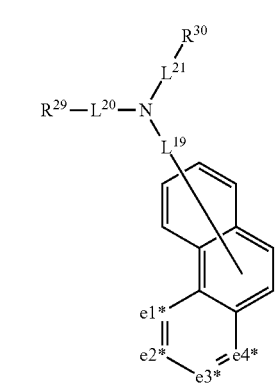

[Chemical Formula A-6]

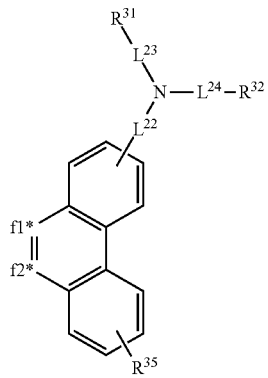

[Chemical Formula A-7]

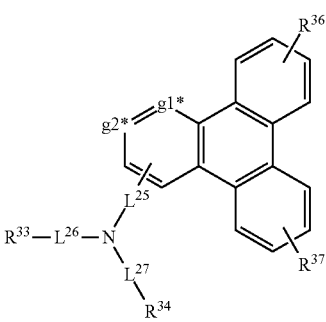

wherein, in Chemical Formulae A-1 to A-7, $X^1$ is O, S, or $NR^a$, a1* to a4* are independently a linking C or $C\text{-}L^a\text{-}R^b$, adjacent two of a1* to a4* are the linking C and the remaining two are $C\text{-}L^a\text{-}R^b$, d1* to d4* are independently a linking C or $C\text{-}L^b\text{-}R^c$, adjacent two of d1* to d4* are the linking C and the remaining two are $C\text{-}L^b\text{-}R^c$, e1* to e4* are independently a linking C or $C\text{-}L^c\text{-}R^d$, adjacent two of e1* to e4* are the linking C and the remaining two are $C\text{-}L^c\text{-}R^d$, b1* and b2*, c1* and c2*, f1* and f2*, and g1* and *g2 are each a linking C, $L^a$, $L^b$, $L^c$, and $L^{11}$ to $L^{27}$ are independently a single bond, a substituted or unsubstituted C6 to C20 arylene group, a substituted or unsubstituted C2 to C20 heterocyclic group, or a combination thereof, and $R^a$, $R^b$, $R^c$, $R^d$, and $R^{17}$ to $R^{37}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

The embodiments may be realized by providing an organic optoelectronic device including an anode and a cathode facing each other, and at least one organic layer between the anode and the cathode, wherein the organic layer includes the composition according to an embodiment.

The embodiments may be realized by providing a display device comprising the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
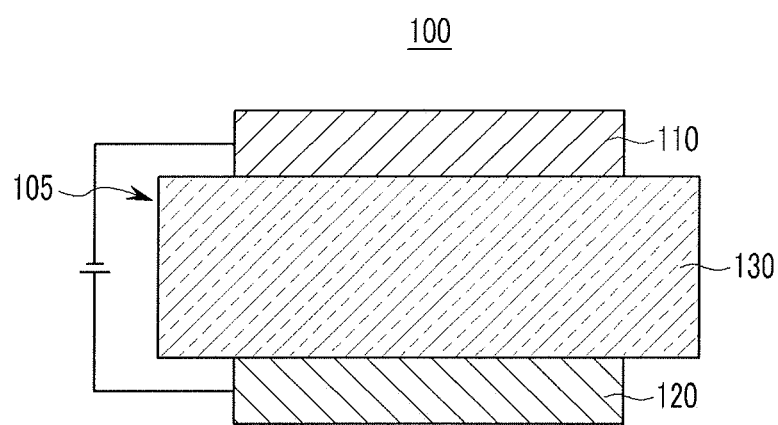
FIGS. 1 and 2 illustrate cross-sectional views of organic light emitting diodes according to embodiments.

Example embodiments will now be described more fully hereinafter with reference to the accompanying drawings;

however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a cyano group, a C1 to C30 alkyl group, a C1 to C10 alkylsilyl group, a C6 to C30 arylamine group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples, "substituted" refers to replacement of at least one hydrogen of a substituent or a compound by deuterium, a cyano group, a C1 to C20 alkyl group, a C6 to C30 arylamine group, a C6 to C30 aryl group, or a C2 to C30 heteroaryl group. In addition, in specific examples, "substituted" refers to replacement of at least one hydrogen of a substituent or a compound by deuterium, a cyano group, a C1 to C5 alkyl group, a C6 to C20 arylamine group, a C6 to C18 aryl group, a dibenzofuranyl group, a dibenzothiophenyl group, a carbazolyl group, or a pyridinyl group. In addition, in specific examples, "substituted" refers to replacement of at least one hydrogen of a substituent or a compound by deuterium, a cyano group, a methyl group, an ethyl group, a propyl group, a butyl group, a C6 to C20 arylamine group, a phenyl group, a biphenyl group, a terphenyl group, a naphthyl group, a triphenyl group, a fluorenyl group, a dibenzofuranyl group, a dibenzothiophenyl group, a carbazolyl group, or a pyridinyl group.

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety. All the elements of the hydrocarbon aromatic moiety have p-orbitals which form conjugation, for example a phenyl group, a naphthyl group, and the like; two or more hydrocarbon aromatic moieties may be linked by a sigma bond, for example a biphenyl group, a terphenyl group, a quaterphenyl group, and the like; or two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, or a combination thereof.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

The composition for the organic optoelectronic device according to an embodiment includes three types of compounds, e.g., a first compound having electron characteristics, and a second compound and a third compound having hole characteristics.

The first compound which has electron characteristics may include a nitrogen-containing hexagon (six-membered) ring, and may be represented by Chemical Formula I.

[Chemical Formula I]

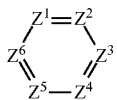

In Chemical Formula I,
$Z^1$ may be, e.g., N or C-$L^1$-$R^1$,
$Z^2$ may be, e.g., N or C-$L^2$-$R^2$,
$Z^3$ may be, e.g., N or C-$L^3$-$R^3$,
$Z^4$ may be, e.g., N or C-$L^4$-$R^4$,
$Z^5$ may be, e.g., N or C-$L^5$-$R^5$,
$Z^6$ may be, e.g., N or C-$L^6$-$R^6$,
at least two of $Z^1$ to $Z^6$ may be, e.g., N,
$L^1$ to $L^6$ may be, e.g., independently a single bond, a substituted or unsubstituted C6 to C20 arylene group, a substituted or unsubstituted C2 to C20 heterocyclic group, or a combination thereof,
$R^1$ to $R^6$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof,
$R^1$ to $R^6$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, and
when $R^1$ to $R^6$ are separate, at least one of $R^1$ to $R^6$ is a substituted or unsubstituted C2 to C30 heterocyclic group. As used herein, the term "or" is not an exclusive term, e.g., "A or B" would include A, B, or A and B.

Chemical Formula I may be represented, e.g., by at least one of Chemical Formula I-1 to Chemical Formula I-4 (e.g., according to whether adjacent groups of the nitrogen-containing six-membered ring are further fused).

For example, $R^1$ to $R^6$ may be separate, and the compound may be represented by Chemical Formula I-1. In an implementation, at least one of $R^2$, $R^4$, and $R^6$ may be, e.g., a substituted or unsubstituted C2 to C30 heterocyclic group.

In an implementation, $R^2$ and $R^3$ may be linked with each other to form a substituted or unsubstituted aromatic monocyclic or polycyclic ring, and the first compound may be represented by Chemical Formula I-2 or Chemical Formula I-3.

In an implementation, $R^2$ and $R^3$ may be linked together to form a substituted or unsubstituted heteroaromatic polycyclic ring, and the first compound may be represented by Chemical Formula I-4.

[Chemical Formula I-1]

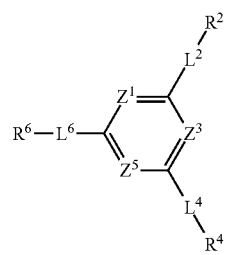

[Chemical Formula I-2]

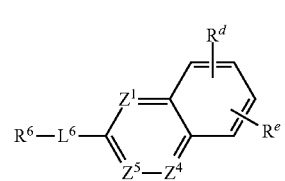

[Chemical Formula I-3]

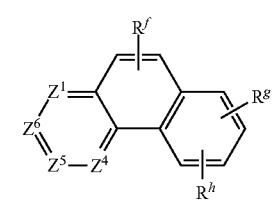

[Chemical Formula I-4]

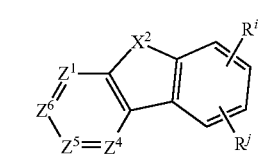

In Chemical Formula I-1 to Chemical Formula I-4, $Z^1$, $Z^3$ to $Z^6$, $L^2$, $L^4$, $L^6$, $R^2$, $R^4$, and $R^6$ may be the same as described above,
$X^2$ may be, e.g., O or S,
at least two of $Z^1$, $Z^3$, and $Z^5$ of Chemical Formula I-1 may be, e.g., N,
at least two of $Z^1$, $Z^4$, and $Z^5$ of Chemical Formula I-2 may be, e.g., N,
at least two of $Z^1$, and $Z^4$ to $Z^6$ of Chemical Formula I-3 and Chemical Formula I-4 may be, e.g., N, and
$R^d$ to $R^j$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In an implementation, the first compound may be represented by Chemical Formula I-1.

In an implementation, $Z^1$, $Z^3$, and $Z^5$ of Chemical Formula I-1 may independently be, e.g., N or CH. In an implementation, at least two of $Z^1$, $Z^3$, and $Z^5$ may be N.

For example, $Z^1$, $Z^3$, and $Z^5$ may independently be N.

For example, $Z^1$ and $Z^3$ may be N and $Z^5$ may be CH.

$L^2$, $L^4$, and $L^6$ of Chemical Formula I-1 may independently be, e.g., a single bond, a phenylene group, a biphenylene group, a carbazolylene group, a dibenzofuranylene group, a dibenzothiophenylene group, or a pyridinylene group.

For example, $L^2$, $L^4$, and $L^6$ may independently be, e.g., a single bond, a m-phenylene group, or a p-phenylene group.

$R^2$, $R^4$, and $R^6$ of Chemical Formula I-1 may independently be, e.g., a substituted or unsubstituted C6 to C30 aryl group or a substituted or unsubstituted C2 to C30 heterocyclic group provided that at least one of $R^2$, $R^4$, and $R^6$ may be a substituted or unsubstituted C2 to C30 heterocyclic group.

In an implementation, $R^2$, $R^4$, and $R^6$ may independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted carbazolyl group, a substituted or unsubstituted indolocarbazolyl group, a substituted or unsubstituted dibenzofuranyl group, a substituted or unsubstituted dibenzothiophenyl group, a substituted or unsubstituted fused carbazolyl group, a substituted or unsubstituted fused dibenzofuranyl group, a substituted or unsubstituted fused dibenzothiophenyl group, a substituted or unsubstituted fused indolocarbazolyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group or a substituted or unsubstituted benzoquinazolinyl group provided that at least one of $R^2$, $R^4$, and $R^6$ may be a substituted or unsubstituted carbazolyl group, a substituted or unsubstituted indolocarbazolyl group, a substituted or unsubstituted dibenzofuranyl group, a substituted or unsubstituted dibenzothiophenyl group, a substituted or unsubstituted fused carbazolyl group, a substituted or unsubstituted fused dibenzofuranyl group, a substituted or unsubstituted fused dibenzothiophenyl group, a substituted or unsubstituted fused indolocarbazolyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group, or a substituted or unsubstituted benzoquinazolinyl group.

For example, $R^2$, $R^4$, and $R^6$ may independently be a substituted or unsubstituted phenyl group, a substituted or unsubstituted biphenyl group, a substituted or unsubstituted terphenyl group, a substituted or unsubstituted carbazolyl group, a substituted or unsubstituted indolocarbazolyl group, a substituted or unsubstituted dibenzofuranyl group, a substituted or unsubstituted dibenzothiophenyl group, or a combination thereof, provided that at least one of $R^2$, $R^4$, and $R^6$ may be a substituted or unsubstituted carbazolyl group, a substituted or unsubstituted indolocarbazolyl group, a substituted or unsubstituted dibenzofuranyl group, or a substituted or unsubstituted dibenzothiophenyl group.

In an implementation, when $R^2$, $R^4$, and $R^6$ are substituted, the substituent may be, e.g., a cyano group, a phenyl group, a biphenyl group, a dibenzofuranyl group, a dibenzothiophenyl group, a carbazolyl group, a C6 to C20 arylamine group, or a combination thereof.

In an implementation, Chemical Formula I-1 may be, e.g., represented by one of Chemical Formula I-1A to Chemical Formula I-1C.

[Chemical Formula I-1A]

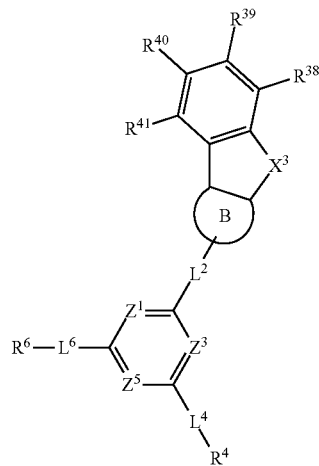

[Chemical Formula I-1B]

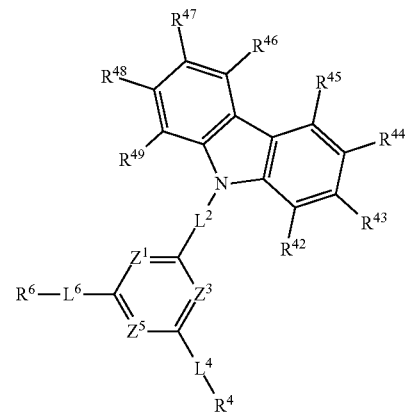

[Chemical Formula I-1C]

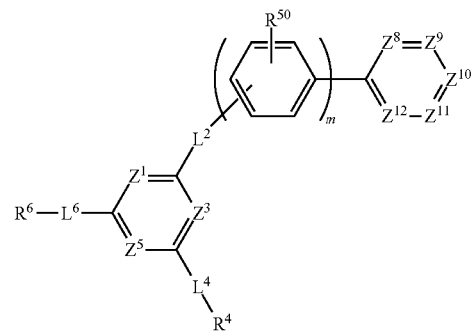

In Chemical Formula I-1A to Chemical Formula I-1C,
$Z^1$, $Z^3$, $Z^5$, $L^2$, $L^4$, $L^6$, $R^4$, and $R^6$ may be the same as described above,
$X^3$ may be, e.g., O, S, or $NR^k$,
$Z^8$ may be, e.g., N or C-$L^{28}$-$R^{51}$,
$Z^9$ may be, e.g., N or C-$L^{29}$-$R^{52}$,
$Z^{10}$ may be, e.g., N or C-$L^{30}$-$R^{53}$,
$Z^{11}$ may be, e.g., N or C-$L^{31}$-$R^{54}$,
$Z^{12}$ may be, e.g., N or C-$L^{32}$-$R^{55}$, and
at least one of $Z^8$ to $Z^{12}$ may be, e.g., N,
$L^{28}$ to $L^{33}$ may be, e.g., independently a single bond, a substituted or unsubstituted C6 to C20 arylene group, a substituted or unsubstituted C2 to C20 heterocyclic group, or a combination thereof, $R^k$ may be, e.g., a substituted or unsubstituted C6 to C30 aryl group, a substituted or unsubstituted C2 to C30 heterocyclic group, or a combination thereof, $R^{38}$ to $R^{55}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{38}$ to $R^{41}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{42}$ to $R^{45}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{46}$ to $R^{49}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{51}$ to $R^{55}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, m may be, e.g., an integer of 0 to 3, and B may be, e.g., a moiety represented by Chemical Formula B-1 or B-2.

[Chemical Formula B-1]

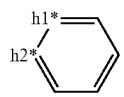

[Chemical Formula B-2]

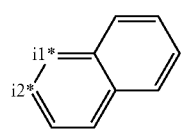

In Chemical Formula B-1 and Chemical Formula B-2, h1* and h2* and i1* and i2* may each be a linking carbon ("linking C"). As used herein, the term "linking C" refers to a shared carbon at which fused rings are linked.

In an implementation, $L^{28}$ to $L^{33}$ may independently be, e.g., a single bond, a phenylene group, or a biphenylene group, $R^k$ may be, e.g., a C6 to C12 aryl group, and m may be, e.g., an integer of 0 to 2.

In an implementation, at least one of $R^2$, $R^4$, and $R^6$ may be, e.g., a substituted or unsubstituted carbazolyl group, a substituted or unsubstituted dibenzofuranyl group, a substituted or unsubstituted dibenzothiophenyl group, a substituted or unsubstituted fused dibenzofuranyl group, or a substituted or unsubstituted fused dibenzothiophenyl group.

In an implementation, Chemical Formula I-1A may be, e.g., represented by one of Chemical Formulae I-1A-1 to I-1A-6.

For example, $R^{38}$ to $R^{41}$ may be separate, and the first compound may be represented by one of Chemical Formulae I-1A-1 to I-1A-3.

In an implementation, adjacent groups of $R^{38}$ to $R^{41}$ may be linked with each other to form a substituted or unsubstituted aliphatic, aromatic, or heteroaromatic monocyclic ring or a substituted or unsubstituted aliphatic, aromatic, or heteroaromatic polycyclic ring, and the first compound may be represented by one of Chemical Formulae I-1A-4 to I-1A-6.

[Chemical Formula I-1A-1]

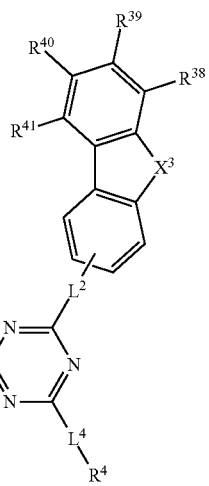

[Chemical Formula I-1A-2]

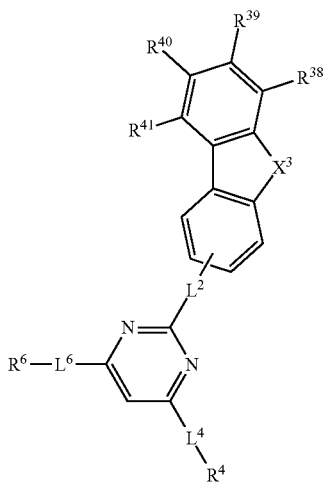

[Chemical Formula I-1A-3]

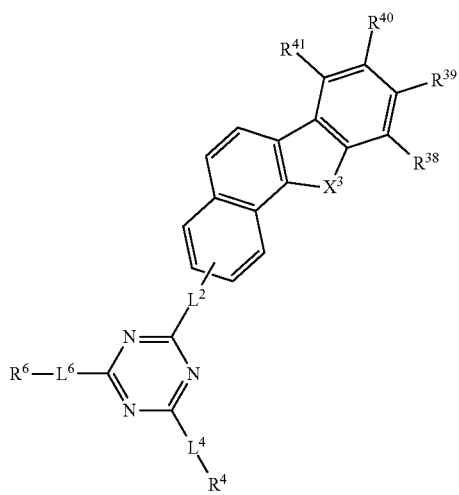

[Chemical Formula I-1A-4]

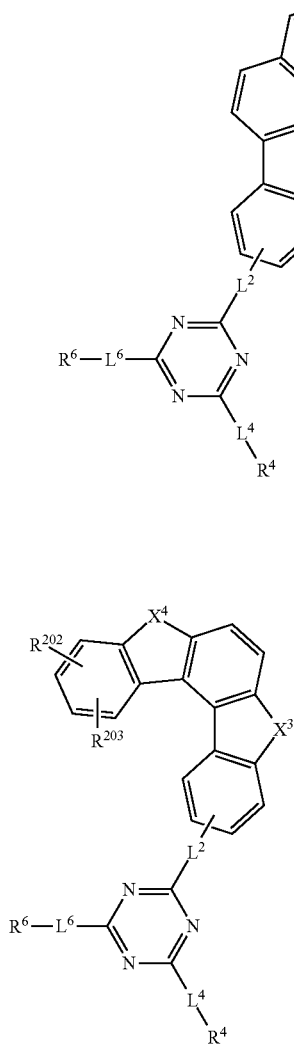

[Chemical Formula I-1A-5]

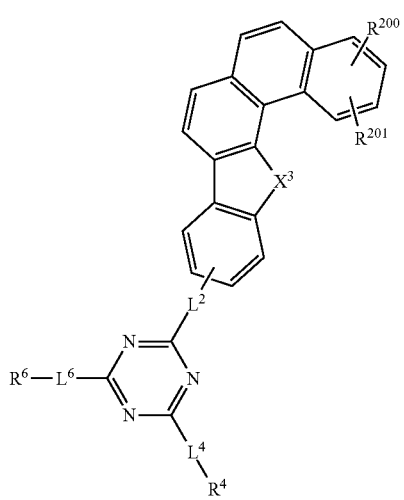

[Chemical Formula I-1A-6]

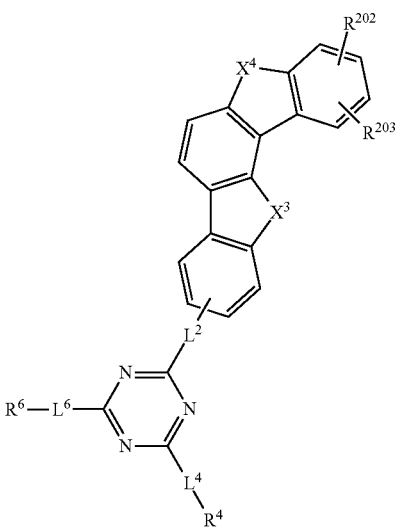

In Chemical Formulae I-1A-1 to I-1A-6, $X^3$, $L^2$, $L^4$, $L^6$, $R^k$, $R^4$, $R^6$, and $R^{38}$ to $R^{41}$ may be the same as described above, $X^4$ may be, e.g., O, S, or $NR^l$, $R^l$ may be, e.g., a substituted or unsubstituted C6 to C30 aryl group, a substituted or unsubstituted C2 to C30 heterocyclic group, or a combination thereof, and $R^{200}$ to $R^{203}$ be, e.g., independently hydrogen, deuterium, a substituted or unsubstituted C1 to C10 alkyl group, a substituted or unsubstituted C6 to C20 aryl group, a halogen, a cyano group, or a combination thereof.

In a more specific embodiment, $R^l$ may be, e.g., a C6 to C12 aryl group, $R^{200}$ to $R^{203}$ may independently be, e.g., hydrogen, a cyano group, a C1 to C10 alkyl group, or a C6 to C12 aryl group, and In an implementation, $R^{200}$ to $R^{203}$ may be, e.g., all hydrogen or at least one thereof may be a phenyl group.

For example, Chemical Formula I-1B may be represented by one of Chemical Formulae I-1B-1 to Chemical Formula I-1B-8.

For example, $R^{42}$ to $R^{45}$ may be separate, and the first compound may be represented by Chemical Formula I-1B-1.

In an implementation, adjacent groups of $R^{42}$ to $R^{45}$ may be linked with each other to form a substituted or unsubstituted aliphatic, aromatic, or heteroaromatic monocyclic ring or a substituted or unsubstituted aliphatic, aromatic, or heteroaromatic polycyclic ring, and the first compound may be represented by one of Chemical Formulae I-1B-2 to I-1B-8.

[Chemical Formula I-1B-1]
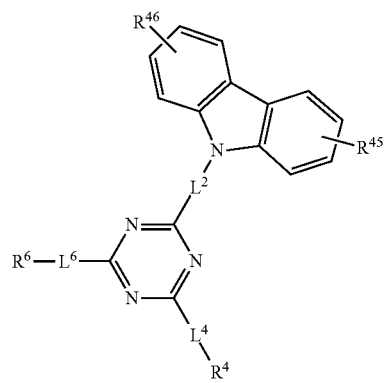
[Chemical Formula I-1B-2]
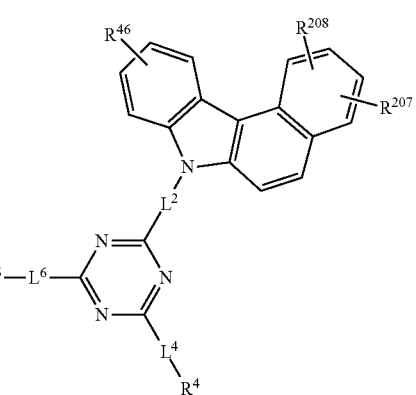
[Chemical Formula I-1B-3]
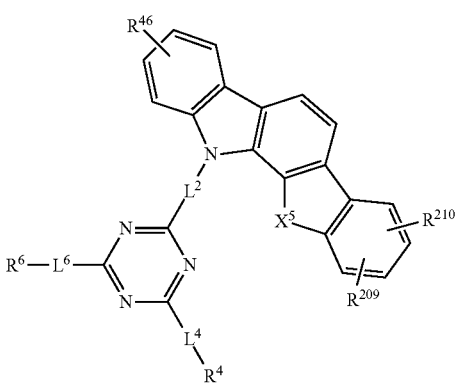
[Chemical Formula I-1B-4]
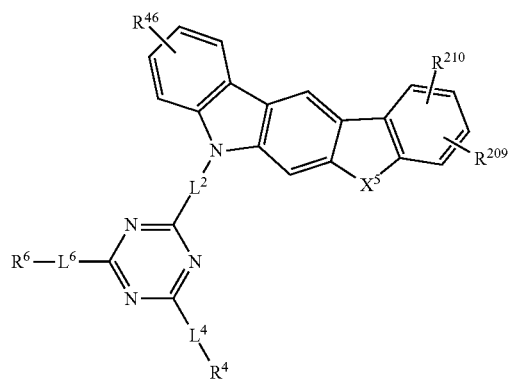
[Chemical Formula I-1B-5]
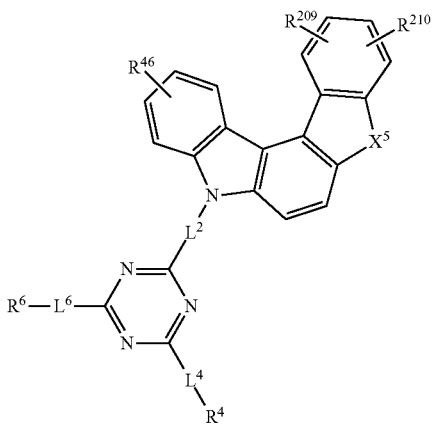
[Chemical Formula I-1B-6]
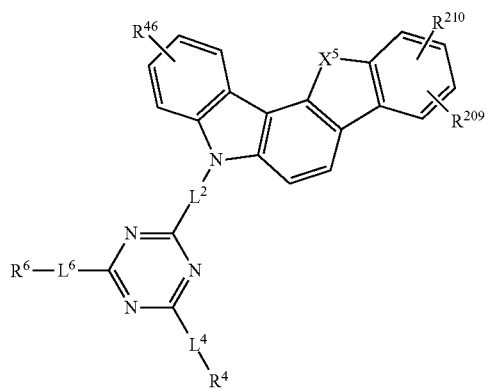
[Chemical Formula I-1B-7]
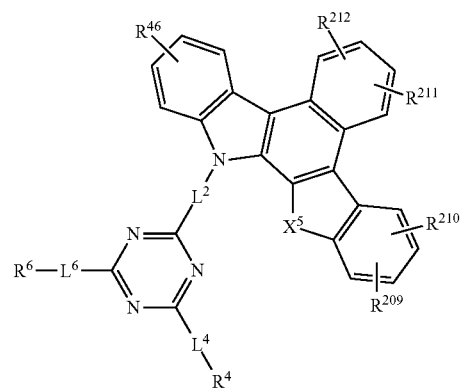

[Chemical Formula I-1B-8]

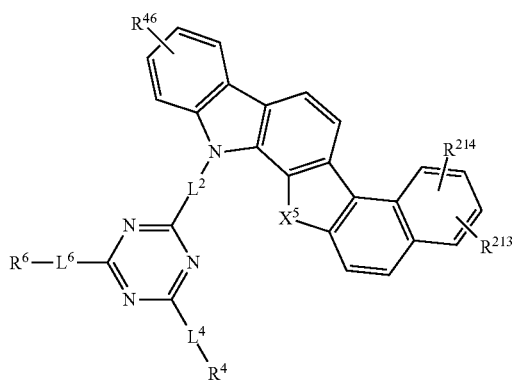

[Chemical Formula I-1C-1]

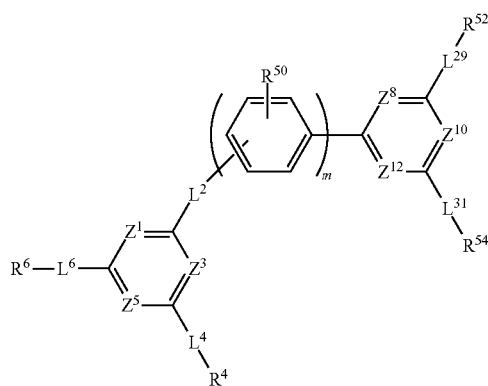

In Chemical Formula I-1B-1 to Chemical Formula I-1B-8, $L^2$, $L^4$, $L^6$, $R^4$, $R^6$, $R^{45}$, and $R^{46}$ may be the same as described above, $X^5$ may be, e.g., O, S, $CR^{205}R^{206}$, or $NR^m$, $R^m$ may be, e.g., a substituted or unsubstituted C6 to C30 aryl group, a substituted or unsubstituted C2 to C30 heterocyclic group, or a combination thereof, and $R^{205}$ to $R^{214}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In a more specific embodiment, $R^m$ may be, e.g., a C6 to C12 aryl group, $R^{205}$ and $R^{206}$ may be, e.g., independently be a C1 to C10 alkyl group or a C6 to C12 aryl group, and $R^{207}$ to $R^{214}$ may be, e.g., independently be hydrogen, a cyano group, a C1 to C10 alkyl group, or a C6 to C12 aryl group.

In an implementation, $R^{205}$ and $R^{206}$ may be, e.g., independently be a C1 to C5 alkyl group or a C6 to C12 aryl group and $R^{207}$ to $R^{214}$ may be, e.g., all hydrogen or at least one thereof may be a phenyl group.

In an implementation, at least one of $R^2$, $R^4$, and $R^6$ may be, e.g., a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group, or a substituted or unsubstituted benzoquinazolinyl group.

In an implementation, Chemical Formula I-1C may be, e.g., represented by one of Chemical Formula I-1C-1 to Chemical Formula I-1C-4.

In an implementation, $R^{51}$ to $R^{55}$ may be separate, and the first compound may be represented by Chemical Formula I-1C-1.

In an implementation, adjacent groups of $R^{51}$ to $R^{55}$ may be linked with each other to form a substituted or unsubstituted aliphatic, aromatic, or heteroaromatic monocyclic ring or a substituted or unsubstituted aliphatic, aromatic, or heteroaromatic polycyclic ring, and the first compound may be represented by one of Chemical Formula I-1C-2 to Chemical Formula I-1C-4.

[Chemical Formula I-1C-2]

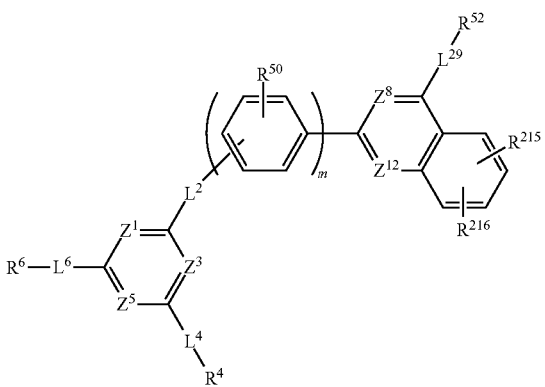

[Chemical Formula I-1C-3]

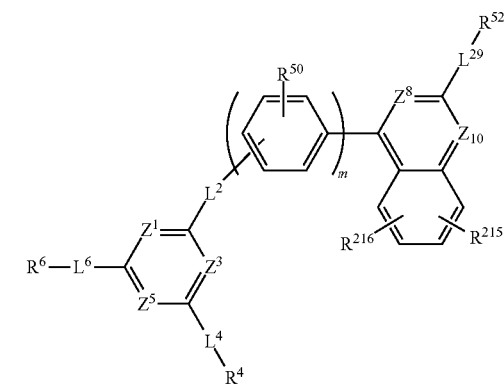

[Chemical Formula I-1C-4]

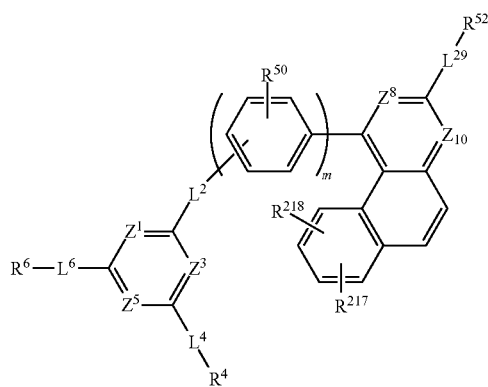

In Chemical Formula I-1C-1 to Chemical Formula I-1C-4, $Z^1$, $Z^3$ and $Z^5$, $Z^8$, $Z^{10}$ and $Z^{12}$, $L^2$, $L^4$, $L^6$, $R^4$, $R^6$, $R^{50}$, $R^{52}$, and m are the same as described above, at least one of $Z^8$, $Z^{10}$, and $Z^{12}$ may be, e.g., N, and $R^{215}$ to $R^{218}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In a more specific embodiment, $Z^1$, $Z^3$, and $Z^5$ of Chemical Formula I-1C-1 may be, e.g., each N or $Z^1$ and $Z^3$ may be, e.g., N and $Z^5$ may be, e.g., CH.

$Z^8$, $Z^{10}$, and $Z^{12}$ of Chemical Formula I-1C-1 may be, e.g., each N, $Z^8$ and $Z^{12}$ may be N and $Z^{10}$ may be, e.g., CH, or $Z^{10}$ and $Z^{12}$ may be, e.g., N and $Z^8$ may be, e.g., CH.

$L^{29}$ and $L^{31}$ of Chemical Formula I-1C-1 may independently be, e.g., a single bond, phenylene group or biphenylene group, $R^{52}$ and $R^{54}$ are independently a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group and when $R^{52}$ and $R^4$ are substituted, the substituent may be, e.g., a phenyl group, a naphthyl group, or a cyano group.

The m of Chemical Formula I-1C-1 may be 1 or 2.

In an embodiment, $Z^1$, $Z^3$ and $Z^5$ of Chemical Formula I-1C-2 may independently may be, e.g., N, one of $Z^8$ or $Z^{12}$ may be, e.g., N, and remaining groups may be, e.g., CH.

$L^{29}$ of Chemical Formula I-1C-2 may be, e.g., a single bond or phenylene.

$R^{52}$ of Chemical Formula I-1C-2 may be, e.g., a C6 to C12 aryl group.

The m of Chemical Formula I-1C-2 may be, e.g., 1 or 2.

$R^{215}$ and $R^{216}$ of Chemical Formula I-1C-2 may independently be, e.g., hydrogen, a cyano group, a C1 to C10 alkyl group, or a C6 to C12 aryl group.

In an implementation, the $R^{215}$ and $R^{216}$ may be, e.g., all hydrogen or at least one thereof may be a phenyl group.

In an embodiment, $Z^1$, $Z^3$, and $Z^5$ of Chemical Formula I-1C-3 may independently be N and $Z^8$ and $Z^{10}$ may independently be N.

In an embodiment, $Z^1$, $Z^3$, and $Z^5$ of Chemical Formula I-1C-4 may independently be N, $Z^8$ and $Z^{10}$ may independently be N.

$R^{217}$ and $R^{218}$ of Chemical Formula I-1C-4 may independently be, e.g., hydrogen, a cyano group, a C1 to C10 alkyl group, or a C6 to C12 aryl group.

In an implementation, the $R^{217}$ and $R^{218}$ may be, e.g., all hydrogen or at least one thereof may be a phenyl group.

$L^{29}$, $R^{52}$, m, $R^{215}$, and $R^{216}$ of Chemical Formulae I-1C-3 and I-1C-4 may be, e.g., the same as in Chemical Formula I-1C-2.

In an implementation, the first compound and the second compound may be represented by Chemical Formula I-2, respectively.

$L^6$ of Chemical Formula I-2 may be, e.g., a substituted or unsubstituted C6 to C12 arylene group or a substituted or unsubstituted carbazolylene group.

$R^6$ of Chemical Formula I-2 may be, e.g., a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, or a substituted or unsubstituted dibenzothiophenyl group.

$R^d$ and $R^e$ of Chemical Formula I-2 may independently be, e.g., hydrogen, a cyano group, a C1 to C10 alkyl group, or a C6 to C12 aryl group.

In an implementation, $R^d$ and $R^e$ may be, e.g., all hydrogen or at least one thereof may be a phenyl group.

In an implementation, $Z^1$ and $Z^5$ of Chemical Formula I-2 may independently be N and $Z^4$ may be C-$L^4$-$R^4$.

In an implementation, $Z^1$ and $Z^4$ of Chemical Formula I-2 may independently be N, C-$L^5$-$R^5$.

In an implementation, Chemical Formula I-2 may be represented by Chemical Formula I-2A or Chemical Formula I-2B.

[Chemical Formula I-2A]

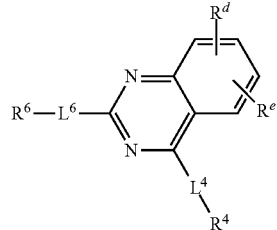

[Chemical Formula I-2B]

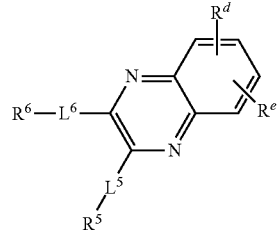

In Chemical Formula I-2A and Chemical Formula I-2B, $L^4$ to $L^6$, $R^d$, $R^e$, and $R^4$ to $R^6$ may be the same as described above.

In an implementation, $L^4$ to $L^6$ of Chemical Formula I-2A and Chemical Formula I-2B may independently be, e.g., a single bond, a phenylene group, a biphenylene group, or a carbazolylene group.

At least one of $R^4$ to $R^6$ of Chemical Formula I-2A and Chemical Formula I-2B may be, e.g., a substituted or unsubstituted carbazolyl group, a substituted or unsubstituted indolocarbazolyl group, a substituted or unsubstituted fused dibenzofuranyl group, a substituted or unsubstituted fused dibenzothiophenyl group, or a substituted or unsubstituted fused indolocarbazolyl group.

In an implementation, Chemical Formula I-2A may be represented by one of Chemical Formulae I-2A-1 to I-2A-4.

[Chemical Formula I-2A-1]

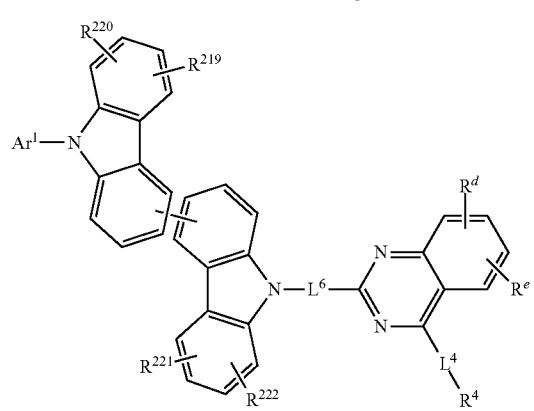

-continued

[Chemical Formula I-2A-2]

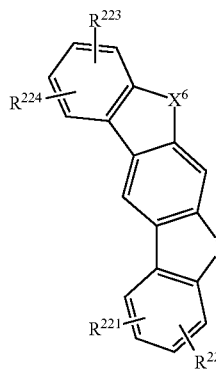

[Chemical Formula I-2A-3]

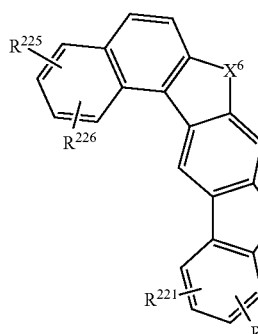

[Chemical Formula I-2A-4]

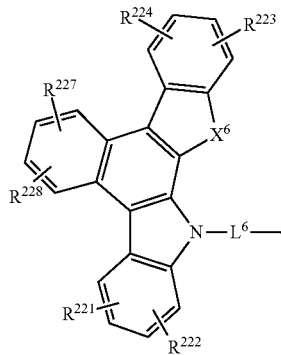

In Chemical Formulae I-2A-1 to I-2A-4, $L^4$ and $L^6$, $R^d$, $R^e$ and $R^4$ may be the same as described above, $X^6$ may be, e.g., O, S, or $NR''$, $Ar^1$ may be, e.g., a substituted or unsubstituted C6 to C30 aryl group, a substituted or unsubstituted C2 to C30 heterocyclic group, or a combination thereof, $R''$ may be, e.g., a substituted or unsubstituted C6 to C30 aryl group, a substituted or unsubstituted C2 to C30 heterocyclic group, or a combination thereof, and $R^{219}$ to $R^{228}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an implementation, $Ar^1$ and the $R''$ may independently be a C6 to C12 aryl group, and $R^{219}$ to $R^{228}$ may independently be hydrogen, a cyano group, a C1 to C10 alkyl group, or a C6 to C12 aryl group.

In an implementation, the $R^{219}$ to $R^{228}$ may be, e.g., all hydrogen or at least one thereof may be a phenyl group.

In an implementation, Chemical Formula I-2B may be represented by one of Chemical Formula I-2B-1 to Chemical Formula I-2B-3.

[Chemical Formula I-2B-1]

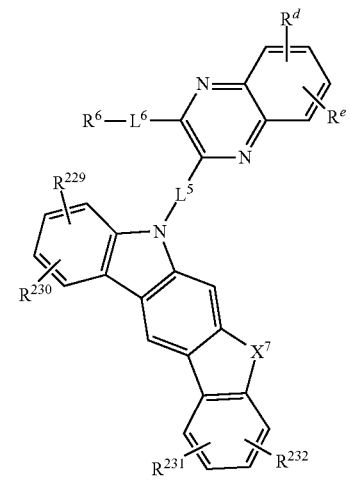

[Chemical Formula I-2B-2]

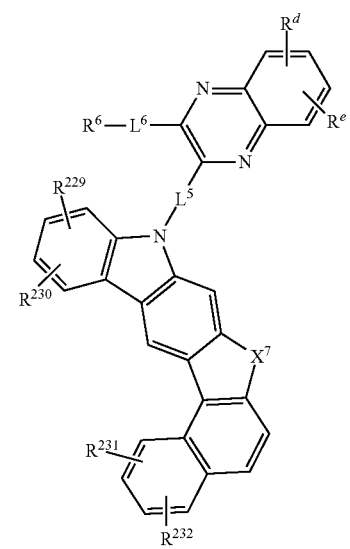

[Chemical Formula I-2B-3]

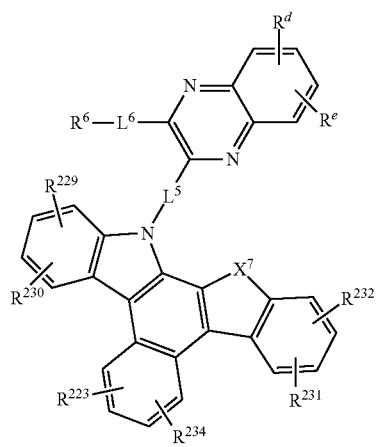

In Chemical Formula I-2B-1 to Chemical Formula I-2B-3, $L^5$ and $L^6$, $R^d$, $R^e$, and $R^6$ may be the same as described above,

- $X^7$ may be, e.g., O, S, or $NR^o$,
- $R^o$ may be, e.g., a substituted or unsubstituted C6 to C30 aryl group, a substituted or unsubstituted C2 to C30 heterocyclic group, or a combination thereof, and
- $R^{229}$ to $R^{234}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an implementation, $R^o$ may be a C6 to C12 aryl group, and

- $R^{229}$ to $R^{234}$ may independently be hydrogen, a cyano group, a C1 to C10 alkyl group, or a C6 to C12 aryl group.

In an implementation, $R^{229}$ to $R^{234}$ may be, e.g., all hydrogen or at least one thereof may be a phenyl group.

In an implementation, the first compound and the second compound may be represented by Chemical Formula I-3.

$R^f$ to $R^h$ of Chemical Formula I-3 may independently be hydrogen, a cyano group, a C1 to C10 alkyl group, or a C6 to C12 aryl group.

In an implementation, $R^f$ to $R^h$ may be, e.g., all hydrogen or at least one thereof may be a phenyl group.

In an implementation, $Z^1$ and $Z^5$ of Chemical Formula I-3 may independently be N, $Z^4$ may be $C$-$L^4$-$R^4$, and $Z^6$ may be $C$-$L^6$-$R^6$.

In an implementation, $Z^4$ and $Z^6$ of Chemical Formula I-3 may be N, $Z^1$ may be $C$-$L^1$-$R^1$, and $Z^5$ may be $C$-$L^5$-$R^5$.

In an implementation, Chemical Formula I-3 may be represented by Chemical Formula I-3A or Chemical Formula I-3B.

[Chemical Formula I-3A]

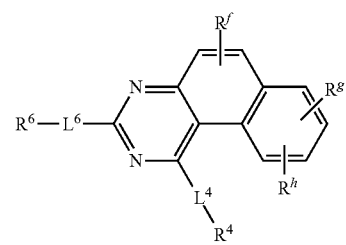

[Chemical Formula I-3B]

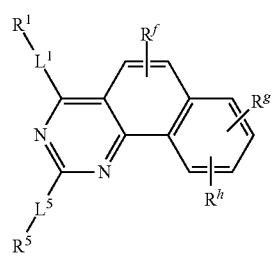

In Chemical Formula I-3A and Chemical Formula I-3B, $L^1$, $L^4$ to $L^6$, $R^f$, $R^g$, $R^h$, $R^1$, and $R^4$ to $R^6$ may be the same as described above.

In an implementation, Chemical Formula I-3A may be represented by one of Chemical Formulae I-3A-1 to I-3A-3.

[Chemical Formula I-3A-1]

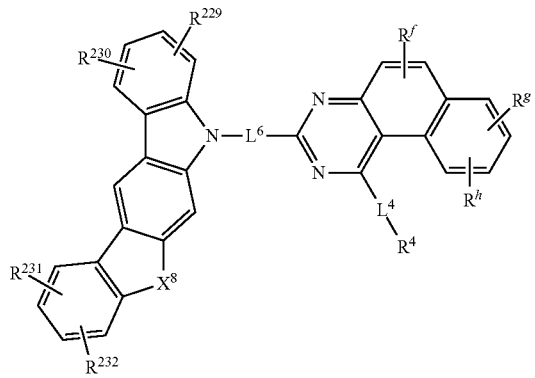

[Chemical Formula I-3A-2]

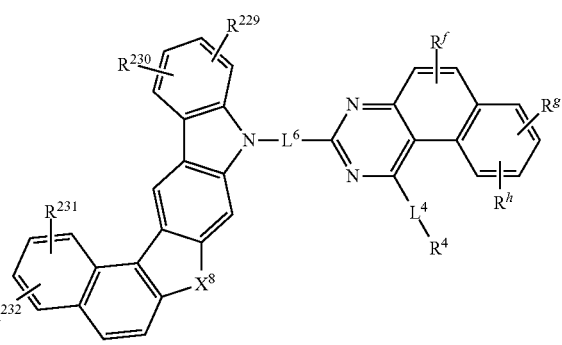

[Chemical Formula 3A-3]

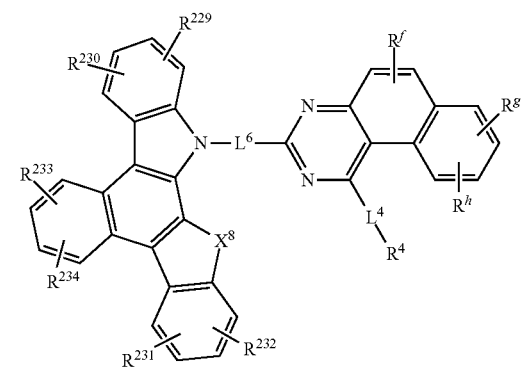

In Chemical Formula I-3A-1 to Chemical Formula I-3A-3, $L^4$ and $L^6$, $R^4$, $R^f$, $R^g$, and $R^h$ are the same as described above,

- $X^8$ may be, e.g., O, S, or $NR^p$,
- $R^p$ may be, e.g., a substituted or unsubstituted C6 to C30 aryl group, a substituted or unsubstituted C2 to C30 heterocyclic group, or a combination thereof, and
- $R^{229}$ to $R^{234}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an implementation, $R^p$ may be, e.g., a C6 to C12 aryl group,

- $R^{229}$ to $R^{234}$ may be, e.g., independently be hydrogen, a cyano group, a C1 to C10 alkyl group, or a C6 to C12 aryl group, and In an implementation, $R^{229}$ to $R^{234}$ may be, e.g., all hydrogen or at least one thereof may be a phenyl group.

In an implementation, Chemical Formula I-3B may be represented by one of Chemical Formulae I-3B-1 to I-3B-3.

[Chemical Formula I-3B-1]

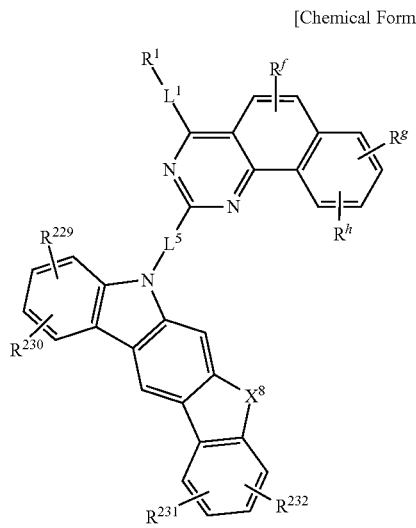

[Chemical Formula I-3B-2]

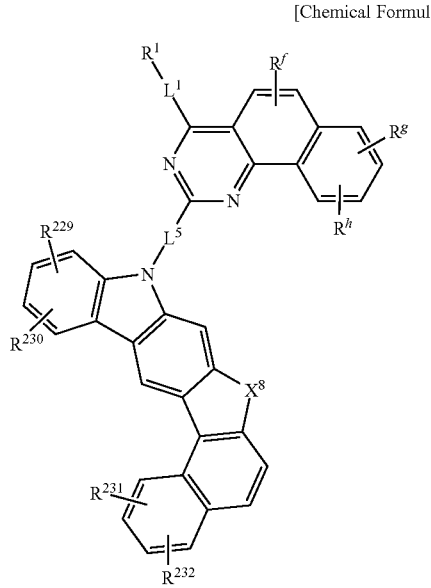

[Chemical Formula I-3B-3]

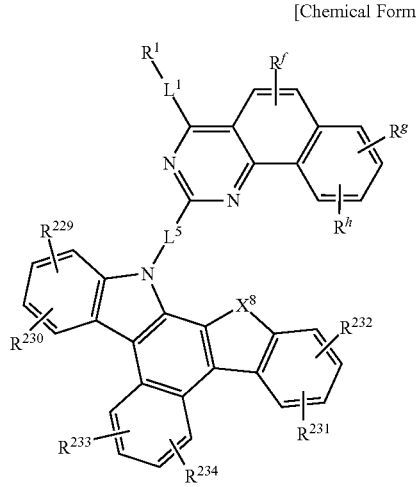

In Chemical Formula I-3B-1 to Chemical Formula I-3B-3, $L^1$ and $L^5$, $R^f$, $R^g$, and $R^h$ may be the same as described above.

$X^8$ may be, e.g., O, S, or $NR^p$, $R^p$ may be, e.g., a substituted or unsubstituted C6 to C30 aryl group, a substituted or unsubstituted C2 to C30 heterocyclic group, or a combination thereof, and $R^{229}$ to $R^{234}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an implementation, $R^p$ may be, e.g., a C6 to C12 aryl group, $R^{229}$ to $R^{234}$ may independently be, e.g., hydrogen, a cyano group, a C1 to C10 alkyl group, or a C6 to C12 aryl group, and $R^{229}$ to $R^{234}$ may be, e.g., all hydrogen or at least one thereof may be a phenyl group.

In an implementation, the first compound may be represented by Chemical Formula I-4.

In an implementation, $Z^4$ and $Z^6$ of Chemical Formula I-4 may be N, $Z^1$ may be $C-L^1-R^1$, and $Z^5$ may be $C-L^5-R^5$.

In an implementation, $Z^1$ and $Z^5$ of Chemical Formula I-4 may be N, $Z^4$ may be $C-L^4-R^4$, and $Z^6$ may be $C-L^6-R^6$.

In an implementation, Chemical Formula I-4 may be represented by Chemical Formula I-4A or Chemical Formula I-4B.

[Chemical Formula I-4A]

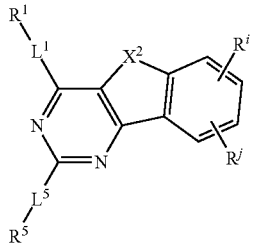

[Chemical Formula I-4B]

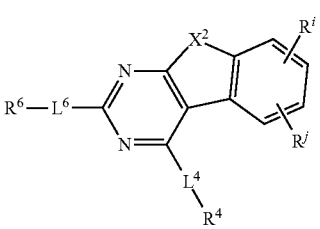

In Chemical Formula I-4A and Chemical Formula I-4B, $X^2$, $L^1$, $L^4$ to $L^6$, $R^i$, $R^j$, $R^1$, and $R^4$ to $R^6$ are the same as described above.

In an implementation, Chemical Formula I-4A may be represented by one of Chemical Formula I-4A-1 to Chemical Formula I-4A-4.

[Chemical Formula I-4A-1]

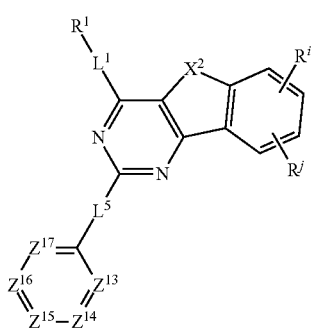

[Chemical Formula I-4A-2]

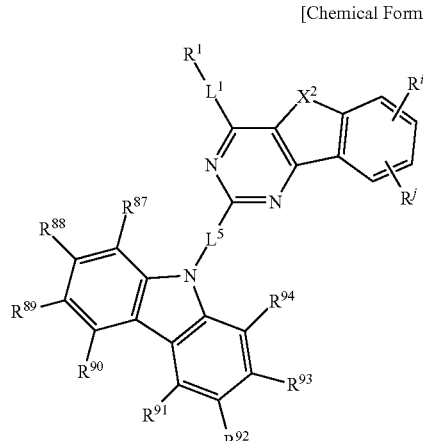

[Chemical Formula I-4A-3]

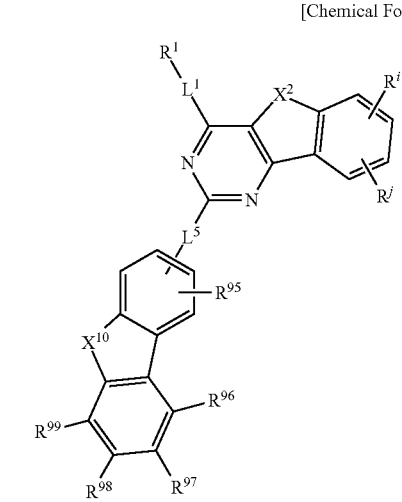

[Chemical Formula I-4A-4]

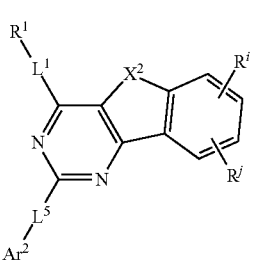

In Chemical Formula I-4A-1 to Chemical Formula I-4A-4, $X^2$, $L^1$, $L^5$, $R^1$, $R^i$, and $R^j$ may be the same as described above, $X^{10}$ may be, e.g., O, S, or $NR^s$, $Z^{13}$ may be, e.g., N or C-$L^{41}$-$R^{82}$, $Z^{14}$ may be, e.g., N or C-$L^{42}$-$R^{83}$, $Z^{15}$ may be, e.g., N or C-$L^{43}$-$R^{84}$, $Z^{16}$ may be, e.g., N or C-$L^{44}$-$R^{85}$, $Z^{17}$ may be, e.g., N or C-$L^{45}$-$R^{86}$, at least one of $Z^{13}$ to $Z^{17}$ may be, e.g., N, $L^{41}$ to $L^{45}$ may be, e.g., independently a single bond, a substituted or unsubstituted C6 to C20 arylene group, a substituted or unsubstituted C2 to C20 heterocyclic group, or a combination thereof, and $R^{82}$ to $R^{99}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In an implementation, $L^1$ may be, e.g., a single bond or C6 to C12 arylene group and $L^5$ may be a single bond or a C6 to C20 arylene group.

In an implementation, $R^1$ may be, e.g., a phenyl group, a biphenyl group, a dibenzofuranyl group, or a dibenzothiophenyl group, and $R^i$ and $R^j$ may independently be, e.g., hydrogen, a cyano group, a C1 to C10 alkyl group, or a C6 to C12 aryl group and may be all hydrogen or at least one thereof may be a phenyl group.

For example, Chemical Formula I-4B may be represented by one of Chemical Formula I-4B-1 to Chemical Formula I-4B-4.

[Chemical Formula I-4B-1]

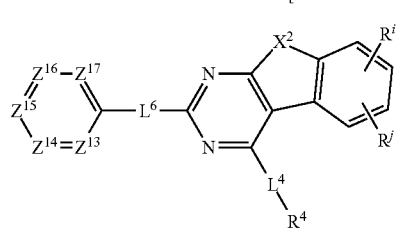

[Chemical Formula I-4B-2]

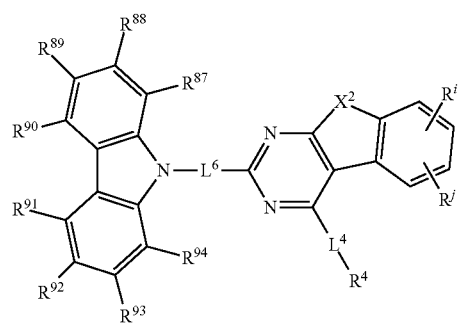

[Chemical Formula I-4B-3]

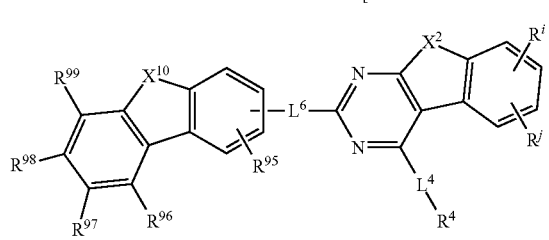

[Chemical Formula I-4B-4]

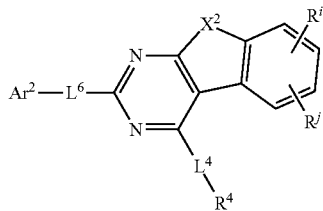

In Chemical Formula I-4B-1 to Chemical Formula I-4B-4, $X^2$, $X^{10}$, $L^4$, $L^6$, $L^{41}$ to $L^{45}$, $R^4$, $R^i$, $R^j$, and $R^{82}$ to $R^{99}$ may be the same as described above.

In an implementation, $L^4$ and $L^6$ may independently be, e.g., a single bond or a C6 to C12 arylene group.

In an implementation, $R^4$ may be, e.g., a phenyl group, a biphenyl group, a dibenzofuranyl group, or a dibenzothiophenyl group, and $R^i$ and $R^j$ may be, e.g., independently hydrogen, a cyano group, a C1 to C10 alkyl group, or a C6 to C12 aryl group and may be all hydrogen or at least one thereof may be a phenyl group.

The hexagonal (six-membered) ring consisting of $Z^{13}$ to $Z^{17}$ linked with $L^5$ or $L^6$ in Chemical Formula I-4A-1 and Chemical Formula I-4B-1 may be, e.g., a substituted or unsubstituted pyrimidinyl group or a substituted or unsubstituted triazinyl group.

$X^{10}$-containing hetero aromatic polycyclic rings linked with $L^5$ or $L^6$ in Chemical Formula I-4A-3 and Chemical Formula I-4B-3 may be, e.g., a substituted or unsubstituted carbazolyl group, a substituted or unsubstituted dibenzofuranyl group, or a substituted or an unsubstituted dibenzothiophenyl group.

$Ar^2$ linked with $L^5$ or $L^6$ in Chemical Formula I-4A-4 and Chemical Formula I-4B-4 may be, e.g., a substituted or unsubstituted phenyl group, a substituted or unsubstituted biphenyl group, or a substituted or unsubstituted terphenyl group.

In an implementation, when substituted, the substituent may be a cyano group or a C6 to C12 aryl group.

For example, the first compound may be represented by Chemical Formula I-1A or I-1B.

In an embodiment, the first compound may be represented by Chemical Formula I-1A-1 or I-1B-1.

In an implementation, the first compound may be, e.g., a compound of Group 1.

[Group 1]

[1-1]

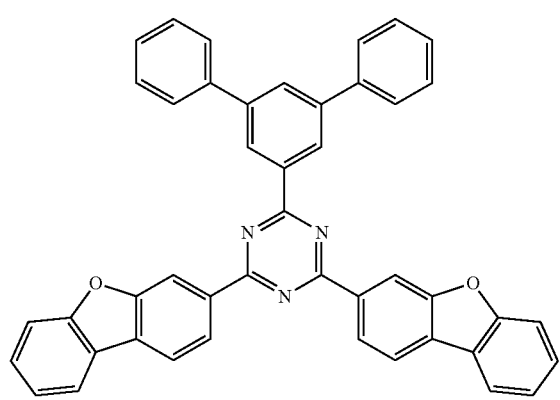

[1-2]

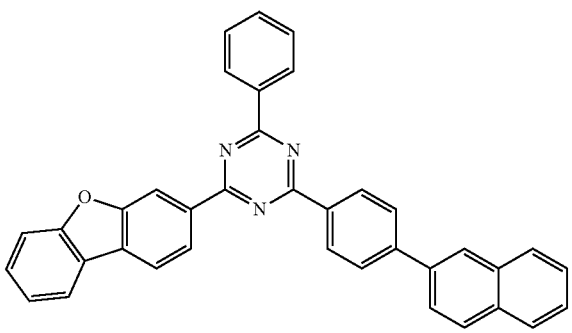

[1-3]

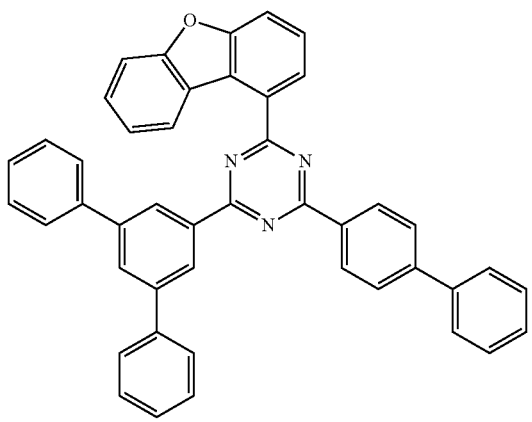

[1-4]

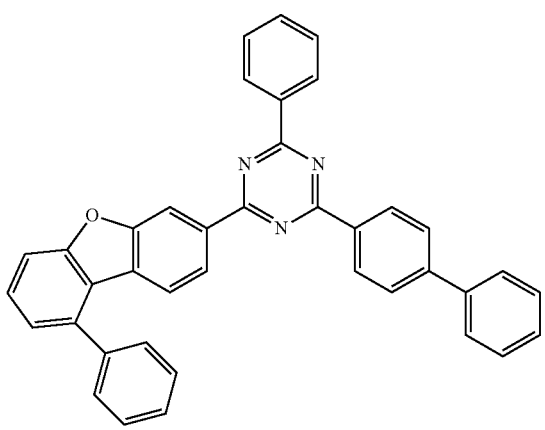

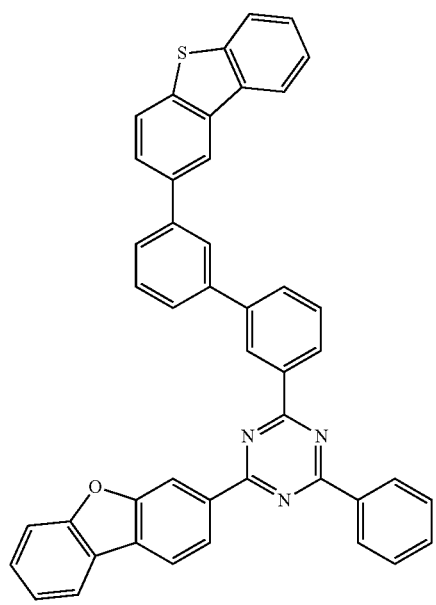
[1-5]
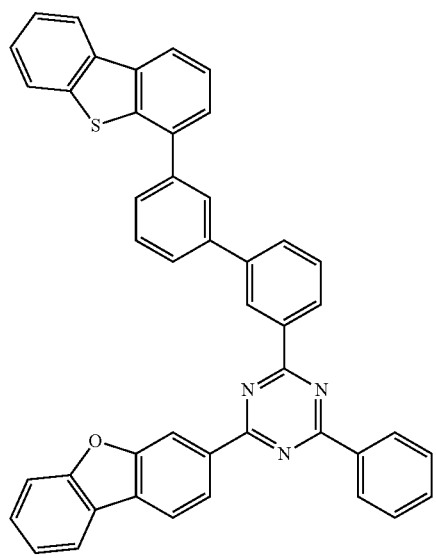
[1-6]
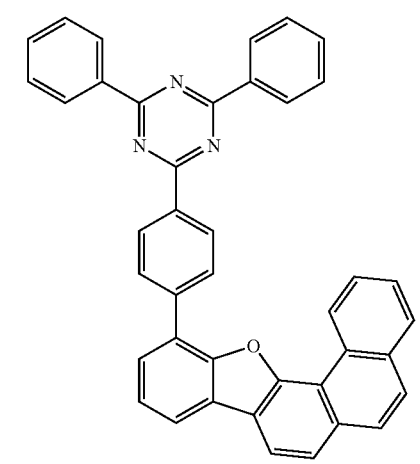
[1-7]
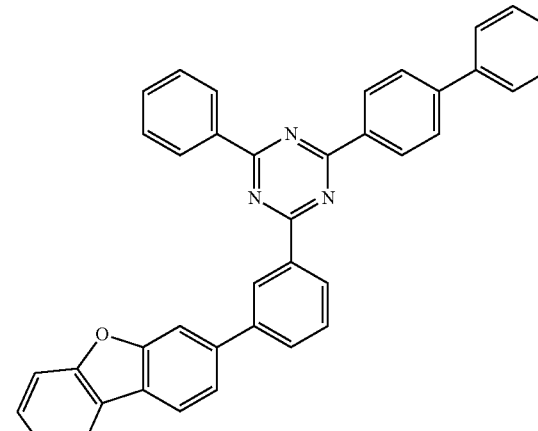
[1-8]
[1-9]
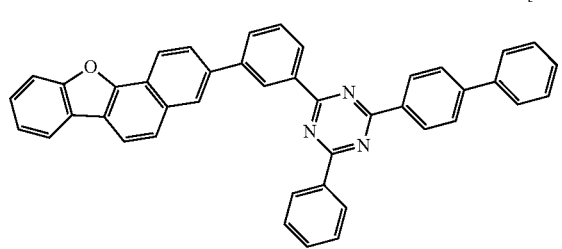
[1-10]

[1-11]
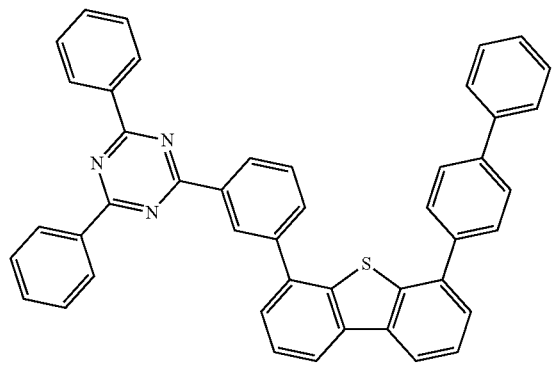
[1-12]
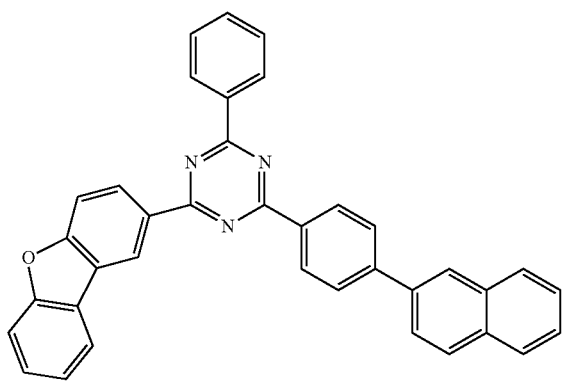
[1-13]
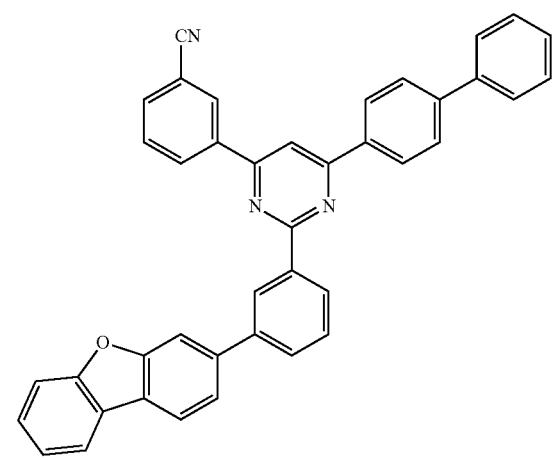
[1-14]
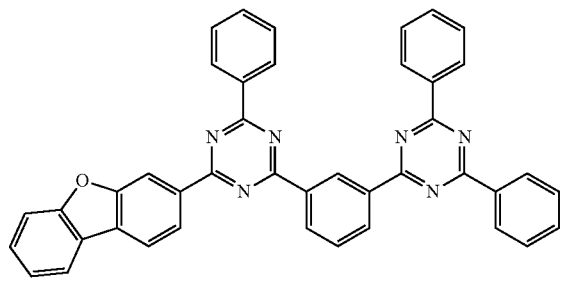
[1-15]
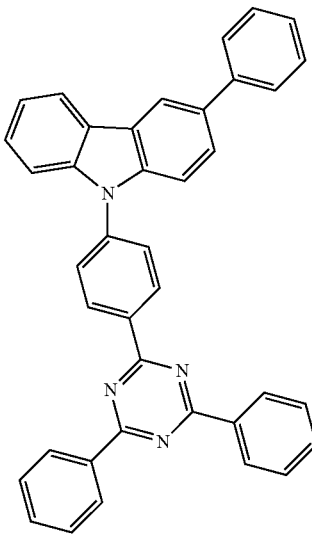
[1-16]
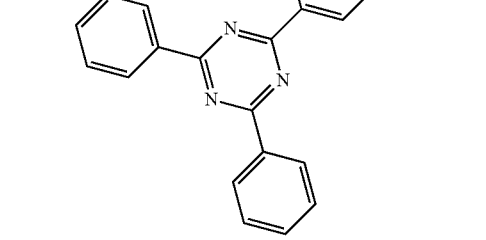
[1-17]
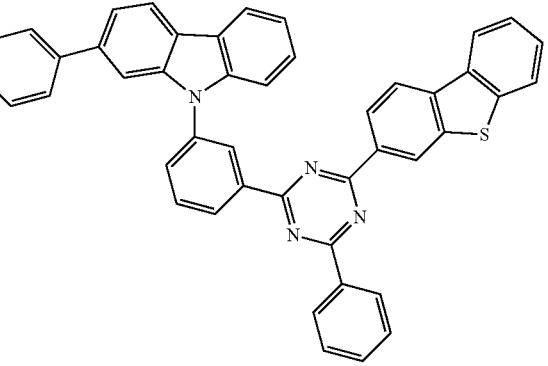

[1-18]
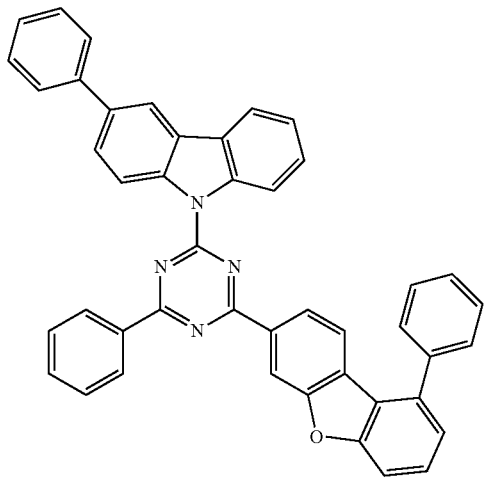
[1-21]
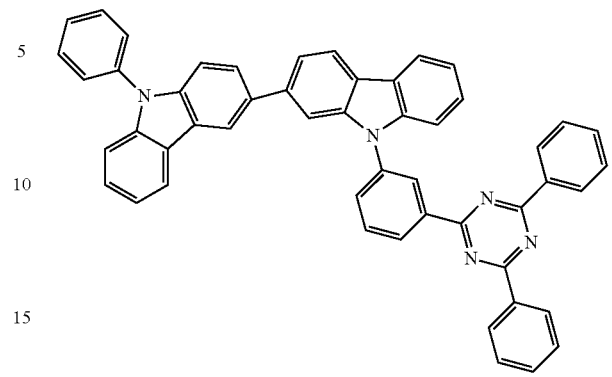
[1-19]
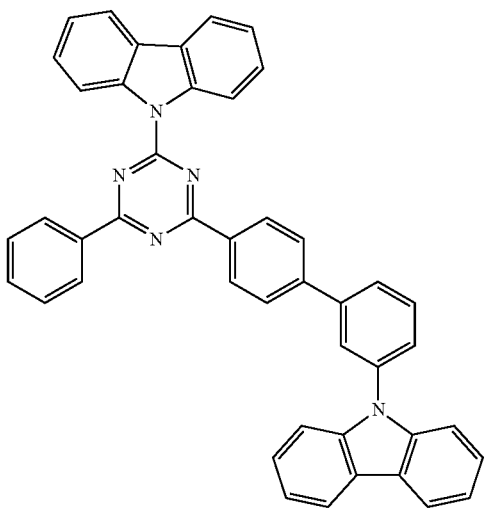
[1-22]
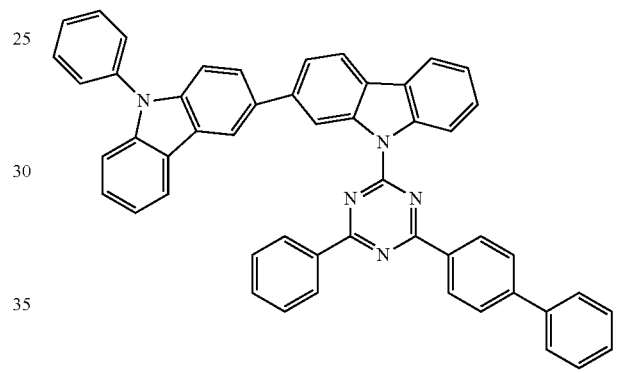
[1-20]
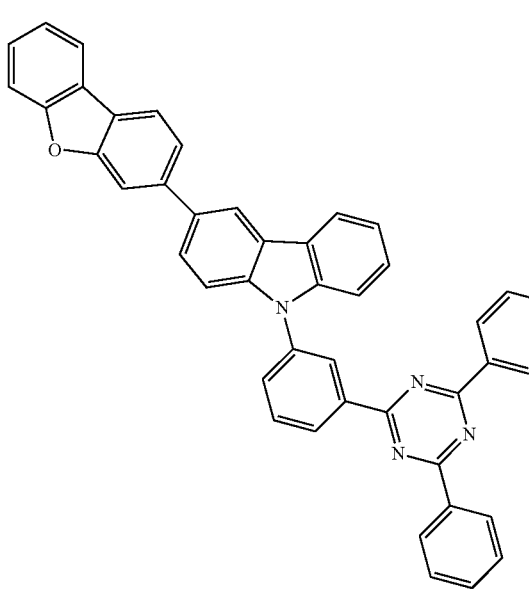
[1-23]
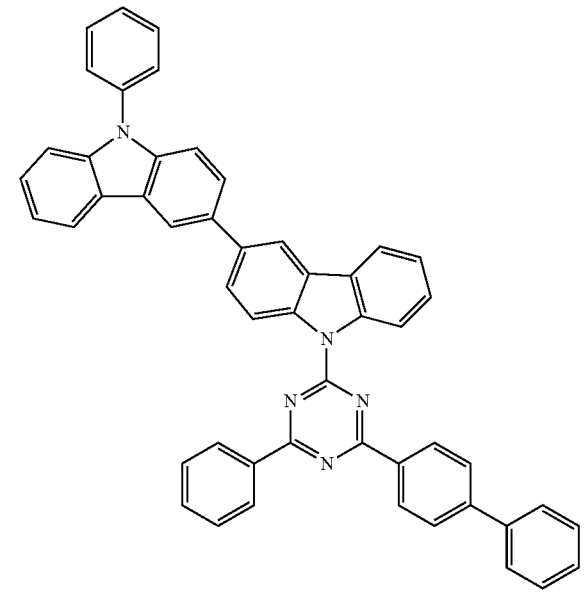

[1-24]
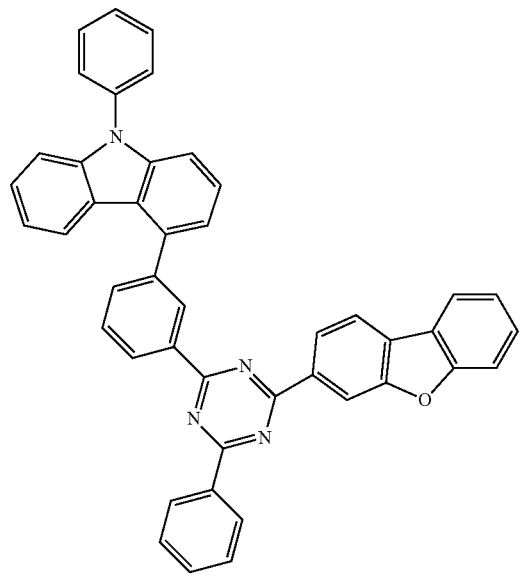
[1-25]
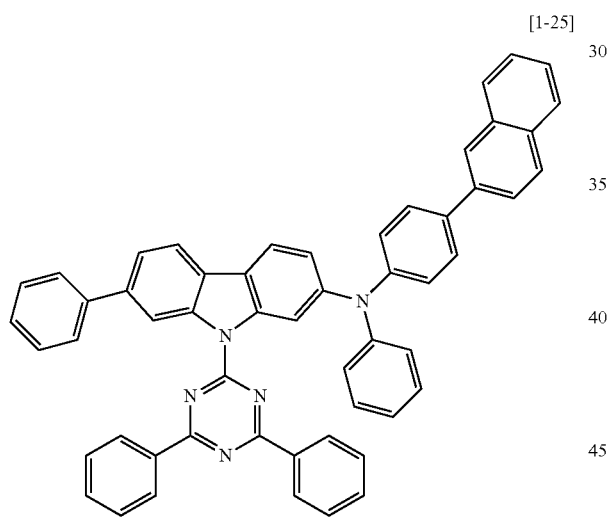
[1-26]
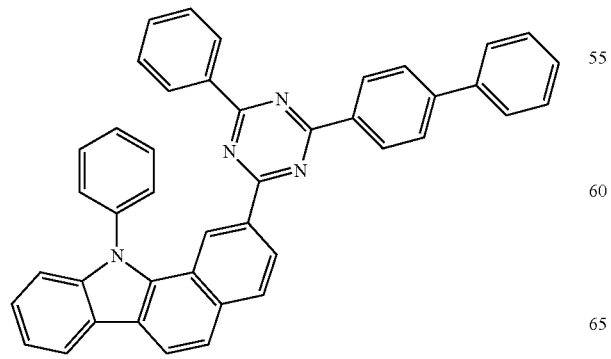
[1-27]
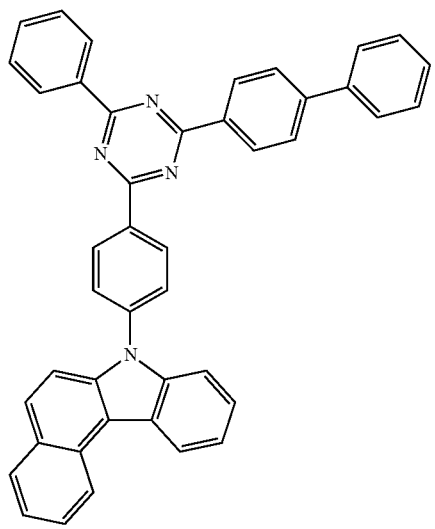
[1-28]
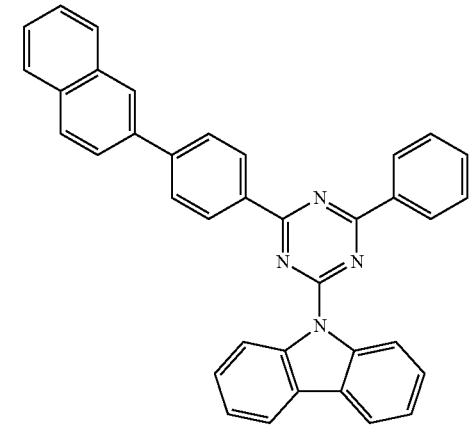
[1-29]
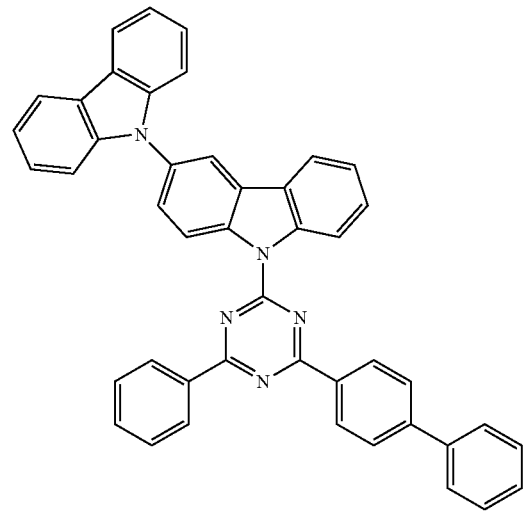

[1-30]
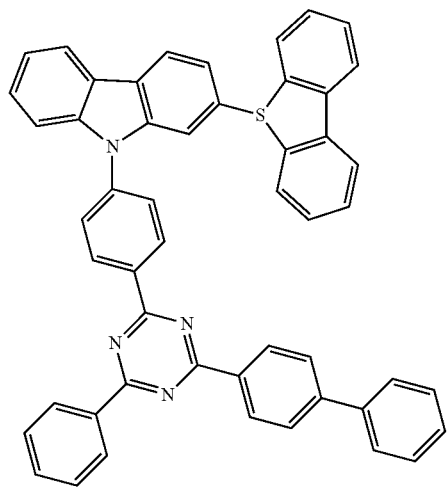
[1-33]
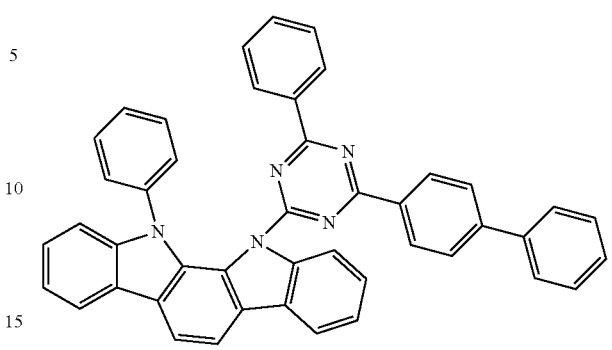
[1-34]
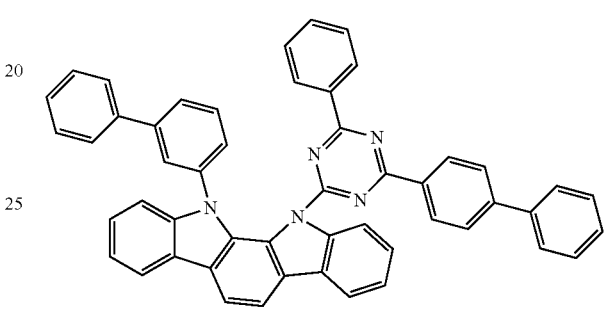
[1-31]
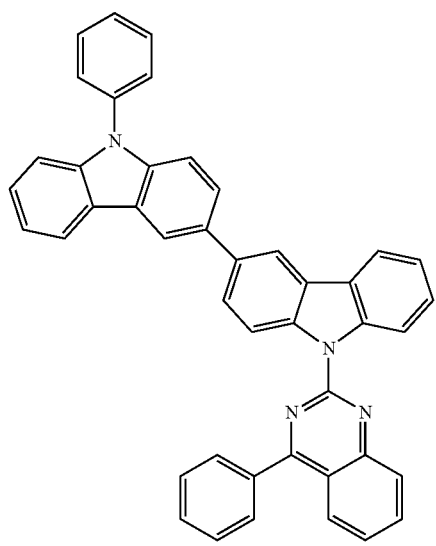
[1-35]
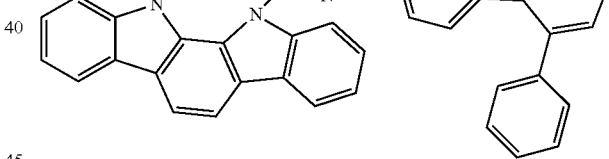
[1-32]
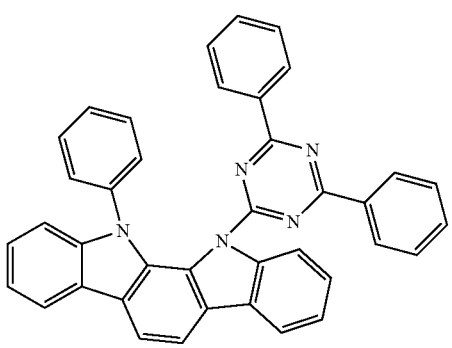
[1-36]
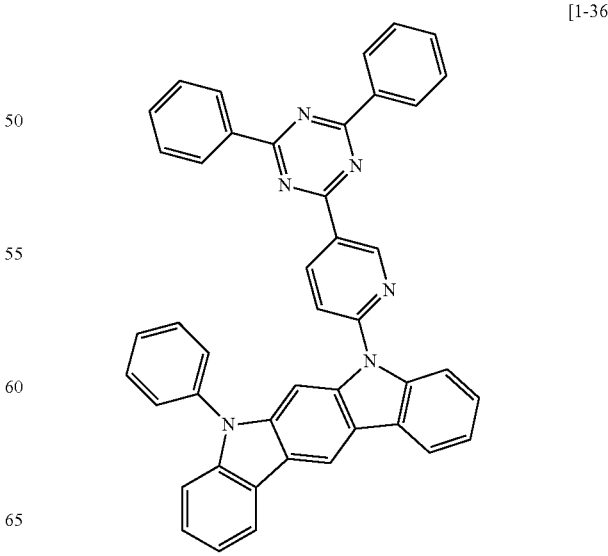

[1-37]
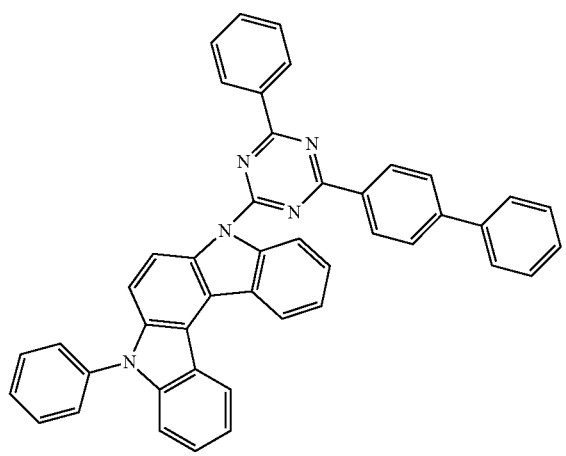
[1-40]
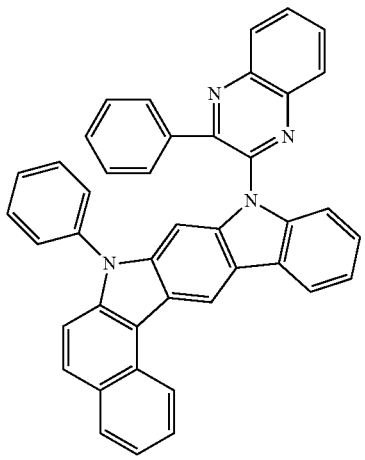
[1-38]
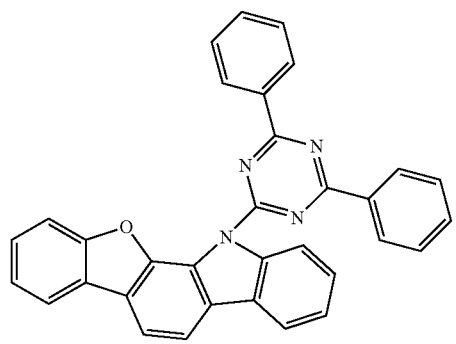
[1-41]
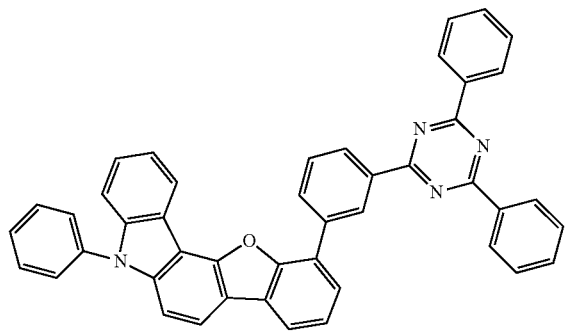
[1-39]
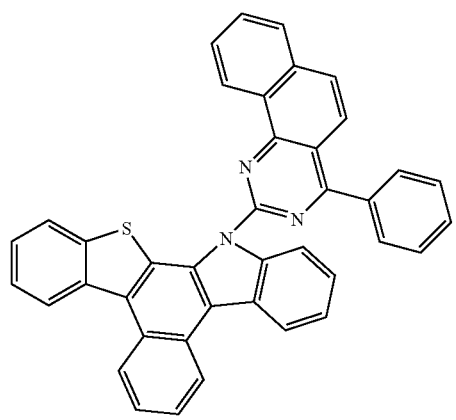
[1-42]
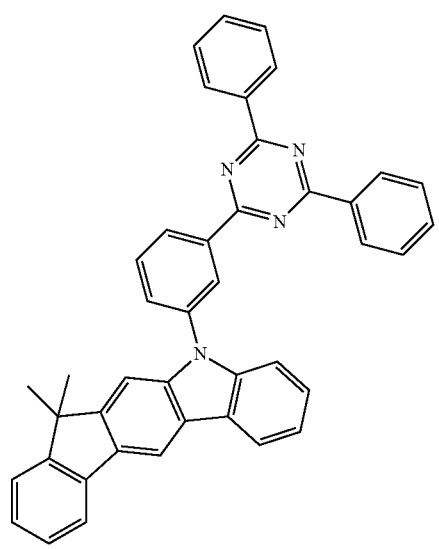

[1-43]
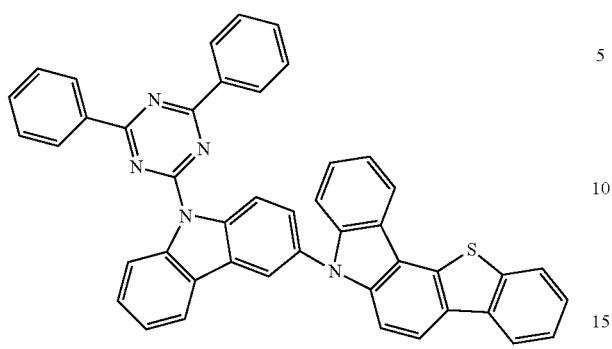
[1-44]
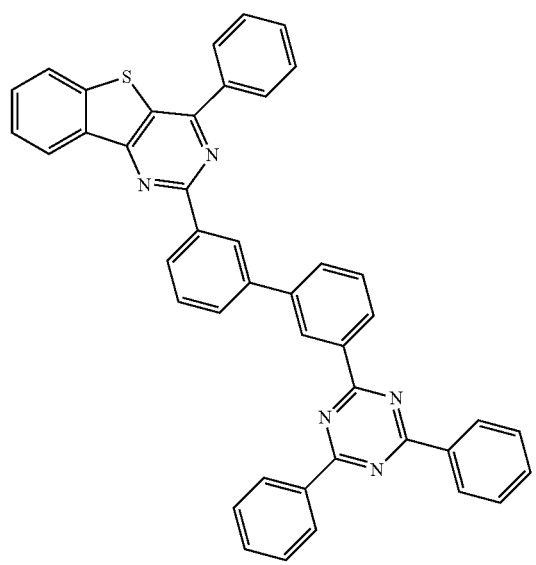
[1-45]
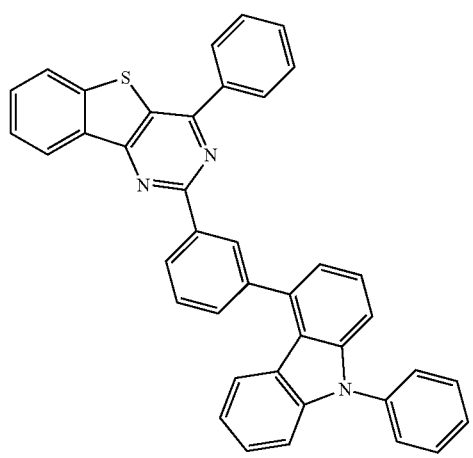
[1-46]
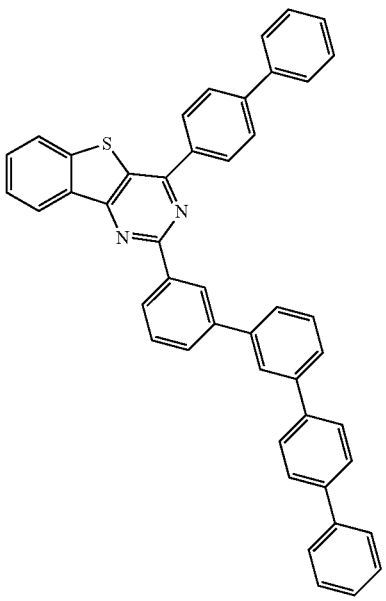
[1-47]
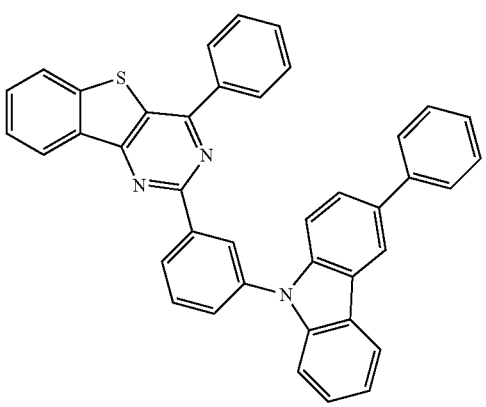
[1-48]

[1-49]
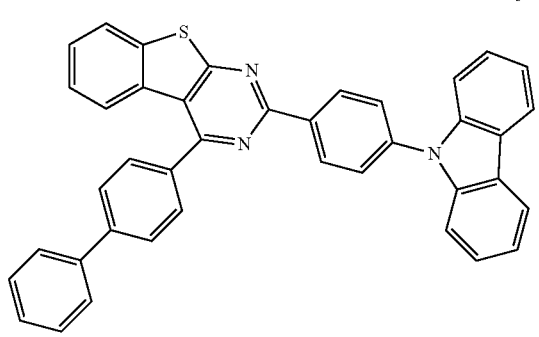
[1-52]
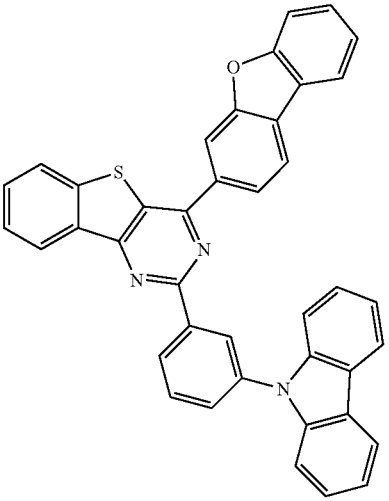
[1-50]
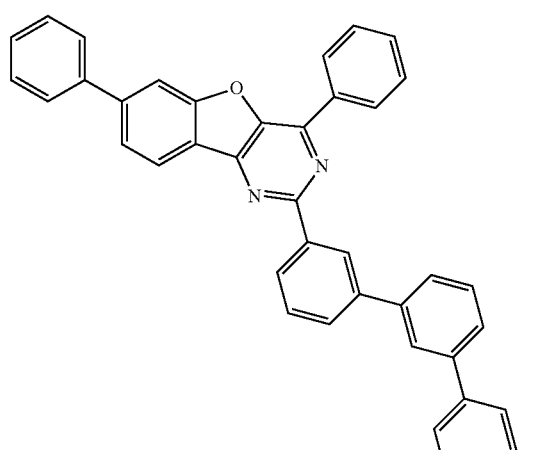
[1-53]
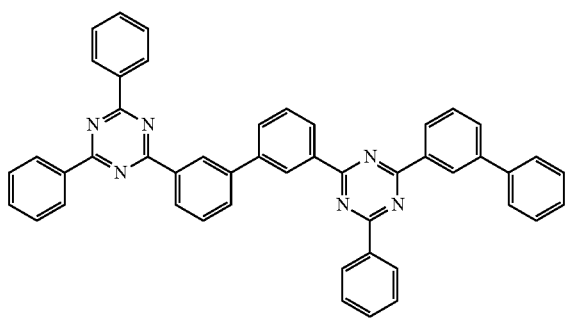
[1-54]
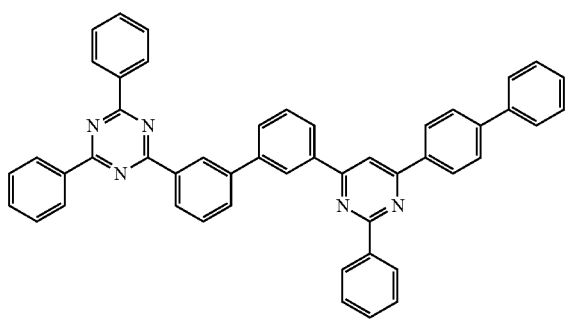
[1-51]
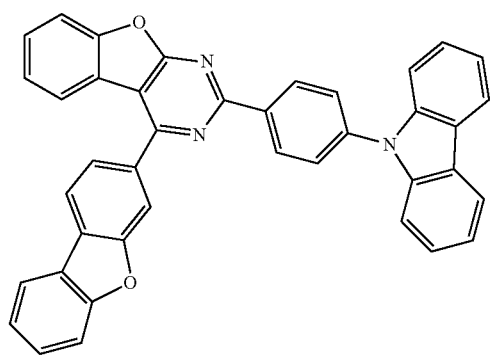
[1-55]
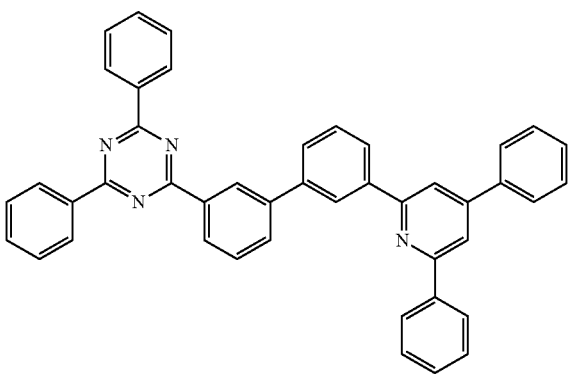

[1-56]
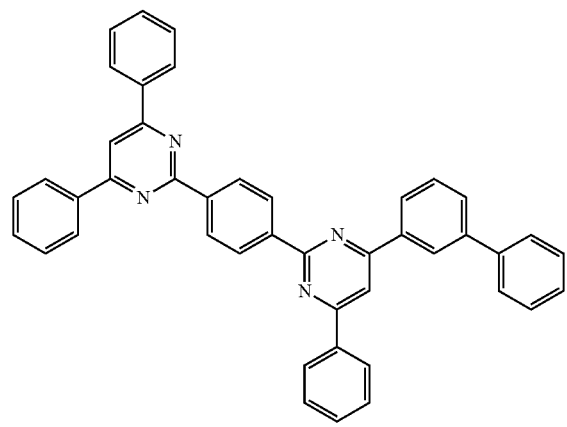
[1-57]
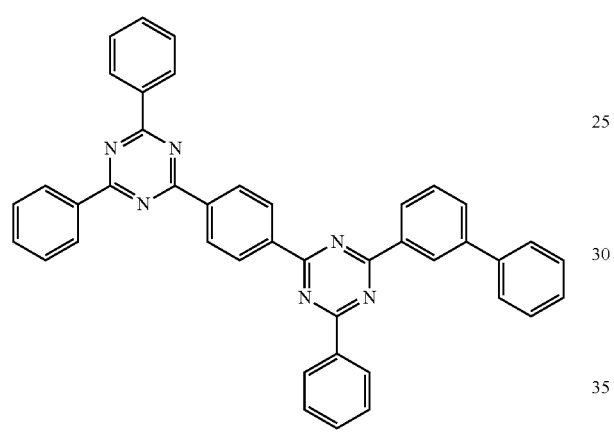
[1-58]
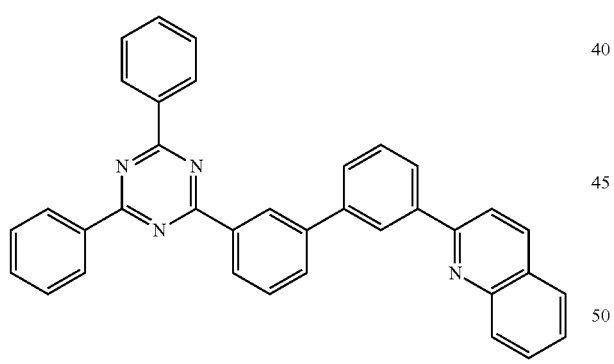
[1-59]
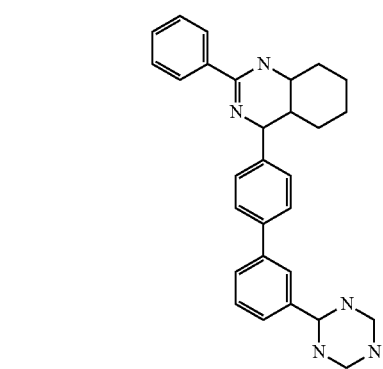
[1-60]
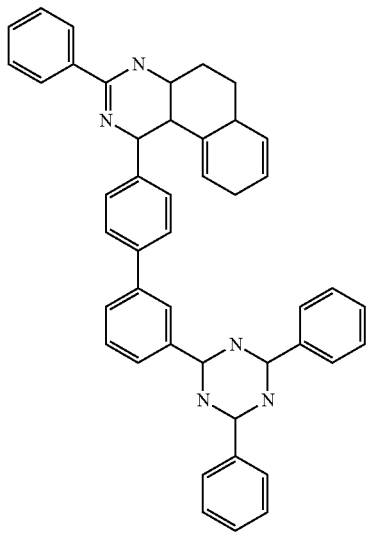
[1-61]
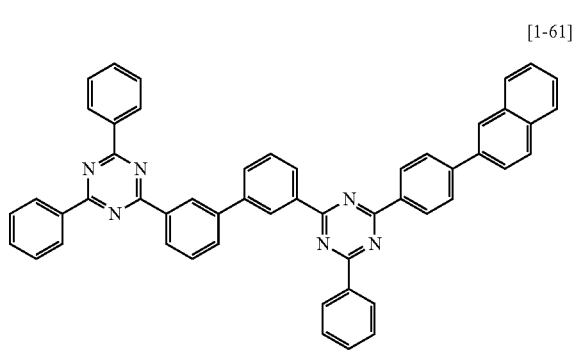
[1-62]
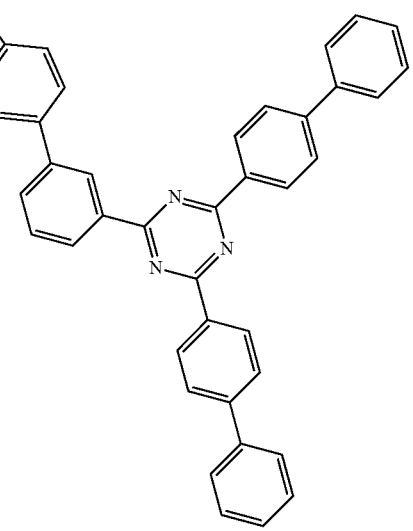

[1-63]
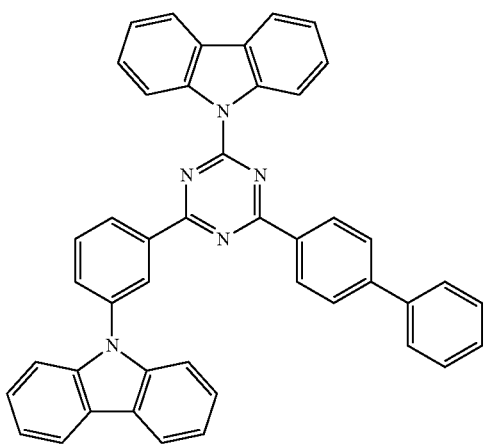
[1-66]
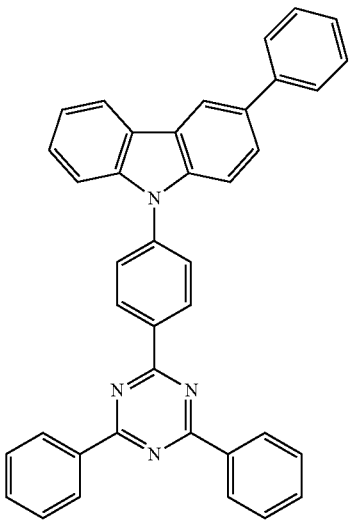
[1-64]
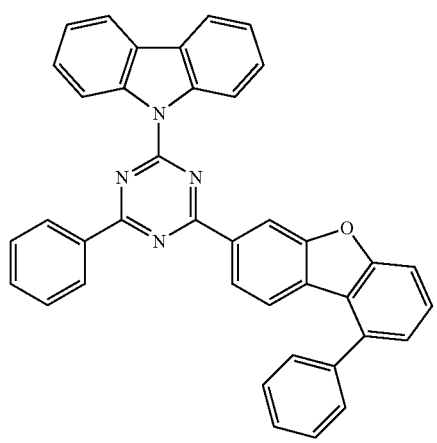
[1-67]
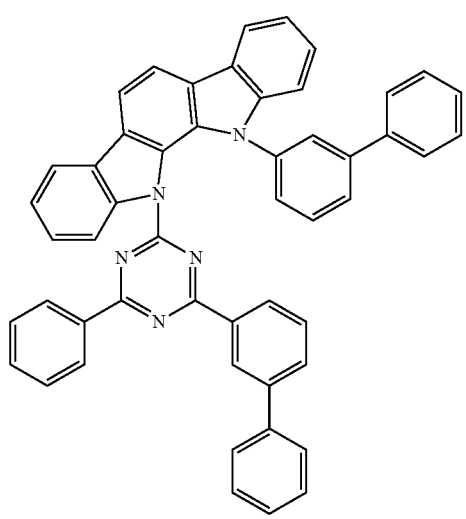
[1-65]
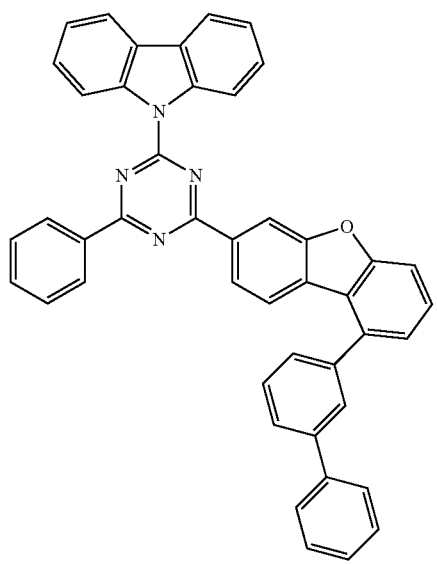
The second compound and the third compound (having hole characteristics) may be different compounds from one another, e.g., may independently be represented by, e.g., Chemical Formula II or Chemical Formula III.
[Chemical Formula II]
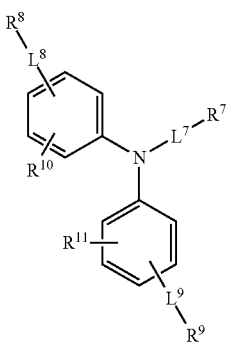
In Chemical Formula II,
L$^7$ to L$^9$ may each independently be, e.g., a single bond, a substituted or unsubstituted C6 to C20 arylene group, a substituted or unsubstituted C2 to C20 heterocyclic group, or a combination thereof, and $R^7$ to $R^{11}$ may each independently be, e.g., hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

$R^8$ to $R^{11}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring.

[Chemical Formula III]

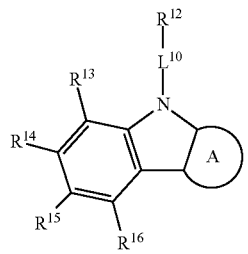

In Chemical Formula III, $L^{10}$ may be, e.g., a single bond, a substituted or unsubstituted C6 to C20 arylene group, a substituted or unsubstituted C2 to C20 heterocyclic group, or a combination thereof, and $R^{12}$ to $R^{16}$ may each independently be, e.g., hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

$R^{12}$ to $R^{16}$ may be separate or adjacent groups thereof are linked with each other to form a substituted or unsubstituted aromatic monocyclic or polycyclic ring.

A may be, e.g., a moiety represented by one of Chemical Formulae A-1 to A-7,

[Chemical Formula A-1]

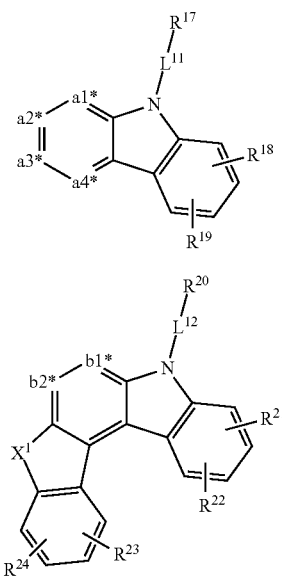

[Chemical Formula A-2]

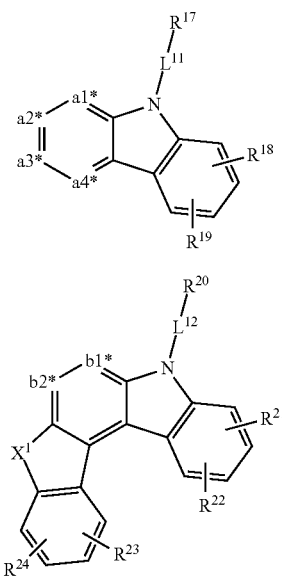

[Chemical Formula A-3]

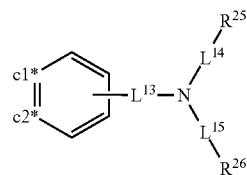

[Chemical Formula A-4]

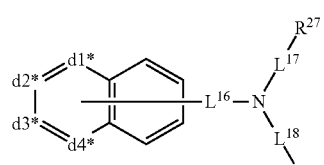

[Chemical Formula A-5]

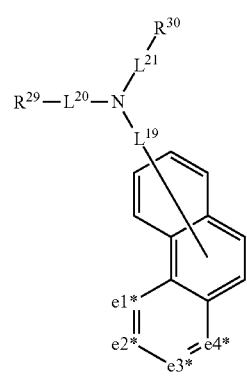

[Chemical Formula A-6]

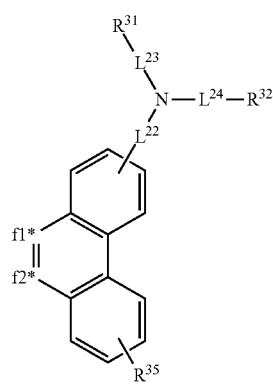

[Chemical Formula A-7]

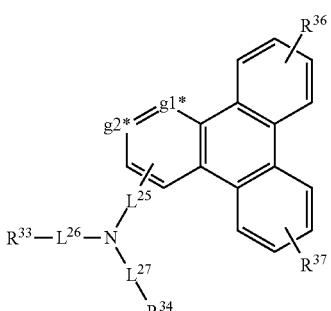

In Chemical Formulae A-1 to A-7, $X^1$ may be, e.g., O, S, or $NR^a$, a1* to a4* may each independently be, e.g., a linking C or $C\text{-}L^a\text{-}R^b$, in which adjacent two of a1* to a4* are linking C and the remaining two are $C\text{-}L^a\text{-}R^b$, d1* to d4* may each independently be, e.g., a linking C or $C\text{-}L^b\text{-}R^c$, in which adjacent two of d1* to d4* are linking C and the remaining two are $C\text{-}L^b\text{-}R^c$, e1* to e4* may each independently be, e.g., a linking C or C-L$^c$-R$^d$, in which adjacent two of e1* to e4* are linking C and the remaining two are C-L$^c$-R$^d$, b1* and b2*, c1* and c2*, f1* and f2* and g1* and *g2 are each a linking C, L$^a$, L$^b$, L$^c$, and L$^{11}$ to L$^{27}$ may each independently be, e.g., a single bond, a substituted or unsubstituted C6 to C20 arylene group, a substituted or unsubstituted C2 to C20 heterocyclic group, or a combination thereof, and R$^a$, R$^b$, R$^c$, R$^d$, and R$^{17}$ to R$^{37}$ may each independently be, e.g., hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

Chemical Formula II may include a substituted amine group as an aryl group or heteroaryl group when R$^{10}$ and R$^{11}$ are separate.

In an implementation, Chemical Formula II may include a substituted or unsubstituted carbazolyl group or a substituted or unsubstituted acridinyl group when R$^{10}$ and R$^{11}$ are linked.

For example, the compound may be represented by one of Chemical Formula II-1 to II-7.

[Chemical Formula II-1]

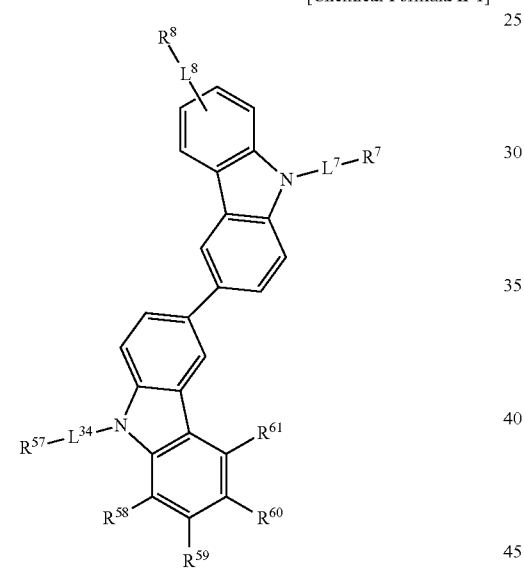

[Chemical Formula II-2]

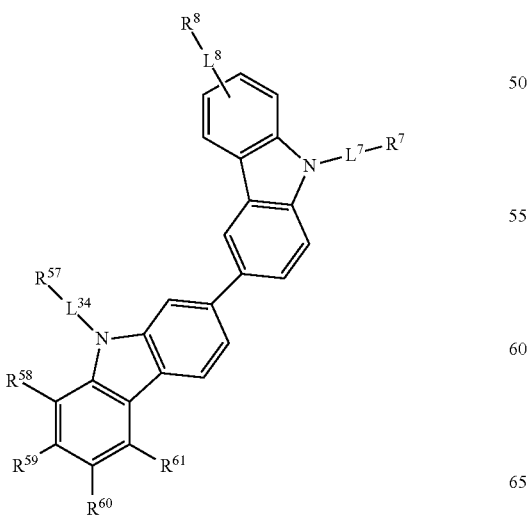

[Chemical Formula II-3]

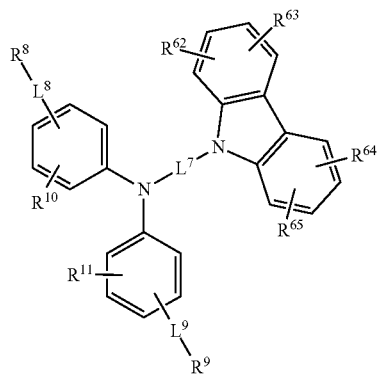

[Chemical Formula II-4]

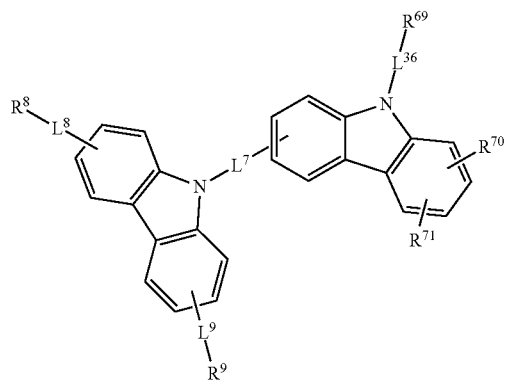

[Chemical Formula II-5]

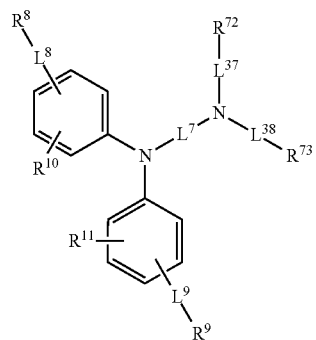

[Chemical Formula II-6]

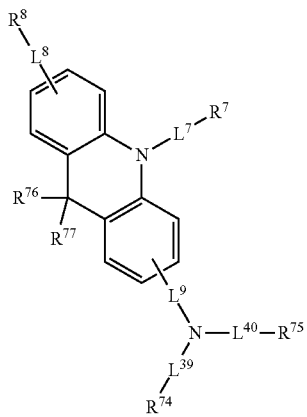

-continued

[Chemical Formula II-7]

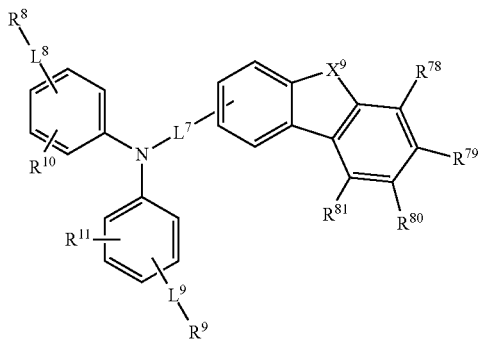

In Chemical Formulae II-1 to II-7, $L^7$ to $L^9$, $R^7$ to $R^{11}$ may be the same as described above, $X^9$ may be, e.g., O, S, or $CR^qR^r$, $L^{34}$ to $L^{40}$ may each independently be, e.g., a single bond, a substituted or unsubstituted C6 to C20 arylene group, a substituted or unsubstituted C2 to C20 heterocyclic group, or a combination thereof, and $R^q$, $R^r$, and $R^{57}$ to $R^{81}$ may each independently be, e.g., hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

$R^8$ and $R^{10}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^9$ and $R^{11}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^q$ and $R^r$ may be separate or adjacent groups thereof are linked with each other to form a substituted or unsubstituted aromatic monocyclic or polycyclic ring, $R^{58}$ to $R^{61}$ may be separate or adjacent groups thereof are linked with each other to form a substituted or unsubstituted aromatic monocyclic or polycyclic ring, and $R^{78}$ to $R^{81}$ may be separate or adjacent groups thereof are linked with each other to form a substituted or unsubstituted aromatic monocyclic or polycyclic ring.

For example, the second compound and the third compound may independently be represented by Chemical Formula II-1 or II-2.

In Chemical Formulae II-1 and II-2, $L^7$, $L^8$, and $L^{34}$ may each independently be, e.g., a single bond or C6 to C12 arylene group, $R^7$ and $R^{57}$ may each independently be, e.g., a substituted or unsubstituted C6 to C18 aryl group, a substituted or unsubstituted carbazolyl group, a substituted or unsubstituted dibenzofuranyl group, or a substituted or unsubstituted dibenzothiophenyl group, and $R^8$ and $R^{58}$ to $R^{61}$ may each independently be, e.g., hydrogen, deuterium, a cyano group, a C1 to C10 alkyl group, a C6 to C12 aryl group, or a carbazolyl group.

In an implementation, $R^7$ and $R^{57}$ of Chemical Formulae II-1 and II-2 may each independently be, e.g., a substituted or unsubstituted phenyl group, a substituted or unsubstituted biphenyl group, a substituted or unsubstituted naphthyl group, a substituted or unsubstituted fluorenyl group, a substituted or unsubstituted carbazolyl group, a substituted or unsubstituted dibenzofuranyl group, or a substituted or unsubstituted dibenzothiophenyl group, and when substituted, the substituent may be a phenyl group, a naphthyl group, or a cyano group.

For example, the second compound and the third compound may independently be represented by Chemical Formula II-3.

In Chemical Formula II-3, $L^7$ to $L^9$ may each independently be, e.g., a single bond, a phenylene group, or a biphenylene group, $R^8$ to $R^{11}$ may each independently be, e.g., a C6 to C12 aryl group and $R^{62}$ to $R^{65}$ may each independently be, e.g., hydrogen, or a C6 to C12 aryl group.

In an implementation, $R^{62}$ to $R^{65}$ of Chemical Formula II-3 may be, e.g., all hydrogen or at least one thereof may be a phenyl group.

For example, the second compound and the third compound may be each represented by Chemical Formula II-4.

In Chemical Formula II-4, $L^7$ to $L^9$ and $L^{36}$ may may each independently be, e.g., a single bond, a phenylene group, or a carbazolylene group, and $R^8$, $R^9$, and $R^{69}$ to $R^{71}$ may each independently be, e.g., hydrogen, or a C6 to C12 aryl group.

In an implementation, $R^8$, $R^9$, and $R^{69}$ to $R^{71}$ of Chemical Formula II-4 may be, e.g., all hydrogen or at least one thereof may be a phenyl group.

For example, the second compound and the third compound may be each represented by Chemical Formula II-5.

In Chemical Formula II-5, $L^7$ may be, e.g., a substituted or unsubstituted C6 to C12 arylene group, $L^8$, $L^9$, $L^{37}$, and $L^{38}$ may each independently be, e.g., a single bond or a C6 to C12 arylene group, and $R^8$ to $R^{11}$, $R^{72}$, and $R^{73}$ may each independently be, e.g., a C6 to C20 aryl group.

For example, $L^7$ of Chemical Formula II-5 may be further substituted with a C6 to C12 aryl group or a C6 to C20 arylamine group and $R^8$ to $R^{11}$, $R^{72}$, and $R^{73}$ may independently be a phenyl group, a biphenyl group, a terphenyl group, or a triphenylene group.

For example, the second compound and the third compound may be each represented by Chemical Formula II-6.

In Chemical Formula II-6, $L^7$ to $L^9$, $L^{39}$, and $L^{40}$ may each independently be, e.g., a single bond or a C6 to C12 arylene group, $R^8$ may be, e.g., hydrogen or a phenyl group, $R^7$, $R^{74}$, and $R^{75}$ may each independently be, e.g., a C6 to C20 aryl group, and $R^{76}$ and $R^{77}$ may each independently be, e.g., a C1 to C10 alkyl group or a C6 to C12 aryl group.

For example, the second compound and the third compound may be each represented by Chemical Formula II-7.

In Chemical Formula II-7, $L^7$ to $L^9$ may each independently be, e.g., a single bond or C6 to C12 arylene group, $X^9$ may be, e.g., O, S, or $CR^qR^r$, $R^q$, $R^r$, and $R^{78}$ to $R^{81}$ may each independently be, e.g., hydrogen, a C1 to C10 alkyl group, or a C6 to C12 aryl group, and $R^8$ to $R^{11}$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted triphenylene group, a substituted or unsubstituted dibenzofuranyl group, a substituted or unsubstituted thiophenyl group, a substituted or unsubstituted fused dibenzofuranyl group, or a substituted or unsubstituted fused dibenzothiophenyl group.

For example, in Chemical Formula II-7, $R^8$ and $R^{10}$ and $R^9$ and $R^{11}$ may be separate or adjacent groups thereof may be linked with each other to form a substituted or unsubstituted fluorenyl group, a substituted or unsubstituted triphenylene group, a substituted or unsubstituted fused dibenzofuranyl group, or a substituted or unsubstituted fused dibenzothiophenyl group along with the phenyl groups substituted with $R^8$ and $R^{10}$ and $R^9$ and $R^{11}$.

Chemical Formula III may be represented by one of Chemical Formulae III-1 to III-24 according to specific forms and fusion positions of the moiety represented by A.

[Chemical Formula III-1]

[Chemical Formula III-2]

[Chemical Formula III-3]

[Chemical Formula III-4]

[Chemical Formula III-5]

[Chemical Formula III-6]

[Chemical Formula III-7]

[Chemical Formula III-8]

[Chemical Formula III-9]

[Chemical Formula III-10]
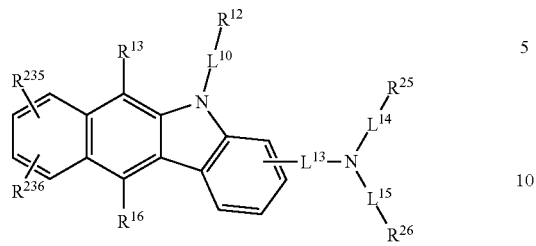
[Chemical Formula III-11]
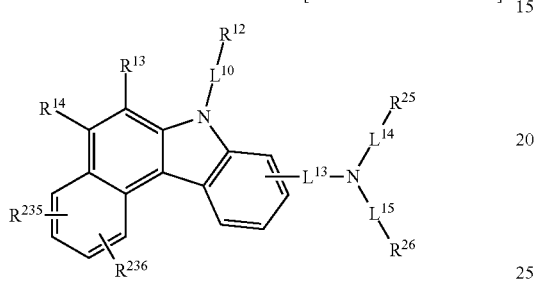
[Chemical Formula III-12]
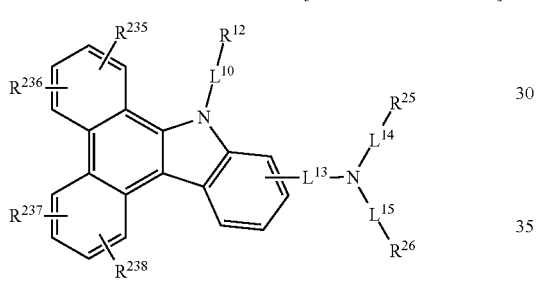
[Chemical Formula III-13]
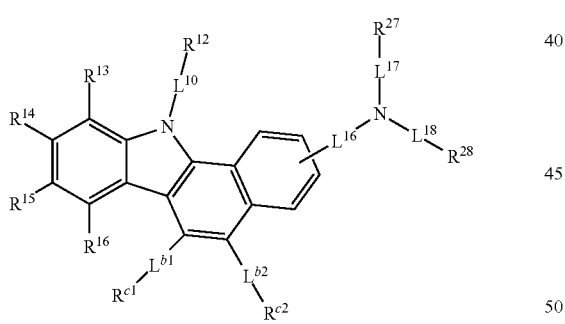
[Chemical Formula III-14]
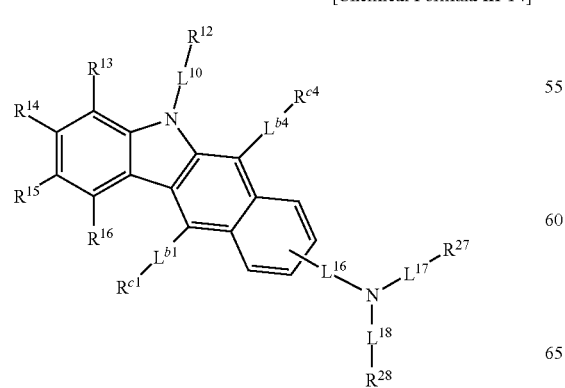
[Chemical Formula III-15]
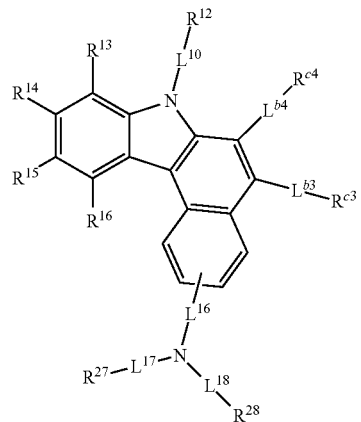
[Chemical Formula III-16]
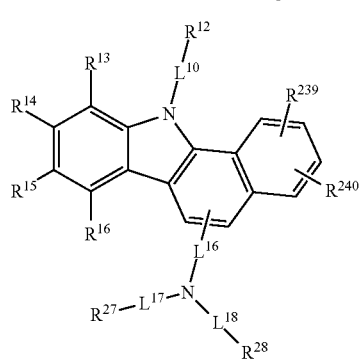
[Chemical Formula III-17]
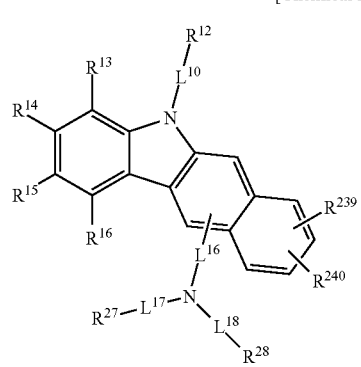
[Chemical Formula III-18]
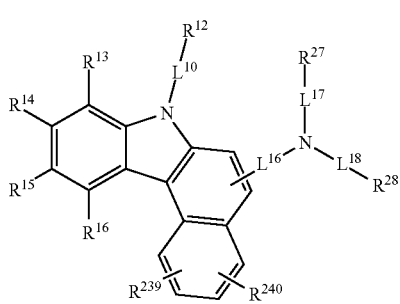

[Chemical Formula III-19]

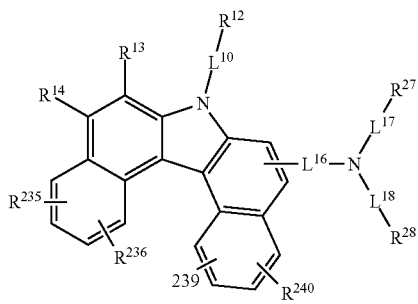

[Chemical Formula III-20]

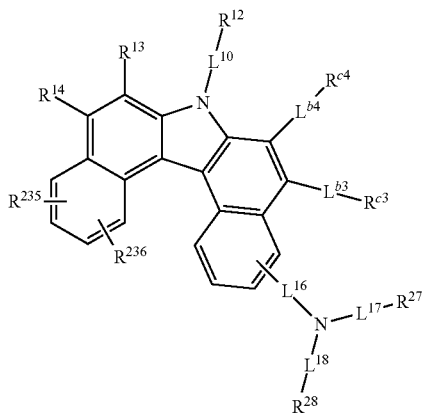

[Chemical Formula III-21]

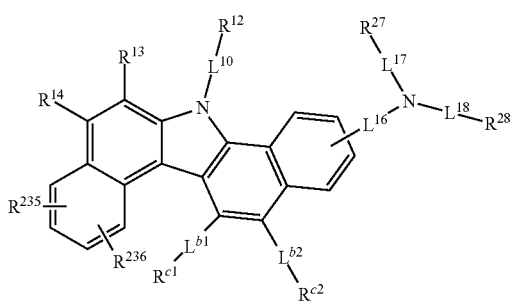

[Chemical Formula III-22]

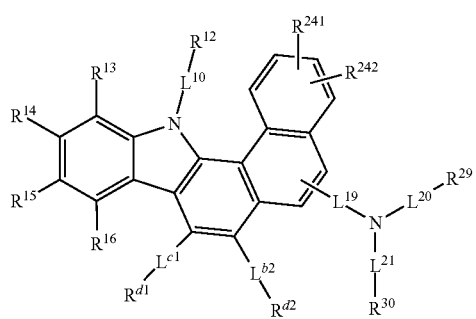

[Chemical Formula III-23]

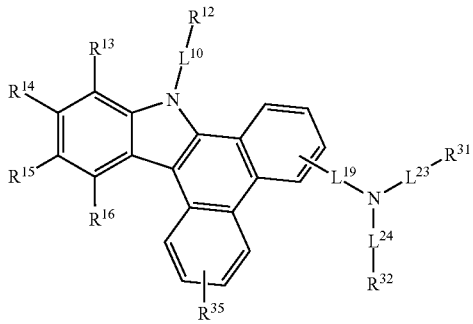

[Chemical Formula III-24]

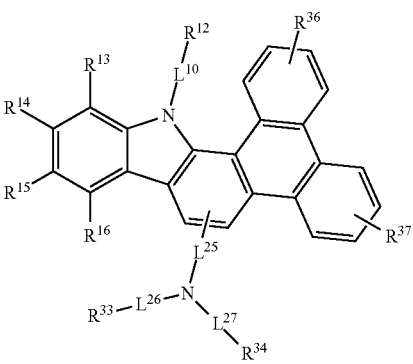

In Chemical Formulae III-1 to III-24, $X^1$, $L^{10}$ to $L^{27}$, $R^{12}$ to $R^{22}$, and $R^{25}$ to $R^{37}$ are the same as described above, $L^{a1}$ to $L^{a4}$ may each independently be, e.g., a single bond, a substituted or unsubstituted C6 to C20 arylene group, a substituted or unsubstituted C2 to C20 heterocyclic group, or a combination thereof, $R^{b1}$ to $R^{b4}$ may each independently be, e.g., hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{235}$ to $R^{242}$ may each independently be, e.g., hydrogen, deuterium, a substituted or unsubstituted C1 to C10 alkyl group, a substituted or unsubstituted C6 to C20 aryl group, a halogen, a cyano group, or a combination thereof.

For example, the second compound and the third compound may be each represented by one of Chemical Formulae III-1 to III-5.

In Chemical Formulae III-1 to III-5, $L^{10}$, $L^{11}$, and $L^{a1}$ to $L^{a4}$ may each independently be, e.g., a single bond, a C6 to C12 arylene group, or a carbazolylene group, $R^{12}$, $R^{17}$ and $R^{b1}$ to $R^{b4}$ may each independently be, e.g., a substituted or unsubstituted phenyl group, a substituted or unsubstituted biphenyl group, a substituted or unsubstituted terphenyl group, a substituted or unsubstituted fluorenyl group, a substituted or unsubstituted triphenylene group, a substituted or unsubstituted dibenzofuranyl group, a substituted or unsubstituted dibenzothiophenyl group, a substituted or unsubstituted carbazolyl group, or a C6 to C12 arylamine group, and $R^{13}$ to $R^{16}$, $R^{18}$ and $R^{19}$ may independently be hydrogen, a C6 to C12 aryl group, or a C6 to C12 arylamine group.

For example, in Chemical Formulae III-1 to III-5, $L^{a1}$ to $L^{a4}$ may be all single bonds, $R^{b1}$ to $R^{b4}$ may be all hydrogen, and $R^{13}$ to $R^{16}$, $R^{18}$, and $R^{19}$ may be all hydrogen or at least one thereof may be a C6 to C12 aryl group or a C6 to C12 arylamine group.

For example, the second compound and the third compound may be each represented by III-6.

For example, in Chemical Formula III-6, $X^1$ may be O, S, or $NR^a$, $R^a$ may be a C6 to C12 aryl group, $L^{10}$ and $L^{12}$ may independently be a single bond or a C6 to C12 arylene group, $R^{12}$ and $R^{20}$ may independently be a substituted or unsubstituted phenyl group, a substituted or unsubstituted biphenyl group, a substituted or unsubstituted terphenyl group, a substituted or unsubstituted fluorenyl group, or a substituted or unsubstituted triphenylene group, and $R^{13}$ to $R^{16}$ and $R^{21}$ to $R^{24}$ may independently be hydrogen or a C6 to C12 aryl group.

For example, in Chemical Formula III-6, $R^{13}$ to $R^{16}$ and $R^{21}$ to $R^{24}$ may be all hydrogen or at least one thereof may be a C6 to C12 aryl group.

For example, the second compound and the third compound may be each represented by one of Chemical Formulae III-7 to III-11.

In Chemical Formulae III-7 to III-12, $L^{10}$ and $L^{13}$ to $L^{15}$ may independently be a single bond or a C6 to C12 arylene group, $R^{25}$ and $R^{26}$ may independently be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted carbazolyl group, a substituted or unsubstituted dibenzofuranyl group, or a substituted or unsubstituted dibenzothiophenyl group, $R^{12}$ may be a C6 to C12 aryl group, $R^{13}$ to $R^{16}$, $R^{235}$ to $R^{238}$, $R^{241}$ and $R^{242}$ may independently be hydrogen, a C6 to C12 aryl group, or a C6 to C12 arylamine group.

For example, in Chemical Formulae III-7 to III-12, $R^{13}$ to $R^{16}$, $R^{235}$ to $R^{238}$, $R^{241}$, and $R^{242}$ may be all hydrogen or at least one thereof may be a C6 to C12 aryl group or a C6 to C12 arylamine group.

For example, the second compound and the third compound may be each represented by one of Chemical Formulae III-13 to III-21.

In Chemical Formulae III-13 to III-21, $L^{10}$, $L^{16}$ to $L^{18}$ and $L^{b1}$ to $L^{b4}$ may independently be a single bond or a C6 to C12 arylene group, $R^{27}$ and $R^{28}$ may independently be a substituted or unsubstituted phenyl group, a substituted or unsubstituted biphenyl group, a substituted or unsubstituted terphenyl group, a substituted or unsubstituted naphthyl group, a substituted or unsubstituted dibenzofuranyl group, or a substituted or unsubstituted dibenzothiophenyl group, $R^{12}$ may be a C6 to C12 aryl group, and $R^{13}$ to $R^{16}$, $R^{c1}$ to $R^{c4}$, $R^{235}$, $R^{236}$, $R^{239}$, and $R^{240}$ may independently be hydrogen or a C6 to C12 aryl group.

For example, in Chemical Formulae III-13 to III-21, $R^{13}$ to $R^{16}$, $R^{c1}$ to $R^{c4}$, $R^{235}$, $R^{236}$, $R^{239}$, and $R^{240}$ may be all hydrogen or at least one thereof may be a C6 to C12 aryl group.

For example, the second compound and the third compound may be each represented by one of Chemical Formulae III-22 to III-24.

In Chemical Formulae III-22 to III-24, $L^{10}$, $L^{19}$ to $L^{27}$, $L^{C1}$, and $L^{C2}$ may independently be a single bond or a C6 to C12 arylene group, $R^{29}$ to $R^{34}$ may independently be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted carbazolyl group, a substituted or unsubstituted dibenzofuranyl group, or a substituted or unsubstituted dibenzothiophenyl group, $R^{12}$ may be a C6 to C12 aryl group, and $R^{13}$ to $R^{16}$, $R^{35}$, $R^{d1}$, and $R^{d2}$ may independently be hydrogen or a C6 to C12 aryl group.

For example, in Chemical Formulae III-22 to III-24, $R^{13}$ to $R^{16}$, $R^{35}$, $R^{d1}$, and $R^{d2}$ may be all hydrogen or at least one thereof may be a C6 to C12 aryl group.

For example, the second compound and the third compound may be each represented by one of Chemical Formula II-1, Chemical Formula II-2, and Chemical Formula III-3.

In an implementation, the second and the third compound may each independently be, e.g., a compound of Group 2.

[Group 2]

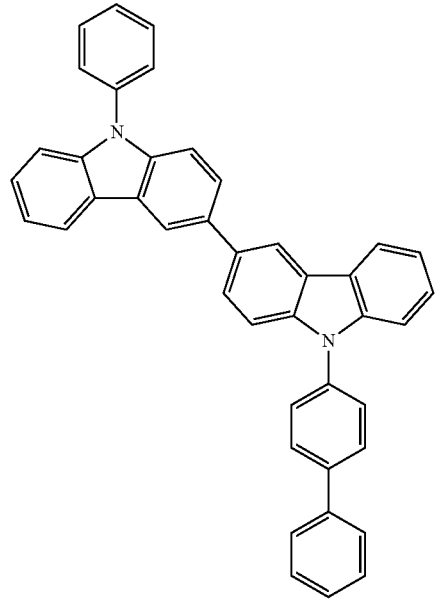

[2-1]

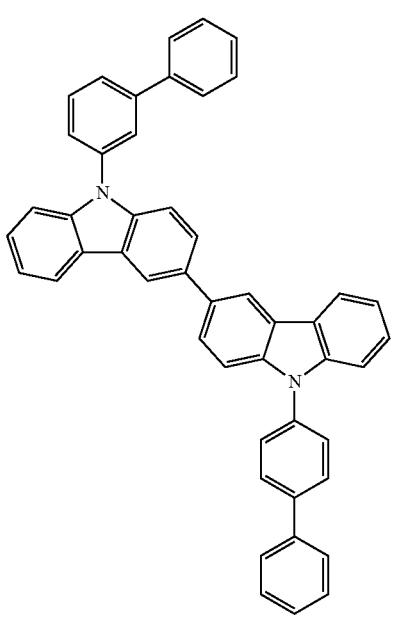

[2-2]

[2-3]
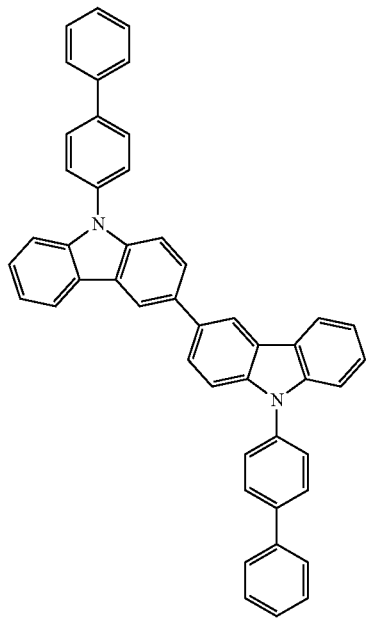
[2-5]
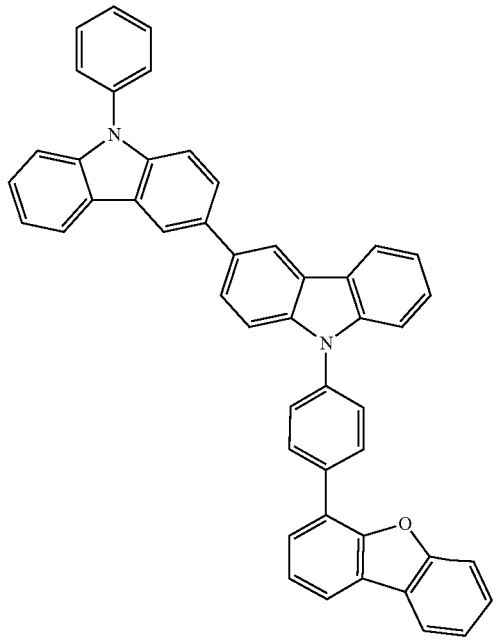
[2-4]
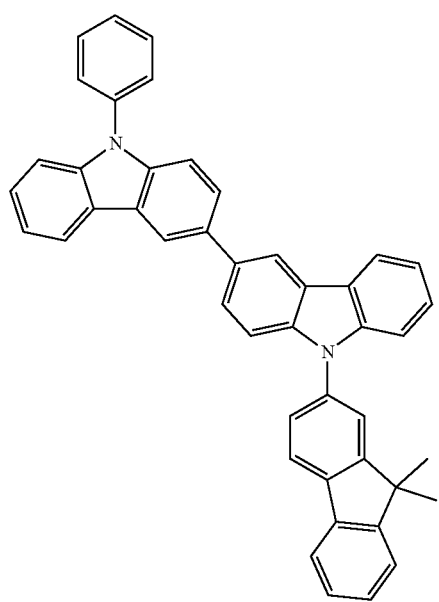
[2-6]

[2-7]
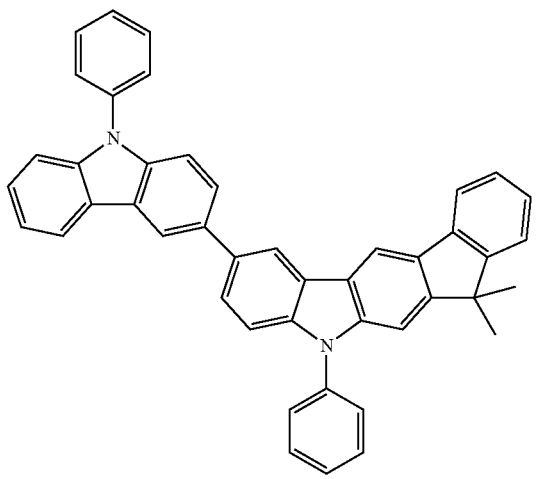
[2-8]
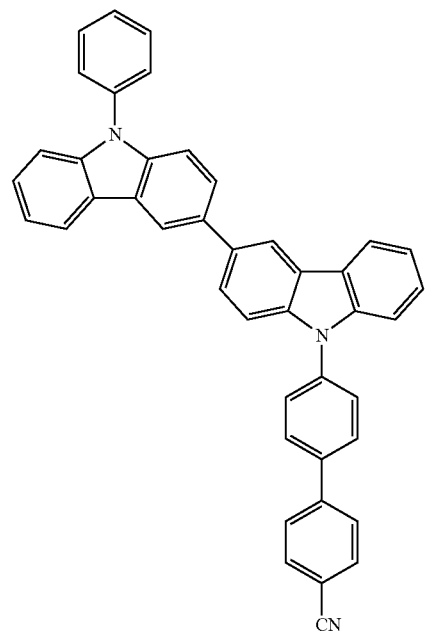
[2-10]
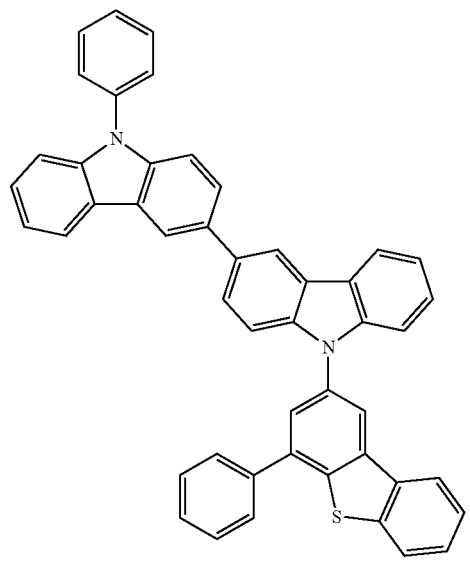
[2-9]
[2-11]
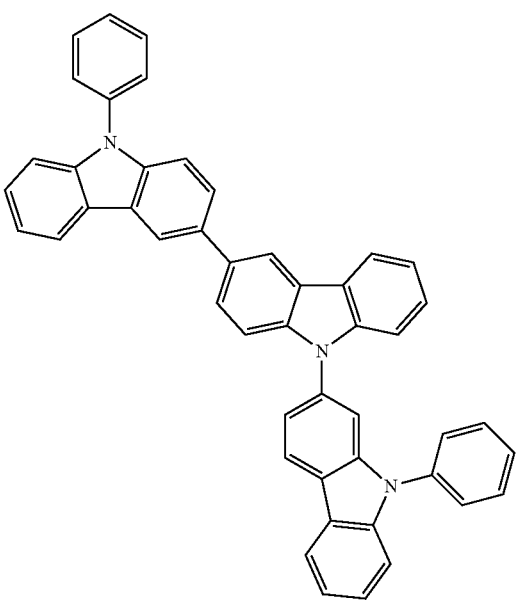

[2-12]
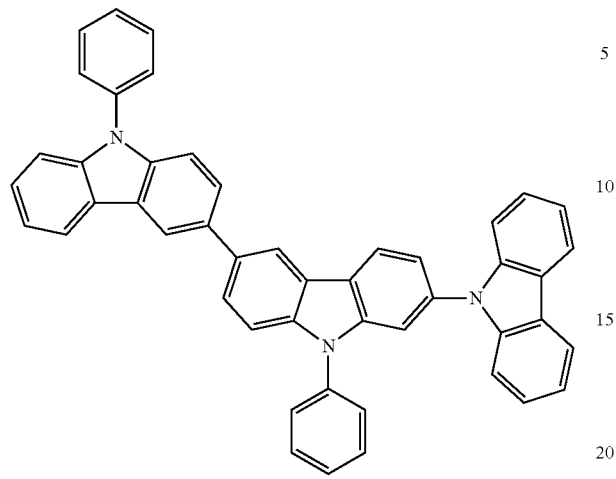
[2-13]
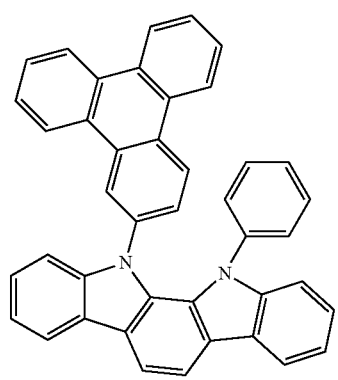
[2-14]
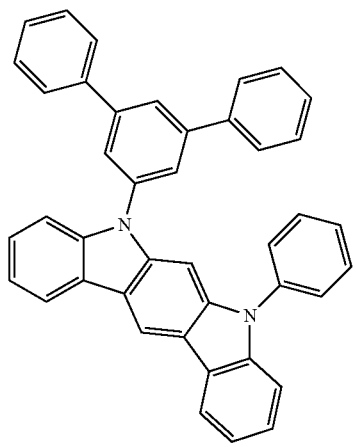
[2-15]
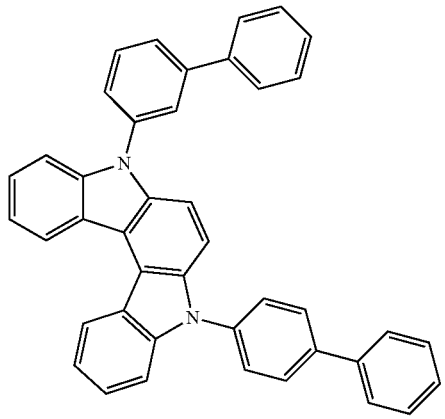
[2-16]
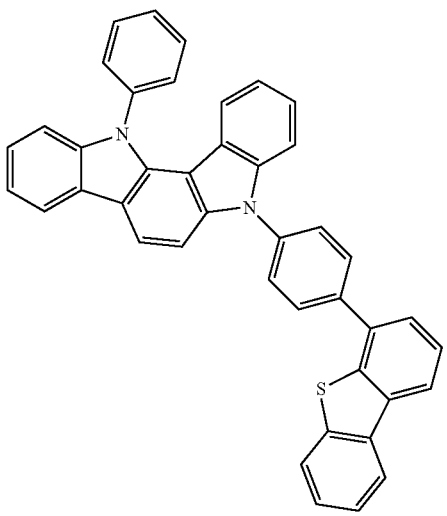
[2-17]
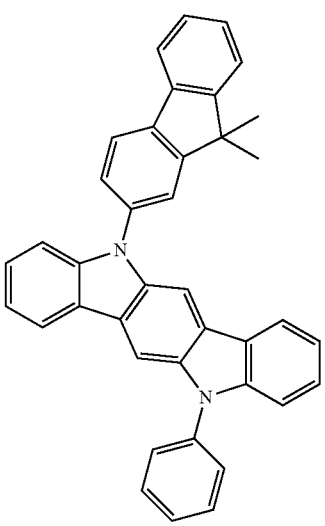

[2-18]
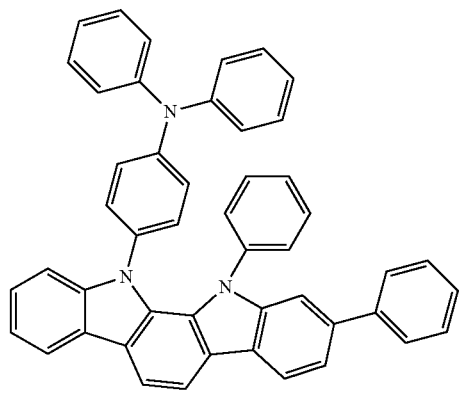
[2-21]
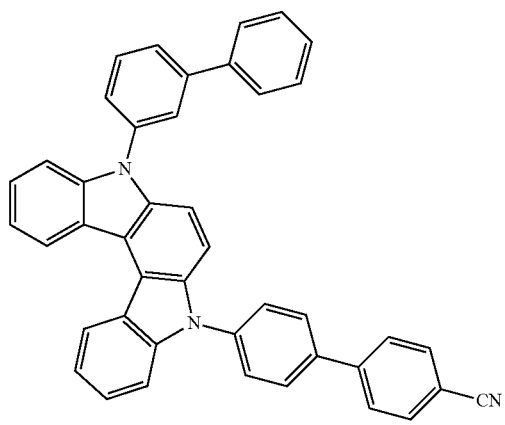
[2-19]
[2-22]
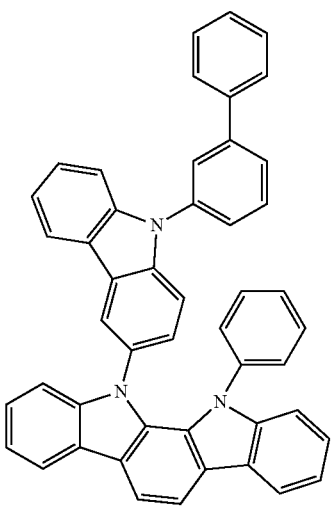
[2-20]
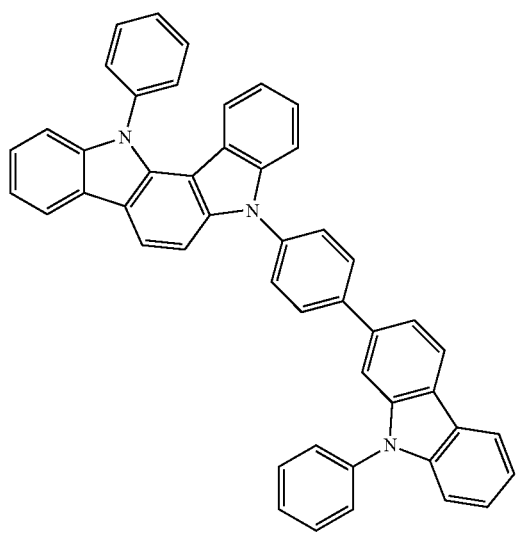
[2-23]
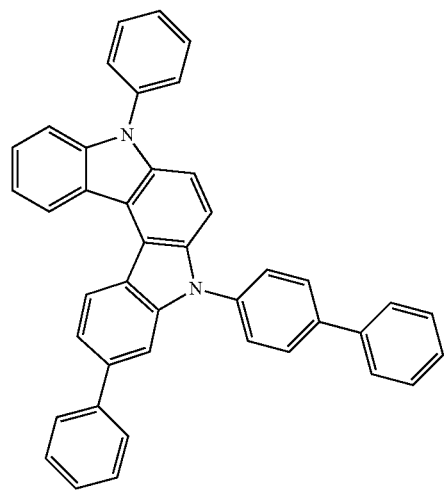

[2-24]
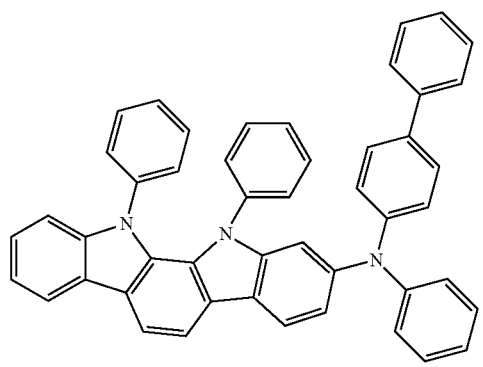
[2-25]
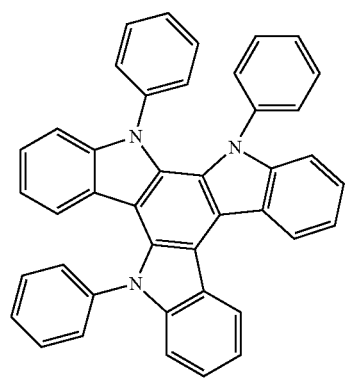
[2-26]
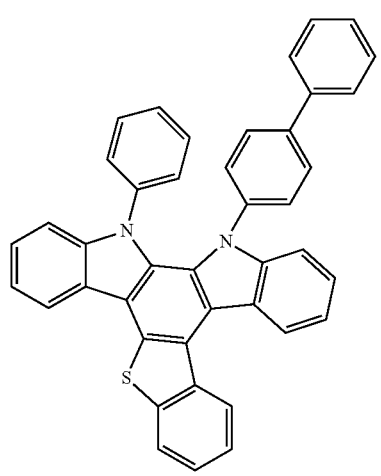
[2-27]
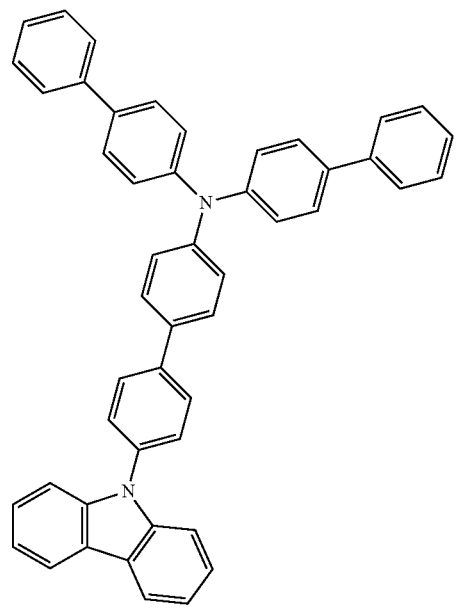
[2-28]
[2-29]
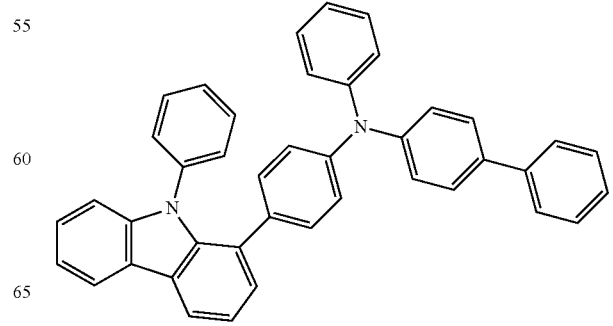

[2-30]
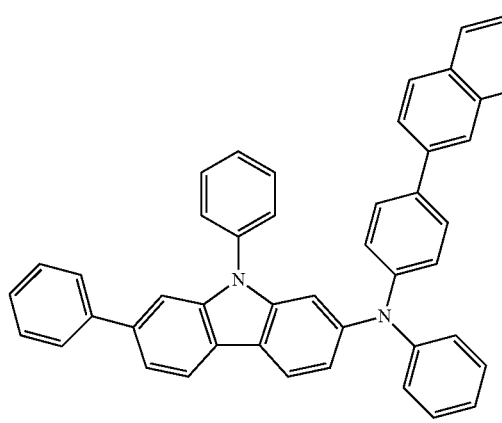
[2-37]
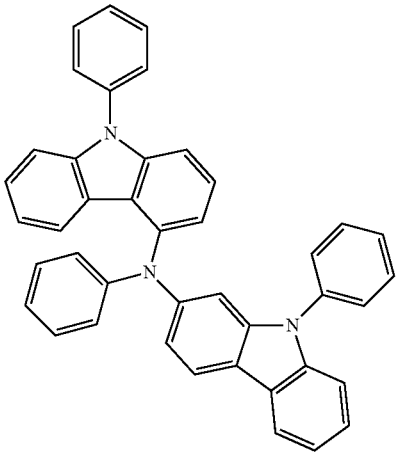
[2-31]
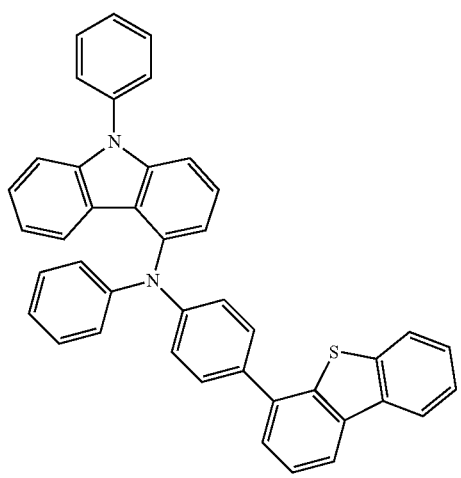
[2-38]
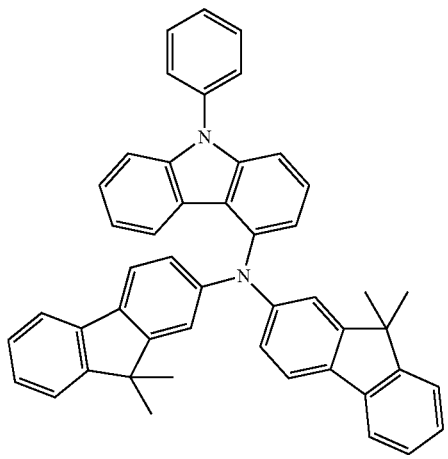
[2-32]
[2-33]
[2-34]
[2-35]
[2-36]
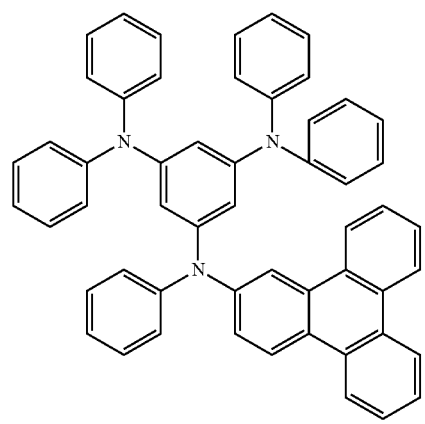
[2-39]
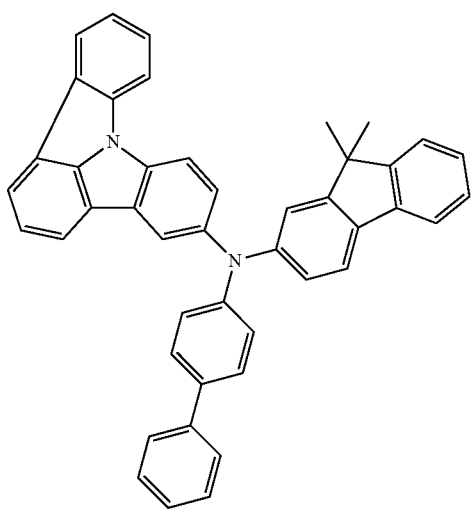

[2-40]
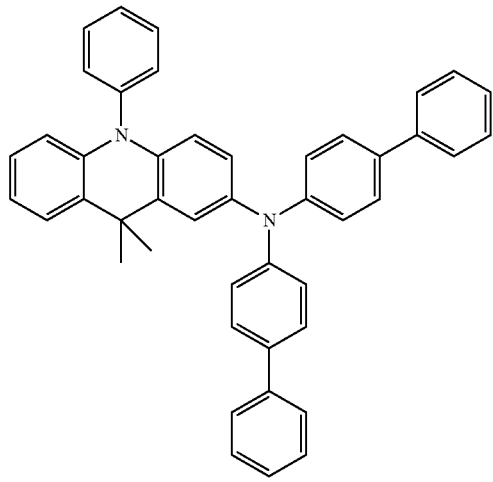
[2-43]
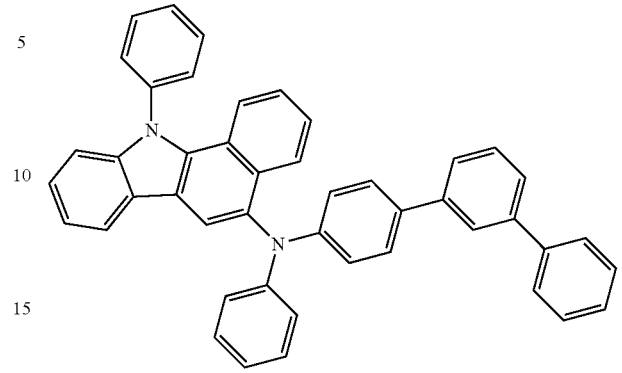
[2-41]
[2-44]
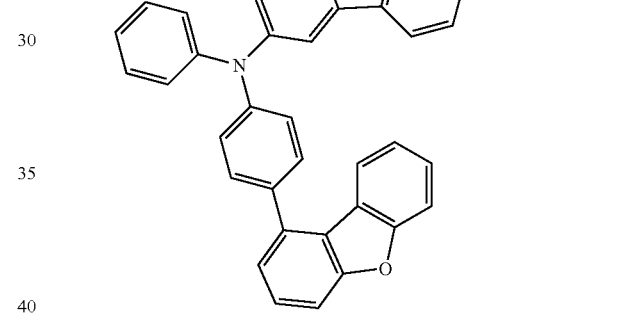
[2-42]
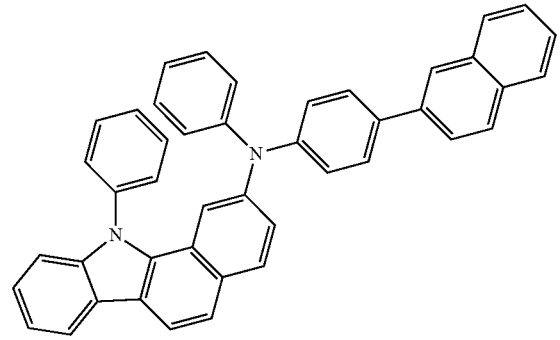
[2-45]
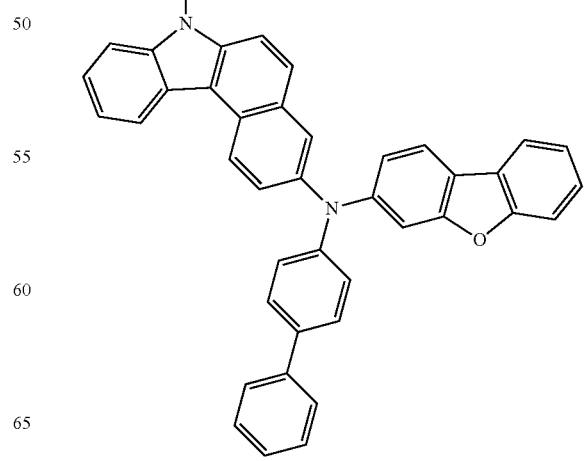

[2-46]
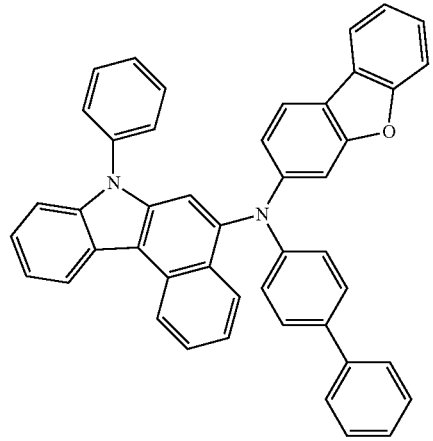
[2-47]
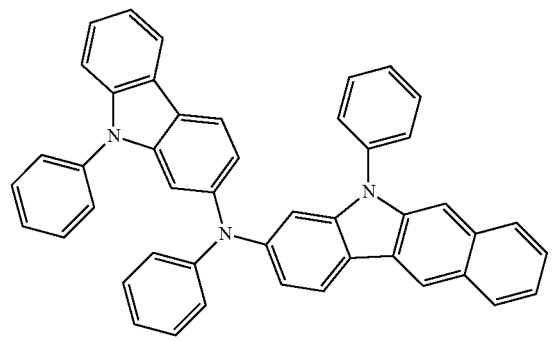
[2-48]
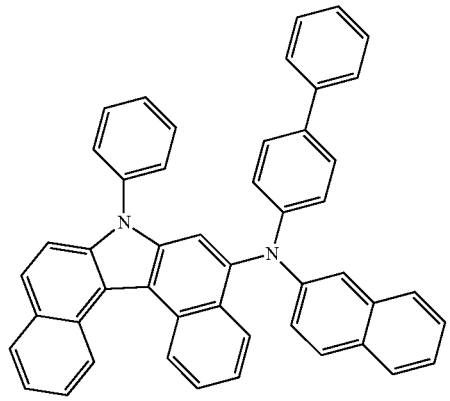
[2-49]
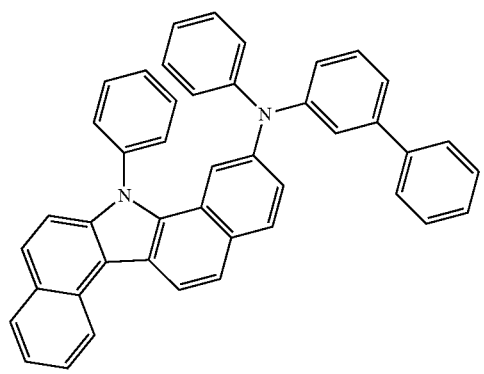
[2-50]
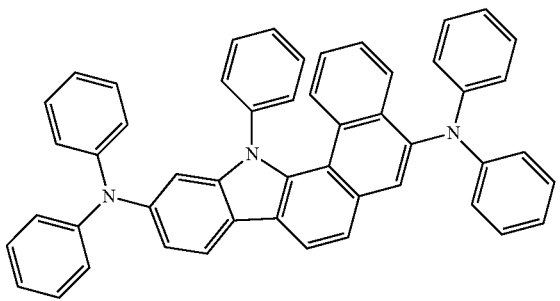
[2-51]
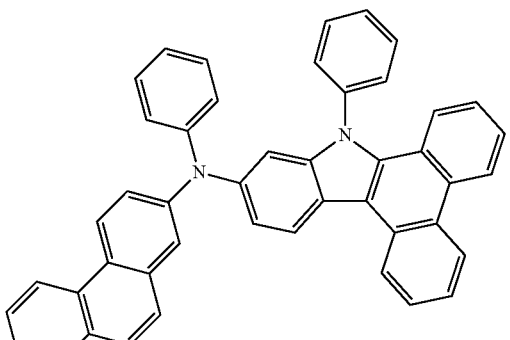
[2-52]
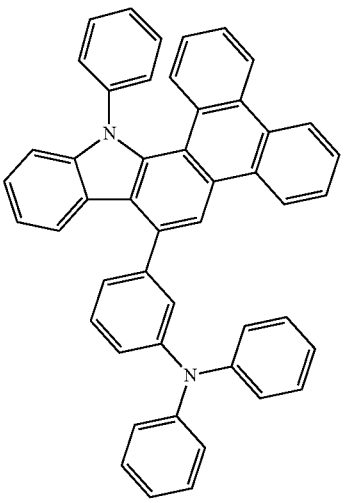
[2-53]
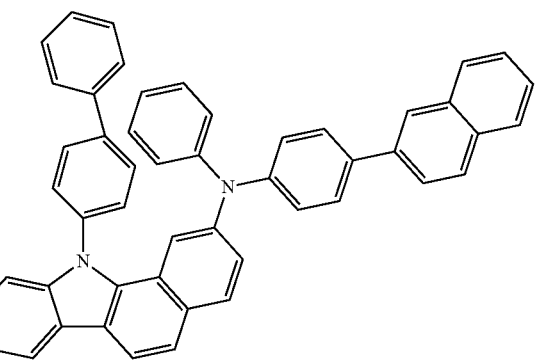

[2-54]
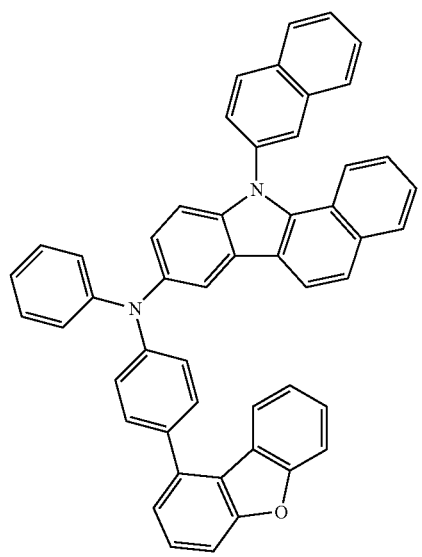
[2-55]
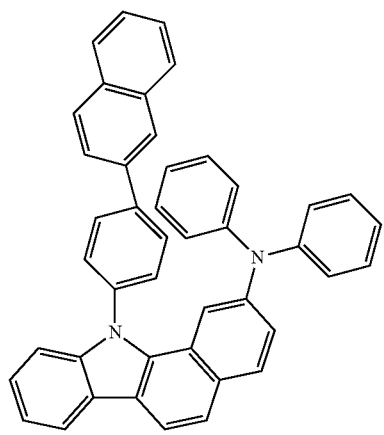
[2-56]
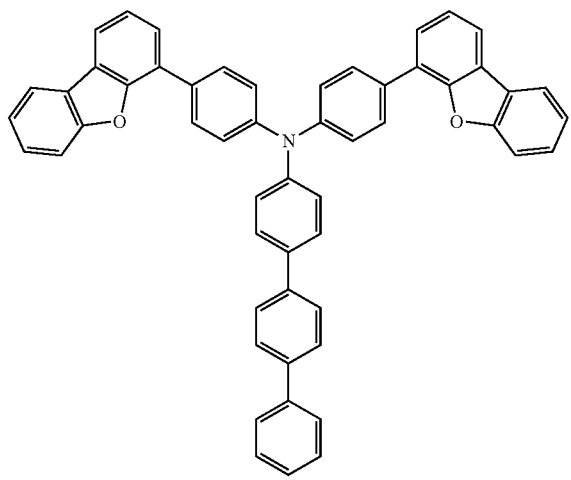
[2-57]
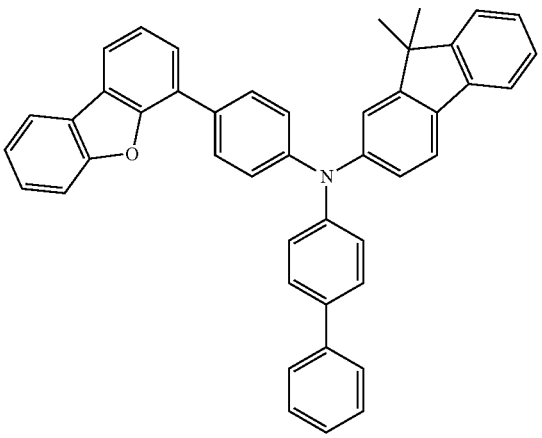
[2-58]
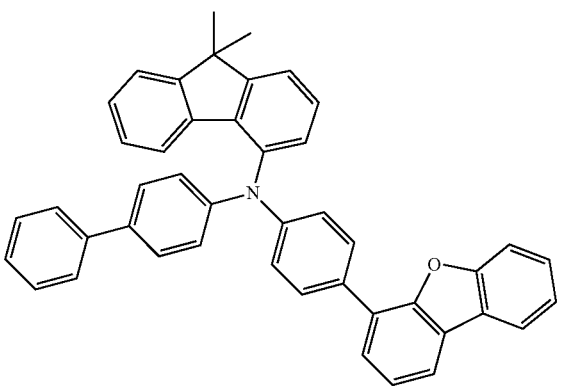
[2-59]
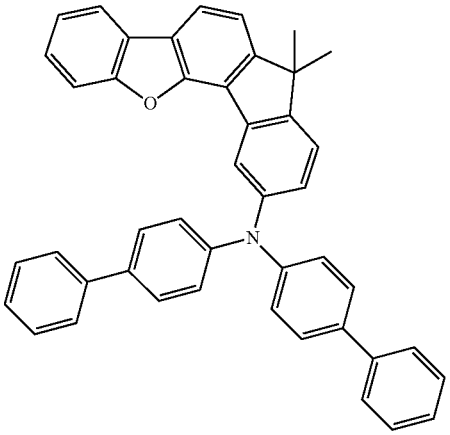

[2-60]
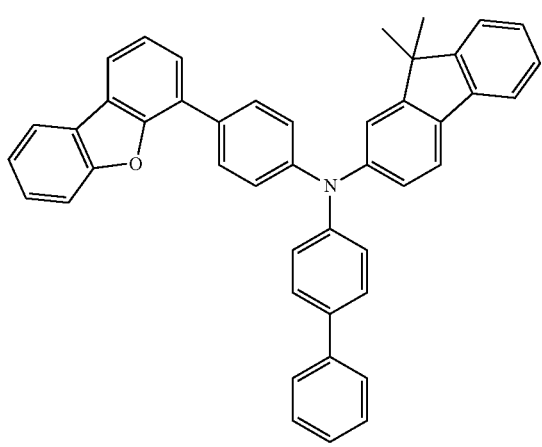
[2-63]
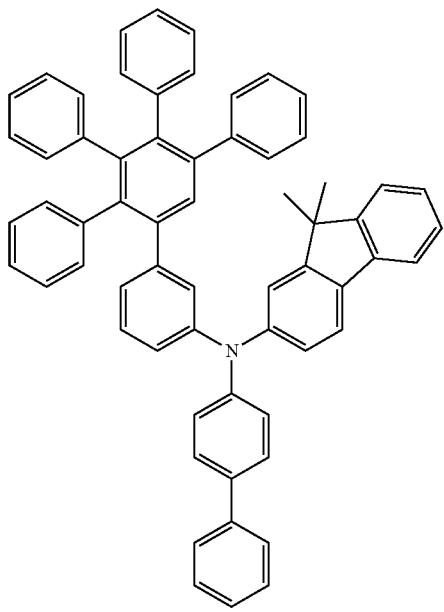
[2-61]
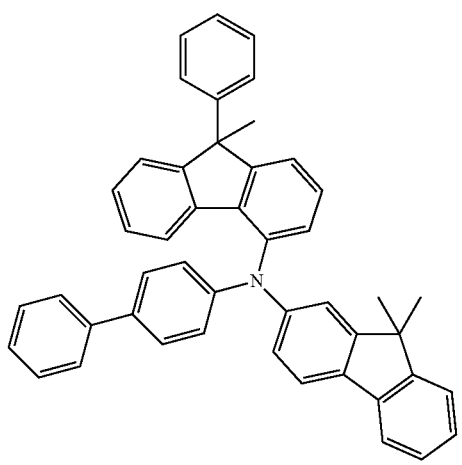
[2-64]
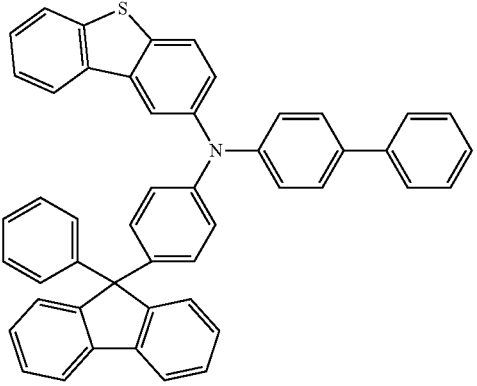
[2-62]
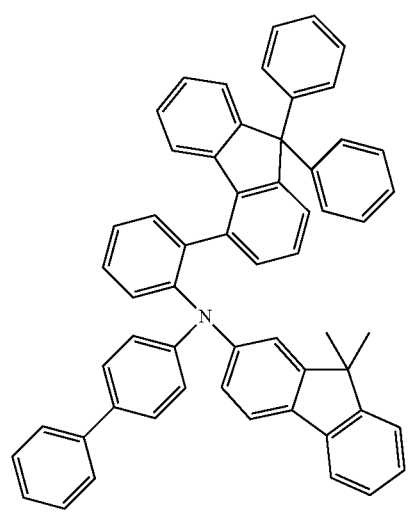
[2-65]
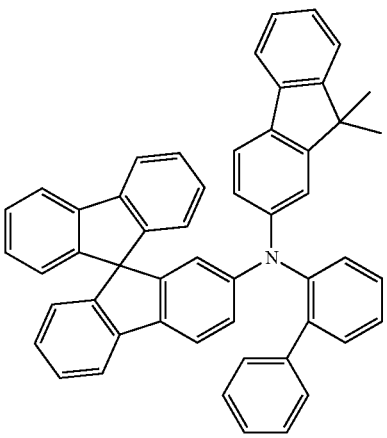

[2-66]
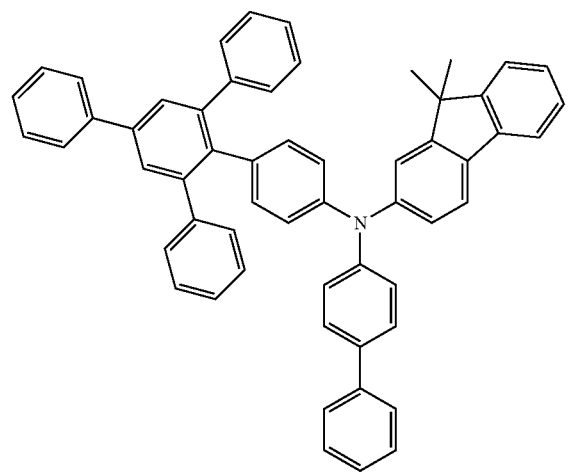
[2-67]
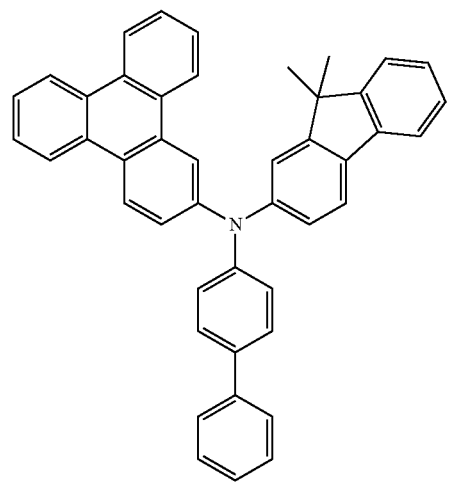
[2-68]
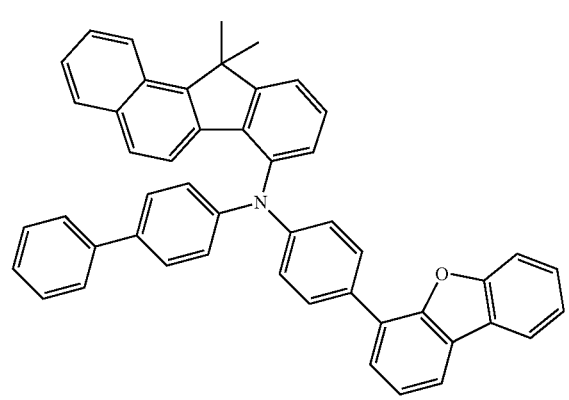
[2-69]
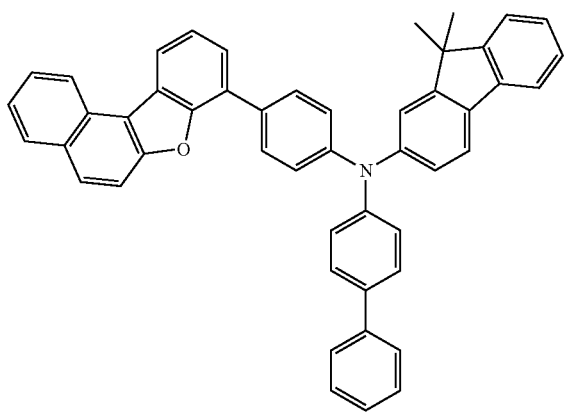
[2-70]
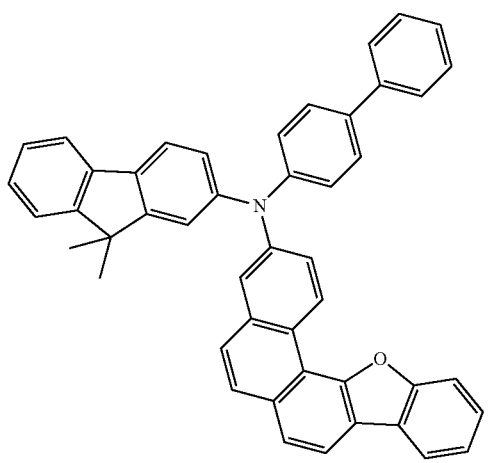
[2-71]
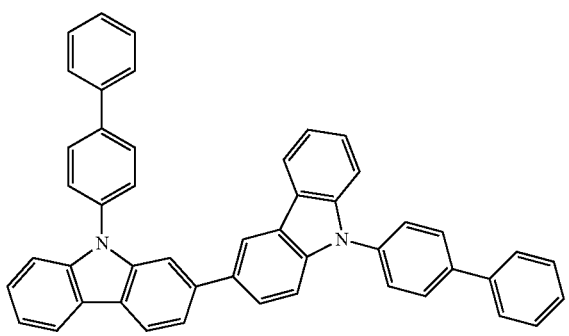
[2-72]
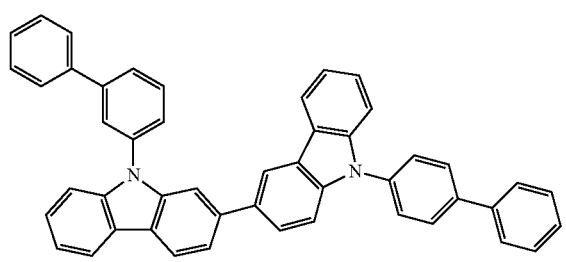

-continued

[2-73]

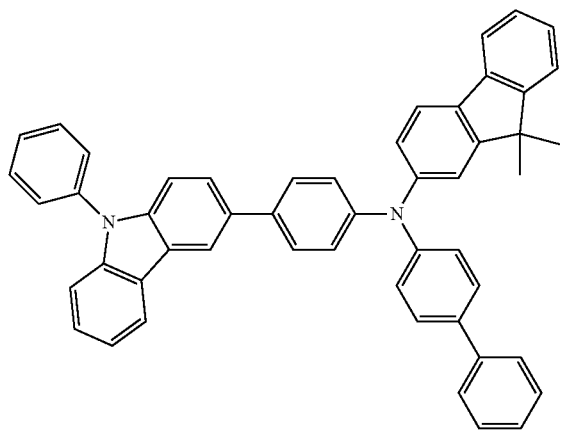

The first compound may include a nitrogen-containing six-membered ring having high electron transport characteristics to transport electrons stably and effectively, lowering a driving voltage, increasing current efficiency, and realizing long life-span characteristics of a device.

The second compound and the third compound may have a structure containing carbazole or amine with high HOMO energy, which effectively injects and delivers holes, contributing to the improvement of device characteristics.

The 3-host composition including the first compound, the second compound, and the third compound may facilitate finally or finely adjusting of electron/hole characteristics within the device stack to allow an optimal balance, and to greatly improve device characteristics due to proper charge balance, compared with 2-host composition, e.g., a composition including the first compound and the second compound or a composition including the first compound and the third compound. In an implementation, the 3-host composition may include a mixture of the first compound, the second compound, and the third compound.

In an implementation, the first compound may be represented by Chemical Formula I-1A-1 or I-1B-1, the second compound may be represented by Chemical Formula II-1 or III-3, and the third compound may be represented by Chemical Formula II-1 or II-2.

For example, the composition of the second compound and the third compound may be a combination of Chemical Formula III-3 and Chemical Formula II-1 or a combination of Chemical Formula II-1 and Chemical Formula II-2, and each compound may be different.

The first compound:the second compound and the third compound (e.g., the weight of the first compound:the total weight of the second and third compounds) may be included, e.g., in a weight ratio of about 1:99 to about 99:1. Within the range, the appropriate weight ratio may be adjusted by using the electron transport capability of the first compound and the hole transport capability of the second compound and the third compound and thus bipolar characteristics may be realized and efficiency and life-span may be improved. Within the range, they may be, e.g., included in a weight ratio of about 10:90 to about 90:10, about 20:80 to about 80:20, about 30:70 to about 70:30, about 30:70 to about 60:40, or about 30:70 to about 50:50. For example, they may be included in a weight ratio of about 30:70.

In an implementation, the second compound and the third compound may be included in a weight ratio of, e.g., about 1:9 to about 9:1 or about 1:9 to about 8:2. For example, it may be included in a weight ratio of about 1:9 to about 7:3 or a weight ratio of about 1:9 to about 5:5. Within the range, electron injection and transport characteristics are enhanced compared with a single host or a 2-host.

The composition for the organic optoelectronic device may further include one or more compounds in addition to the aforementioned first compound, the second compound, and the third compound.

The composition for the organic optoelectronic device may further include a dopant. The dopant may be, e.g., a phosphorescent dopant. For example the dopant may be a red, green, or blue phosphorescent dopant, and may be for example a red phosphorescent dopant.

The dopant is a material mixed with the composition for the organic optoelectronic device including the first compound, the second compound, and the third compound in a small amount to cause light emission and generally a material such as a metal complex that emits light by multiple excitation into a triplet or more. The dopant may be, e.g., an inorganic, organic, or organic/inorganic compound, and one or more types thereof may be used.

Examples of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$$L^A M X^A$$ [Chemical Formula Z]

In Chemical Formula Z, M is a metal, and $L^A$ and $X^A$ may be the same or different and are a ligand to form a complex compound with M.

The M may be e.g., Ir, Pt, Os, Ti, Zr, Hf, Eu, Tb, Tm, Fe, Co, Ni, Ru, Rh, Pd, or a combination thereof and $L^A$ and $X^A$ may be, e.g., a bidendate ligand.

$L^A$ and $X^A$ may each independently be a ligand of Group D.

[Group D]

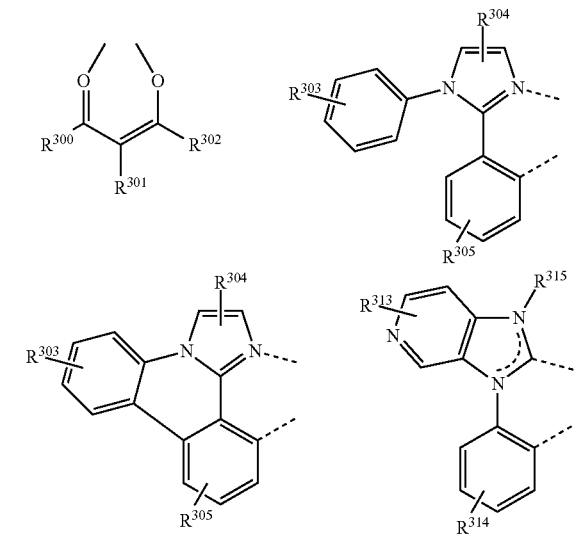

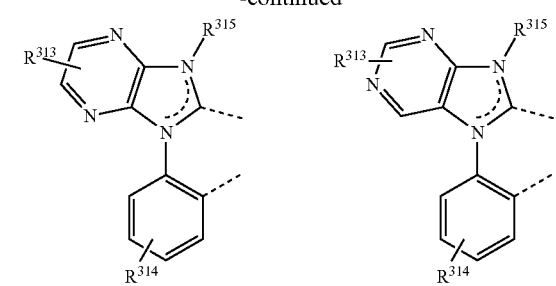
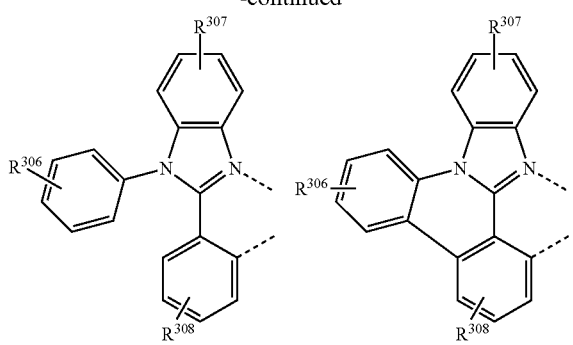
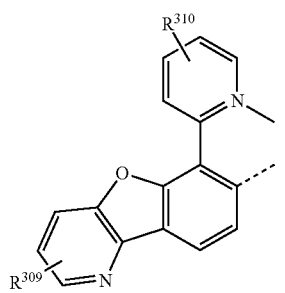
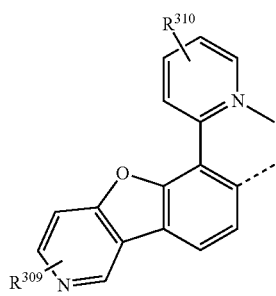
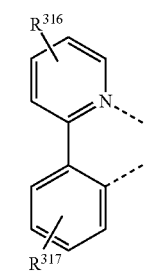
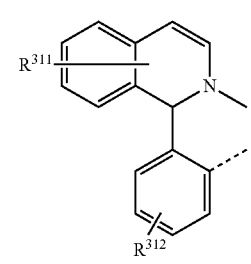
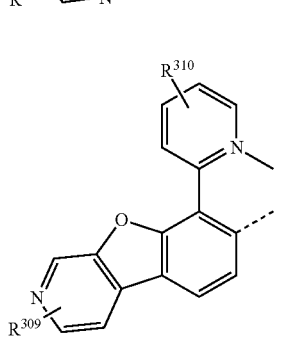
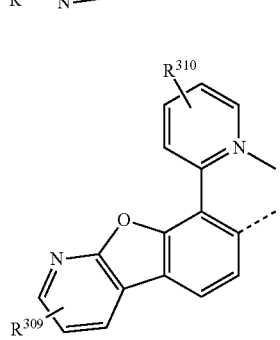
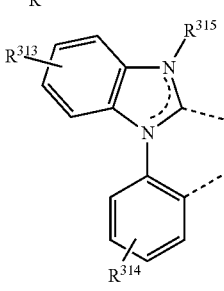
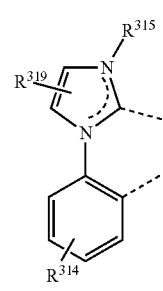
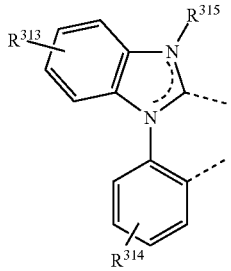
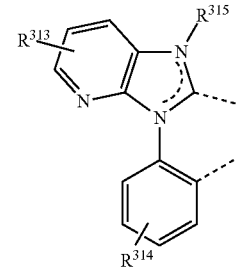
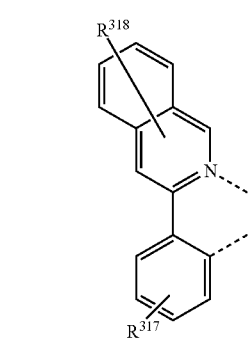
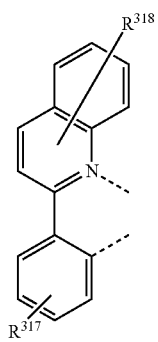
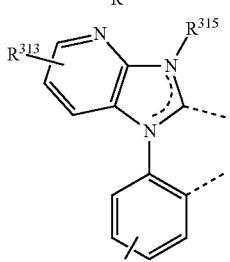
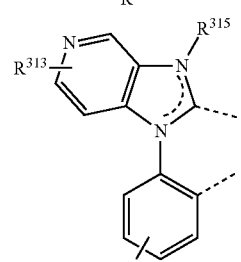
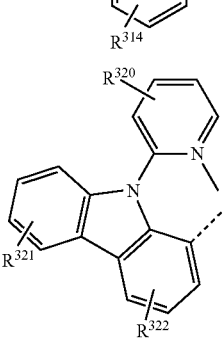
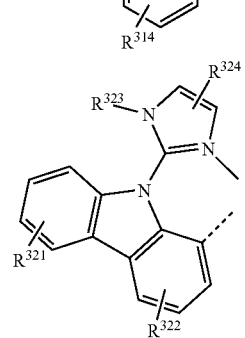

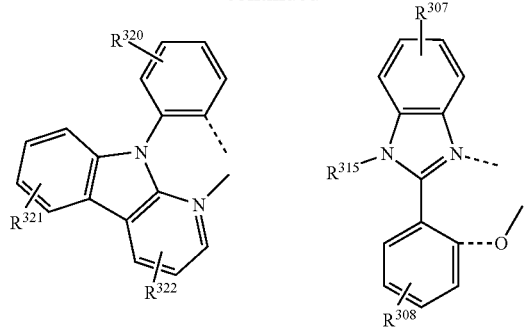

In Group D,
R$^{300}$ to R$^{302}$ may each independently be, e.g., hydrogen, deuterium, a C1 to C30 alkyl group substituted or unsubstituted with a halogen, a C6 to C30 aryl group substituted or unsubstituted with a C1 to C30 alkyl group, or a halogen, and R$^{303}$ to R$^{324}$ may each independently be, e.g., hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, SF$_5$, a trialkylsilyl group having a substituted or unsubstituted C1 to C30 alkyl group, a dialkylarylsilyl group having a substituted or unsubstituted C1 to C30 alkyl group and C6 to C30 aryl group, or a triarylsilyl group having a substituted or unsubstituted C6 to C30 aryl group.

For example, the dopant may represented by Chemical Formula Z-1.

[Chemical Formula Z-1]

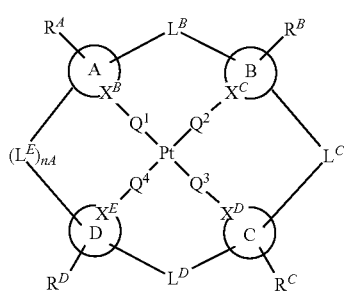

In Chemical Formula Z-1, rings A, B, C, and D may each independently be, e.g., 5- or 6-membered carbocyclic or heterocyclic rings;

R$^A$, R$^B$, R$^C$, and R$^D$ independently indicate monosubstitution, disubstitution, trisubstitution, or tetrasubstitution, or unsubstitution;

L$^B$, L$^C$, and L$^D$ may each independently be, e.g., a direct bond, BR, NR, PR, O, S, Se, C=O, S=O, SO$_2$, CRR', SiRR', GeRR', or a combination thereof;

when nA is 1, L$^E$ is selected from a direct bond, BR, NR, PR, O, S, Se, C=O, S=O, SO$_2$, CRR', SiRR', GeRR', and a combination thereof; and when nA is 0, L$^E$ is not present;

R$^A$, R$^B$, R$^C$, R$^D$, R, and R' may each independently be, e.g., hydrogen, deuterium, a halogen, an alkyl group, a cycloalkyl group, a heteroalkyl group, an arylalkyl group, an alkoxy group, an aryloxy group, an amino group, a silyl group, an alkenyl group, a cycloalkenyl group, a heteroalkenyl group, an alkynyl group, an aryl group, a heteroaryl group, an acyl group, a carbonyl group, a carboxylic acid group, an ester group, a nitrile group, an isonitrile group, a sulfanyl group, a sulfinyl group, a sulfonyl group, a phosphino group, or a combination thereof; any adjacent groups of R$^A$, R$^B$, R$^C$, R$^D$, R, and R' are arbitrarily linked with each other to form a ring; X$^B$, X$^C$, X$^D$, and X$^E$ are independently selected from carbon and nitrogen; and Q$^1$, Q$^2$, Q$^3$, and Q$^4$ are independently selected from oxygen or a direct bond.

In an implementation, the composition for the organic optoelectronic device according to an embodiment may include a dopant represented by Chemical Formula IV or Chemical Formula V.

[Chemical Formula IV]

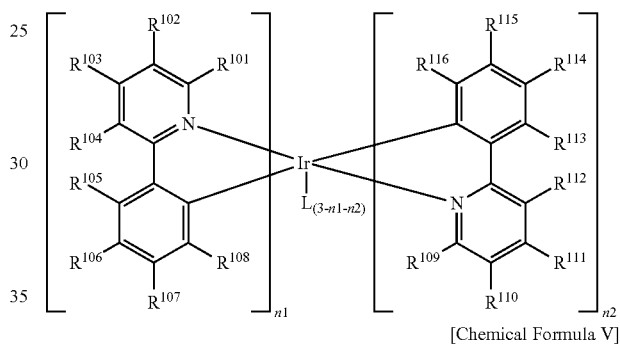

[Chemical Formula V]

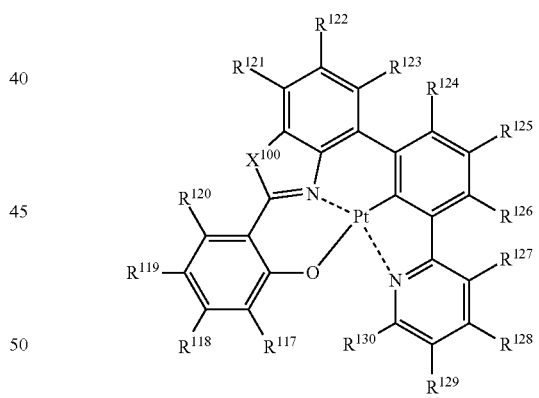

In Chemical Formula IV and Chemical Formula V,
X$^{100}$ is selected from O, S, and NR$^{131}$,
R$^{101}$ to R$^{131}$ are independently hydrogen, deuterium, a substituted or unsubstituted C1 to C10 alkyl group, a substituted or unsubstituted C6 to C20 aryl group, or —SiR$^{132}$R$^{133}$R$^{134}$,
R$^{132}$ to R$^{134}$ are independently C1 to C6 alkyl group,
at least one of R$^{101}$ to R$^{116}$ is a functional group represented by Chemical Formula IV-1,
L is a bidentate ligand of a monovalent anion, which is a ligand that coordinates to iridium through a non-covalent electron pair of carbon or heteroatom, and
n1 and n2 are independently an integer of 0 to 3, provided that n1+n2 is any one of 1 to 3,

[Chemical Formula IV-1]

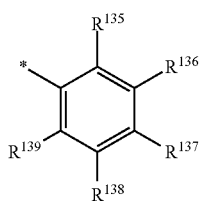

wherein, in Chemical Formula IV-1, $R^{135}$ to $R^{139}$ are independently hydrogen, deuterium, a substituted or unsubstituted C1 to C10 alkyl group, a substituted or unsubstituted C6 to C20 aryl group, or —$SiR^{132}R^{133}R^{134}$, indicates a linking portion with the carbon atom, and at least one of $R^{117}$ to $R^{131}$ is —$SiR^{132}R^{133}R^{134}$ or a tert-butyl group.

The composition for the organic optoelectronic device may be formed by a dry film formation method such as chemical vapor deposition (CVD).

Hereinafter, an organic optoelectronic device including the aforementioned composition for the organic optoelectronic device is described.

The organic optoelectronic device may be a device to convert electrical energy into photoenergy and vice versa, and may include, e.g., an organic photoelectric device, an organic light emitting diode, an organic solar cell, or an organic photo conductor drum.

Herein, an organic light emitting diode as one example of an organic optoelectronic device is described referring to drawings.

Figure 2:
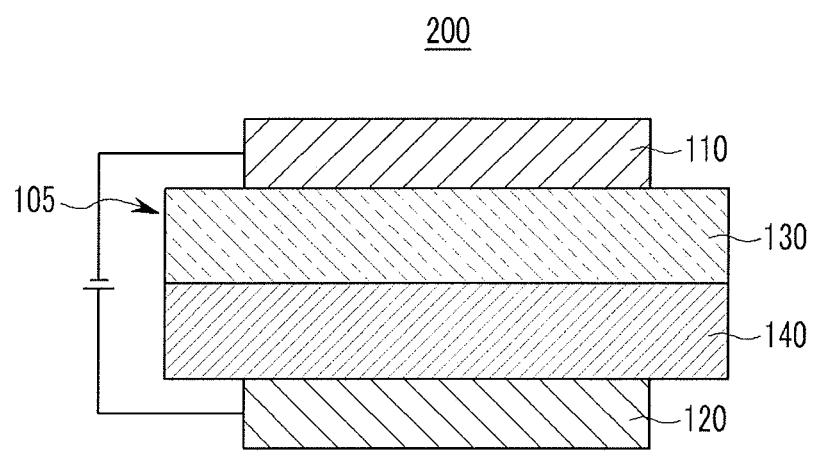

FIGS. 1 and 2 illustrate cross-sectional views showing organic light emitting diodes according to embodiments.

Referring to FIG. 1, an organic optoelectronic device 100 according to an embodiment includes an anode 120 and a cathode 110 facing each other and an organic layer 105 disposed between the anode 120 and the cathode 110.

The anode 120 may be made of a conductor having a large work function to help hole injection, and may be, e.g., a metal, a metal oxide and/or a conductive polymer. The anode 120 may be, e.g. a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline.

The cathode 110 may be made of a conductor having a small work function to help electron injection, and may be, e.g., a metal, a metal oxide and/or a conductive polymer. The cathode 110 may be, e.g., a metal such as magnesium, calcium, sodium, potassium, titanium, indium, yttrium, lithium, gadolinium, aluminum, silver, tin, lead, cesium, barium, and the like or an alloy thereof; a multi-layer structure material such as LiF/Al, $LiO_2$/Al, LiF/Ca, LiF/Al and $BaF_2$/Ca.

The organic layer 105 may include the aforementioned composition for the organic optoelectronic device.

The organic layer 105 may include, e.g., a light emitting layer 130, and the light emitting layer 130 may include, e.g., the aforementioned composition for the organic optoelectronic device.

The aforementioned composition for the organic optoelectronic device may be, e.g., a green or red light emitting composition.

The light emitting layer 130 may include, e.g., the aforementioned first compound, second compound, and third compound as each phosphorescent host.

Referring to FIG. 2, an organic light emitting diode 200 may further include a hole auxiliary layer 140 in addition to the light emitting layer 130. The hole auxiliary layer 140 further increases hole injection and/or hole mobility and blocks electrons between the anode 120 and the light emitting layer 130. The hole auxiliary layer 140 may be, for example, a hole transport layer, a hole injection layer, and/or an electron blocking layer, and may include at least one layer.

The hole auxiliary layer 140 may include, e.g., at least one of the compounds of Group E.

In an implementation, the hole auxiliary layer 140 may include a hole transport layer between the anode 120 and the light emitting layer 130 and a hole transport auxiliary layer between the light emitting layer 130 and the hole transport layer, and at least one of compounds of Group E may be included in the hole transport auxiliary layer.

[Group E]

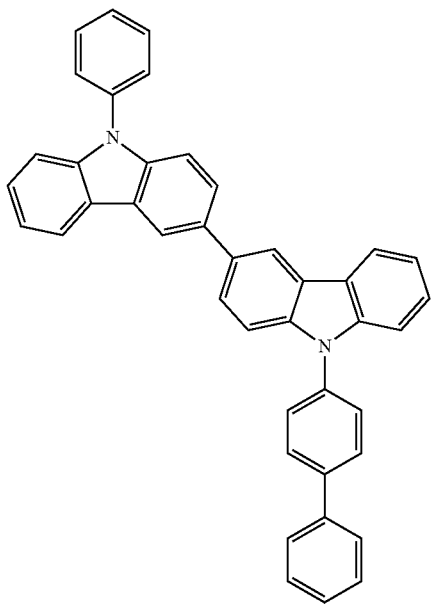

95
-continued
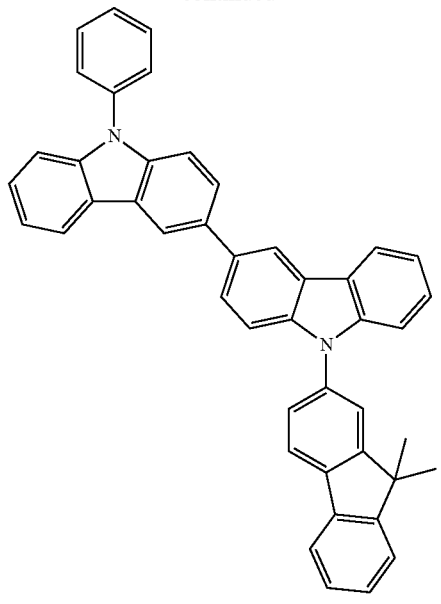
96
-continued
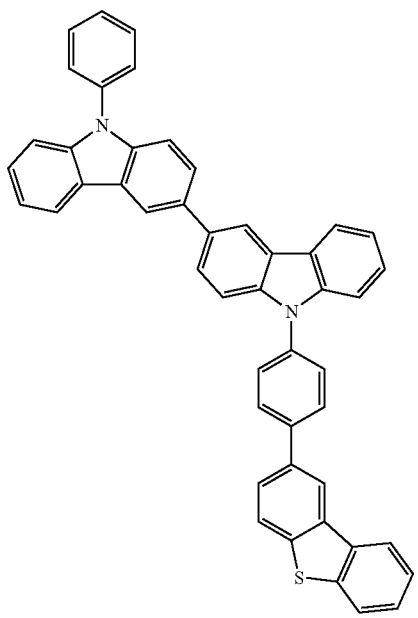 [SMILES: c1ccc(-n2c3ccccc3c3cc(-c4ccc5c(c4)c4ccccc4n5-c4ccc(-c5ccc6sc7ccccc7c6c5)cc4)ccc32)cc1]
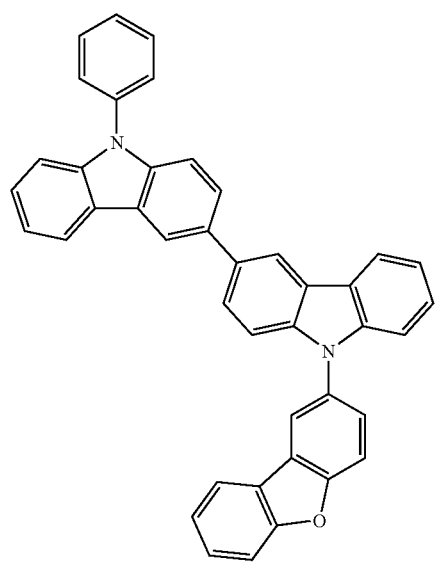
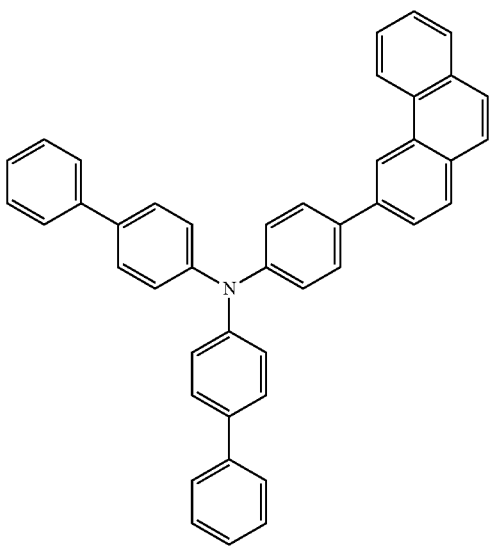
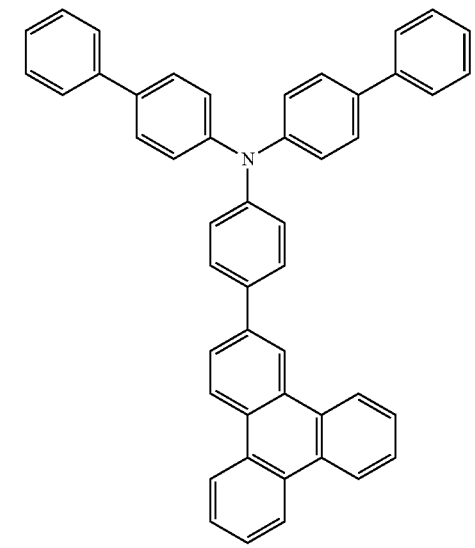

97
-continued
98
-continued
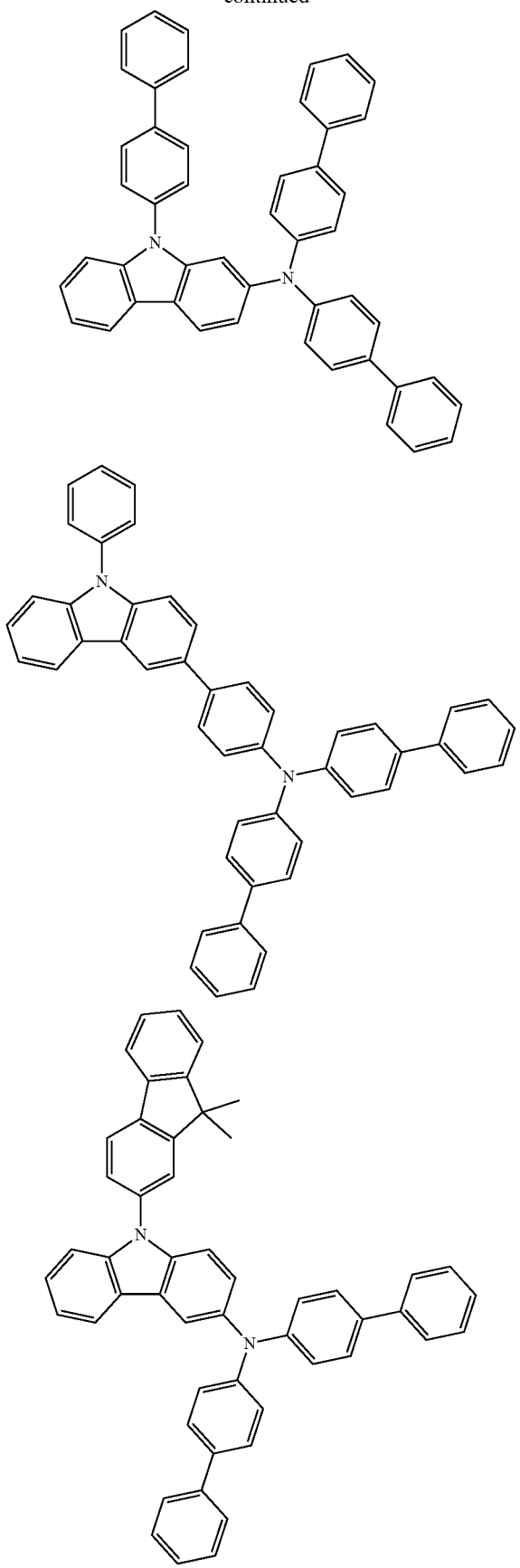
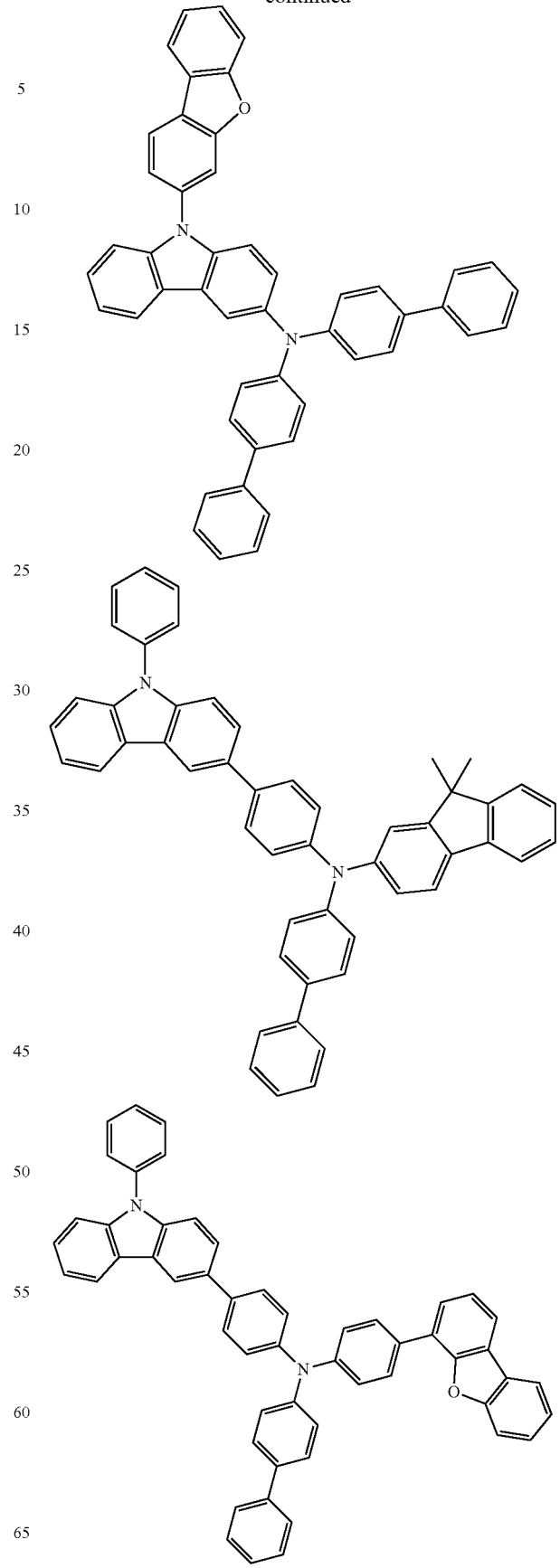

99
-continued
100
-continued
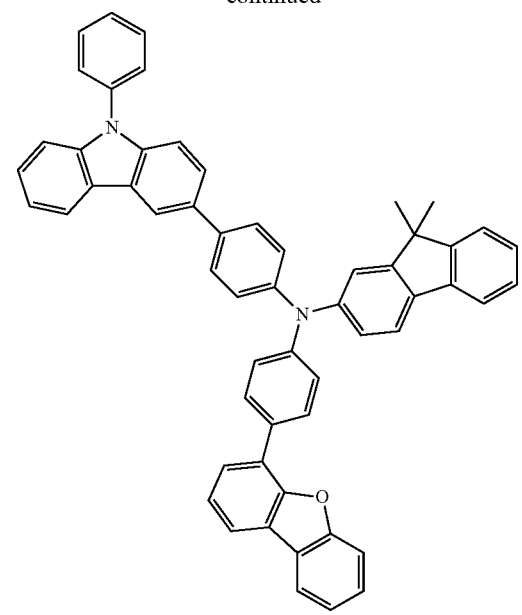
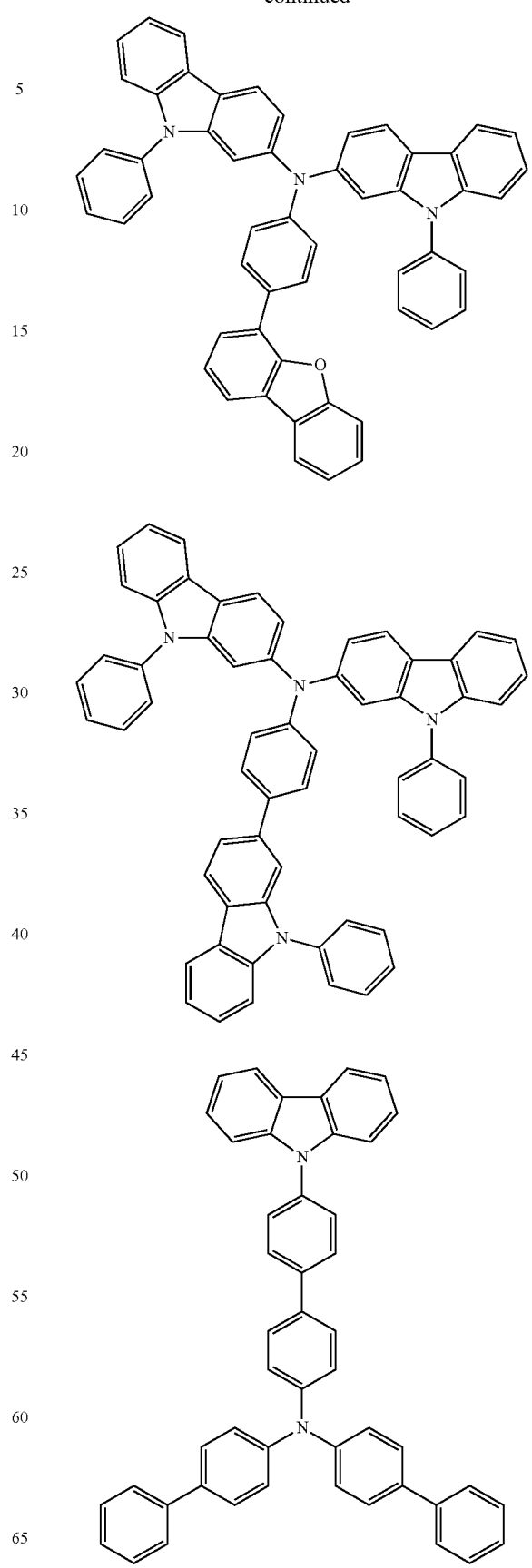

101
-continued
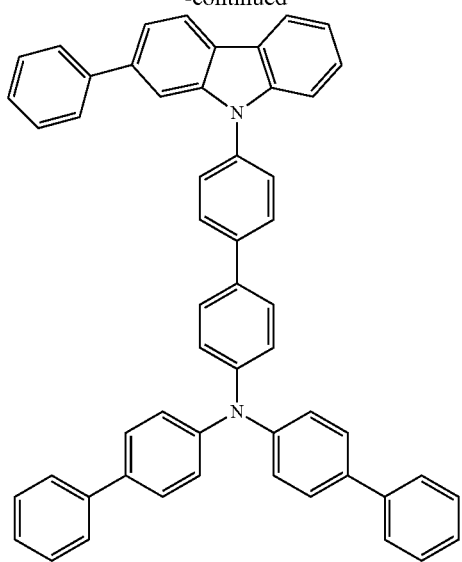
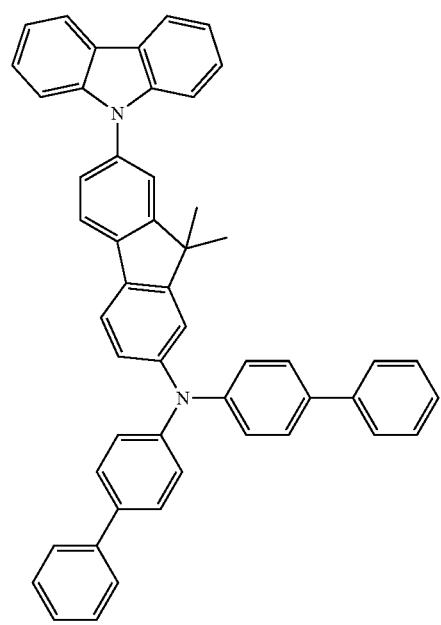 [SMILES: CC1(C)c2cc(N(c3ccc(-c4ccccc4)cc3)c3ccc(-c4ccccc4)cc3)ccc2-c2ccc(-n3c4ccccc4c4ccccc43)cc21]
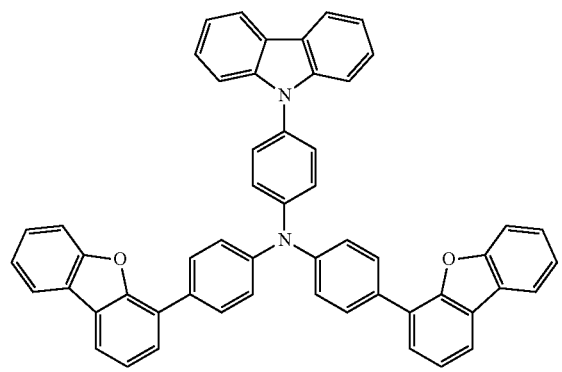
102
-continued
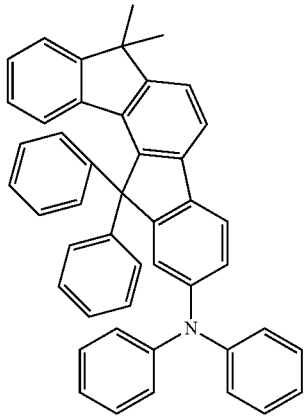
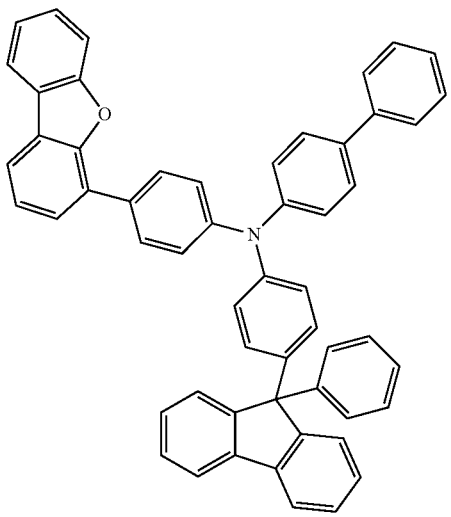
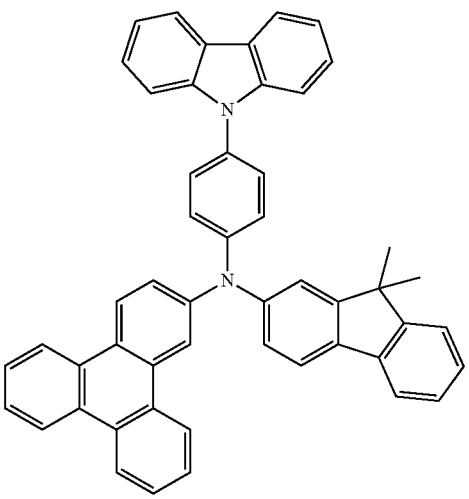

103
-continued
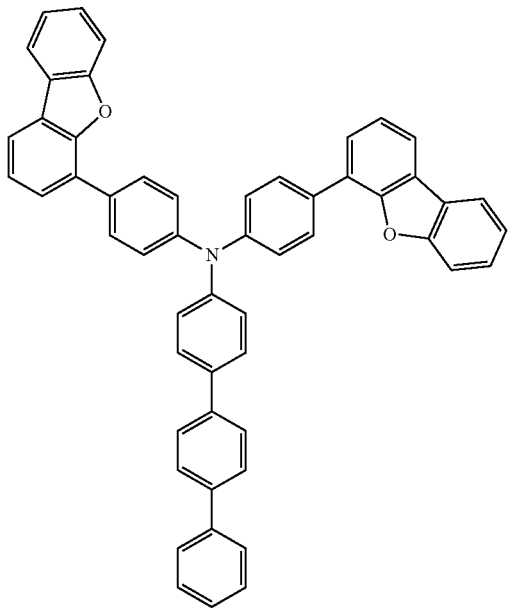
104
-continued
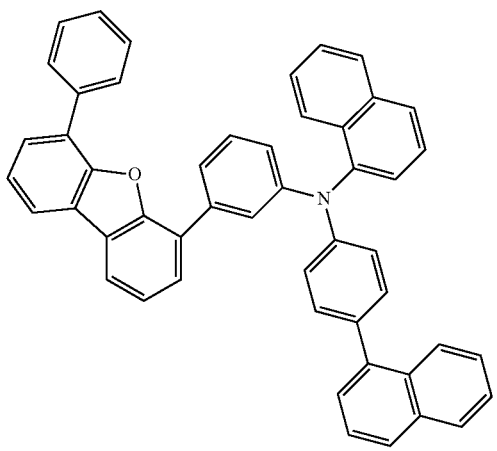 [SMILES: c1ccc(-c2cccc3c2oc2c(-c4cccc(N(c5ccc(-c6cccc7ccccc67)cc5)c5cccc6ccccc56)c4)cccc23)cc1]
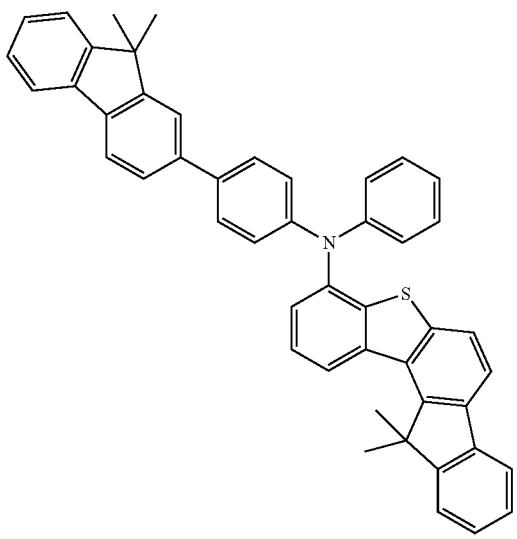
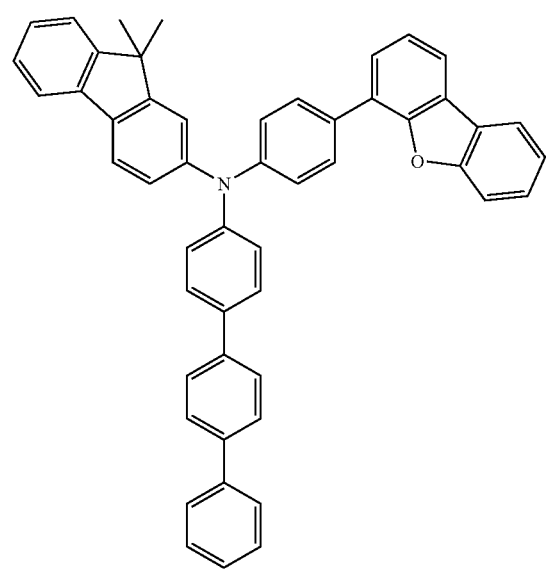
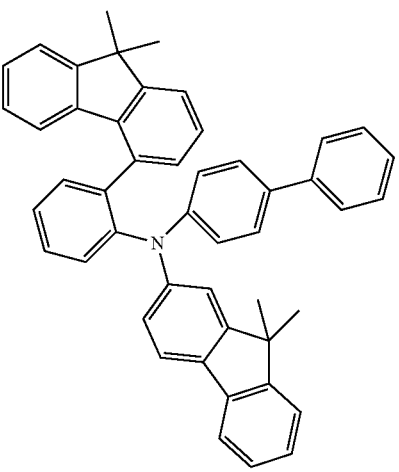

105
-continued
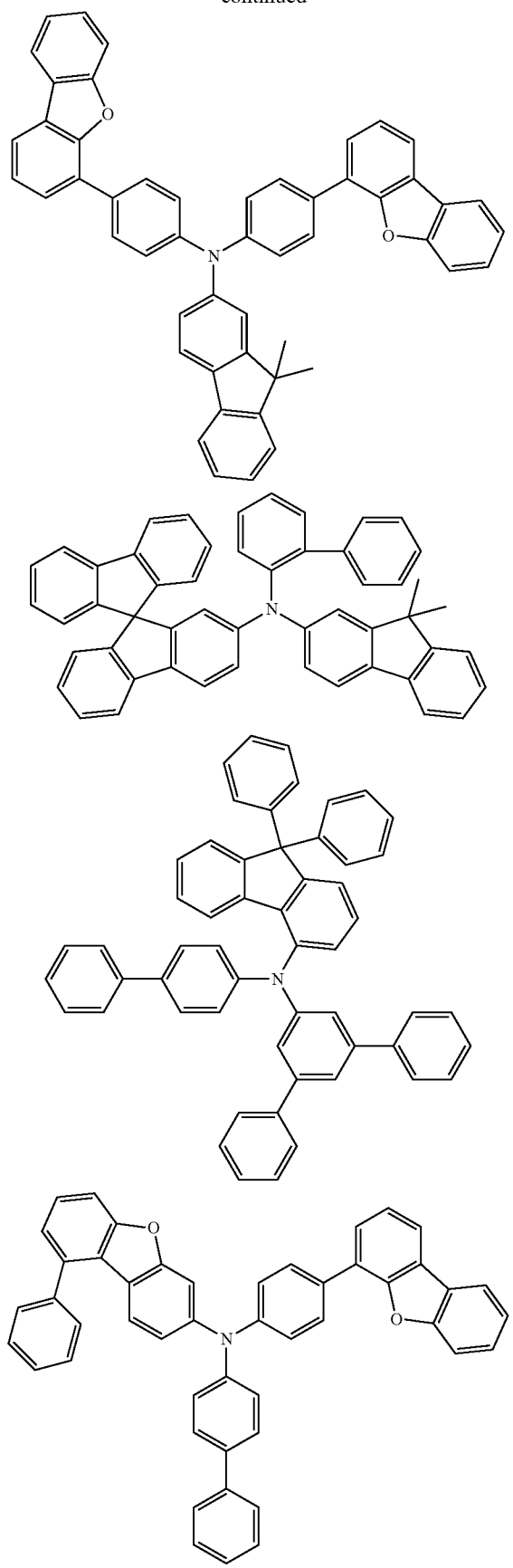
106
-continued
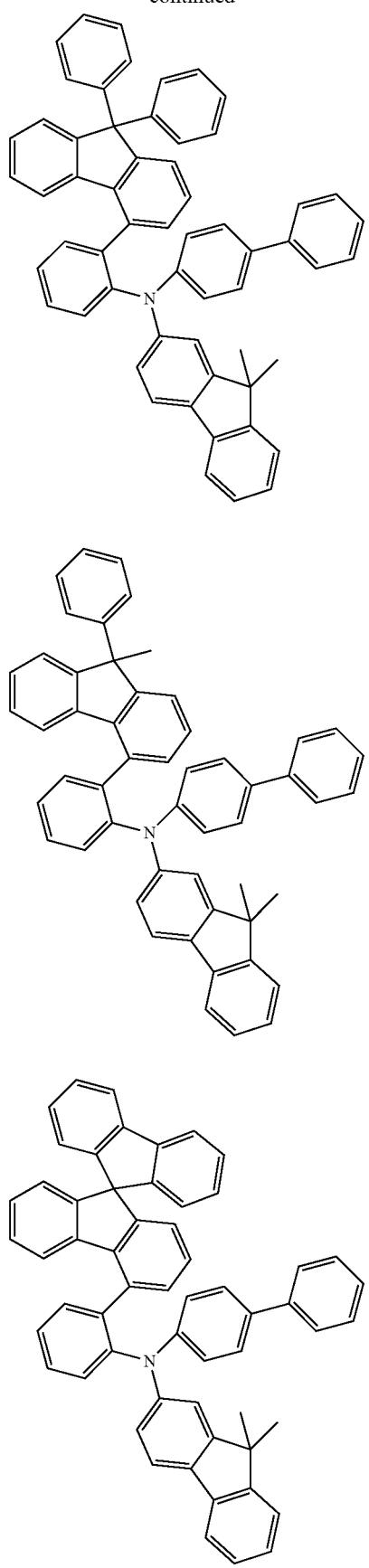

107
-continued
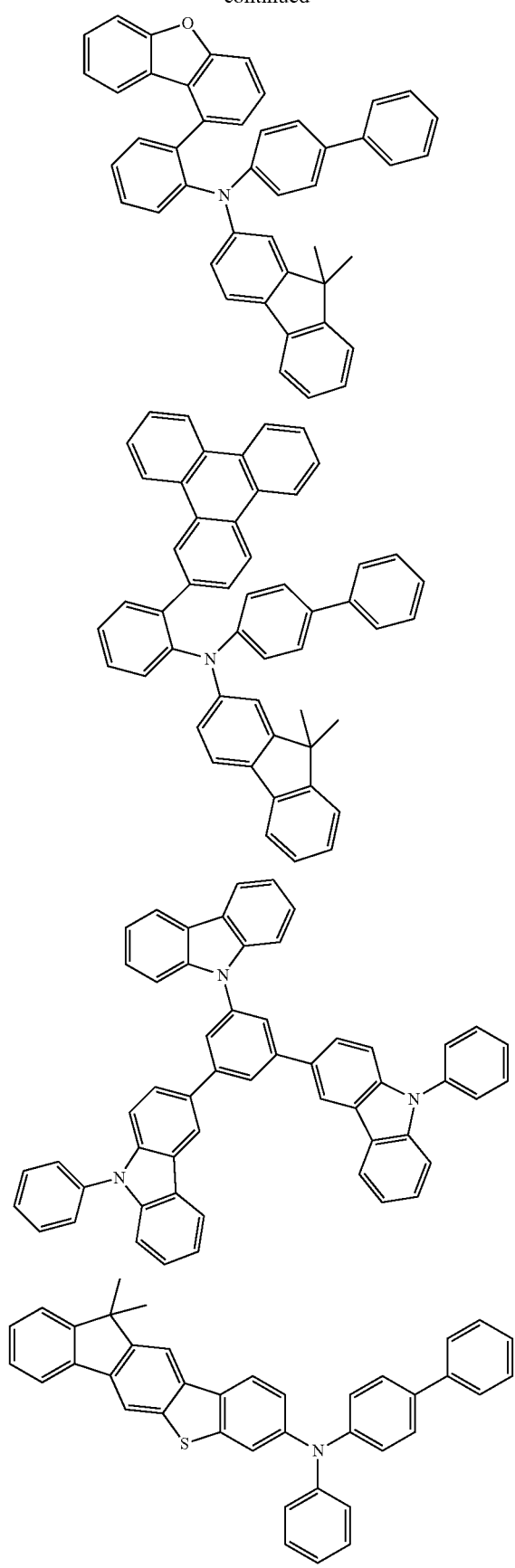
108
-continued
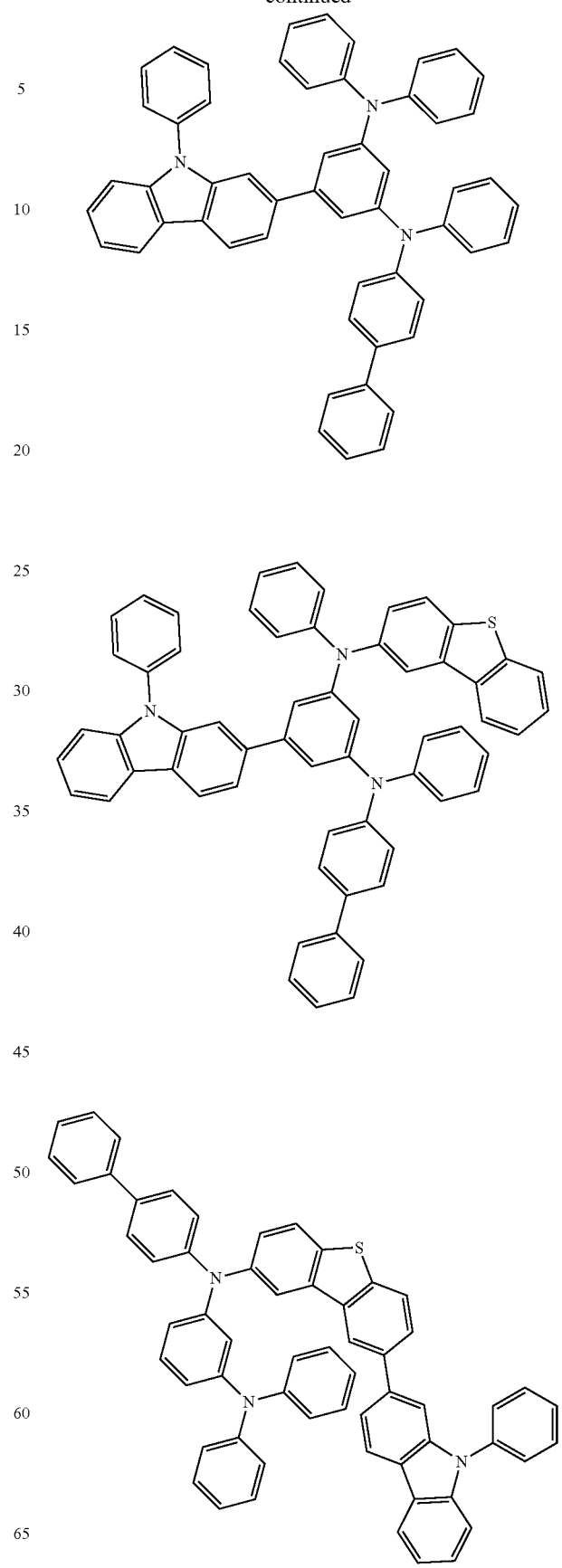

109
-continued
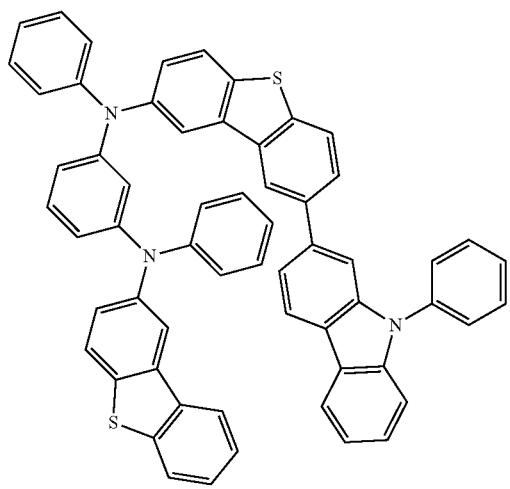
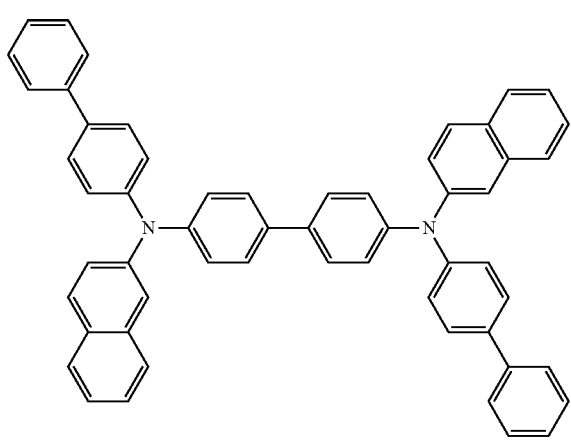
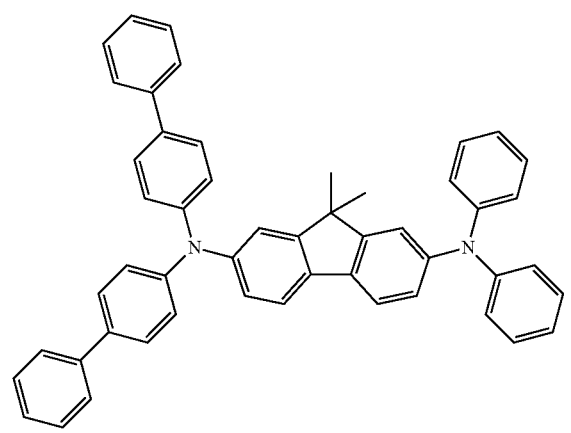
110
-continued
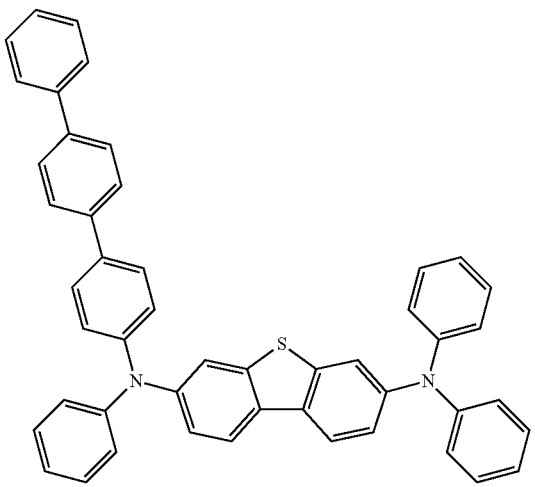 [SMILES: c1ccc(-c2ccc(-c3ccc(N(c4ccccc4)c4ccc5c(c4)sc4cc(N(c6ccccc6)c6ccccc6)ccc45)cc3)cc2)cc1]
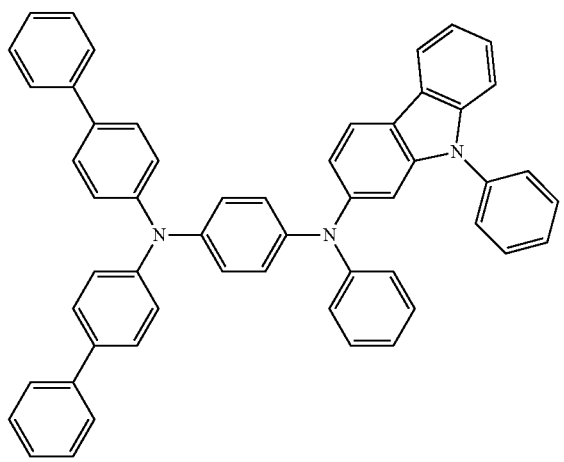
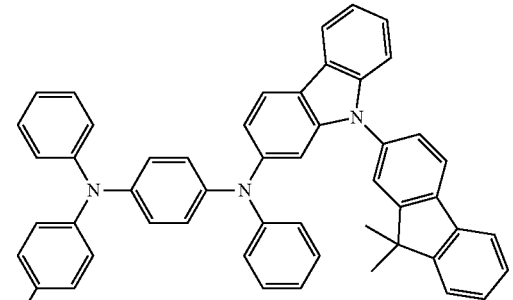

111
-continued
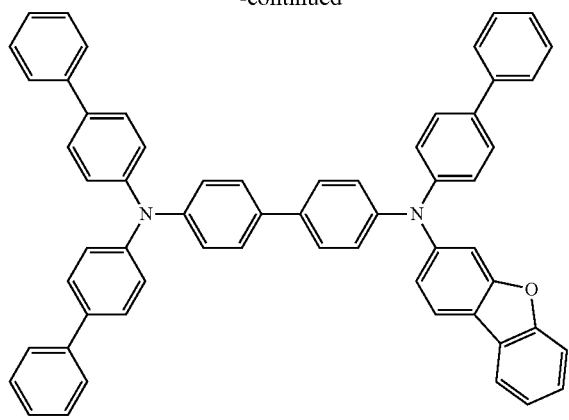
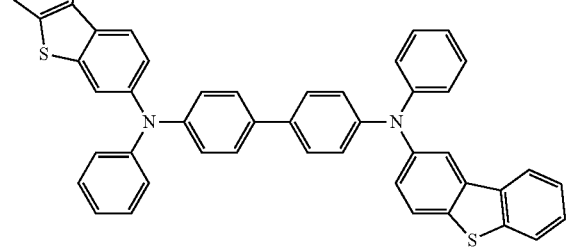
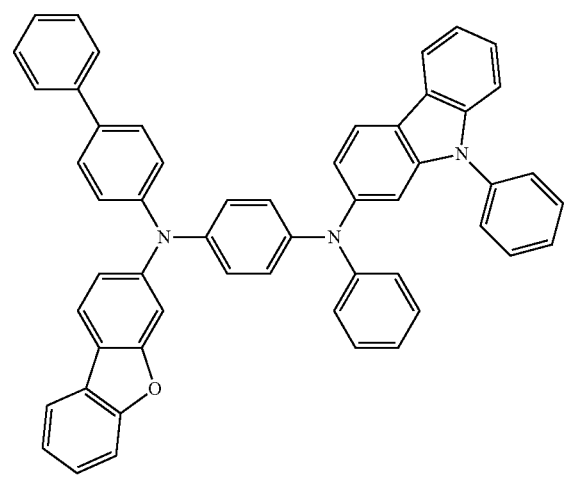
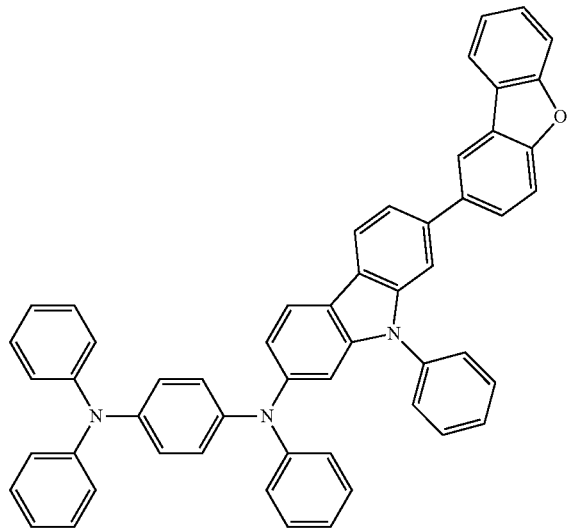
112
-continued
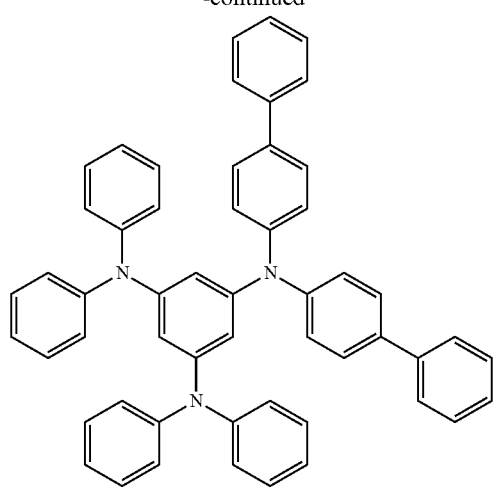
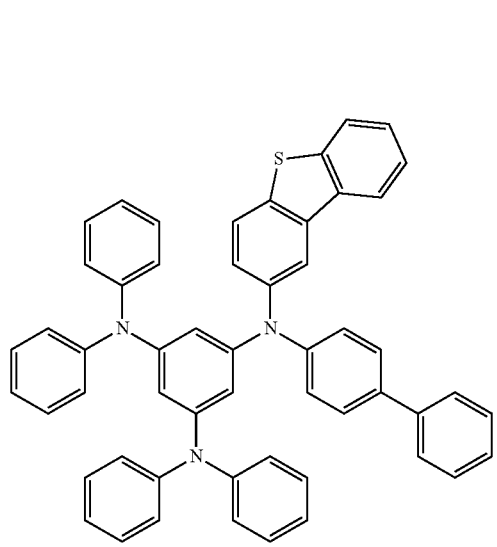 [SMILES: c1ccc(-c2ccc(N(c3cc(N(c4ccccc4)c4ccccc4)cc(N(c4ccccc4)c4ccccc4)c3)c3ccc4sc5ccccc5c4c3)cc2)cc1]
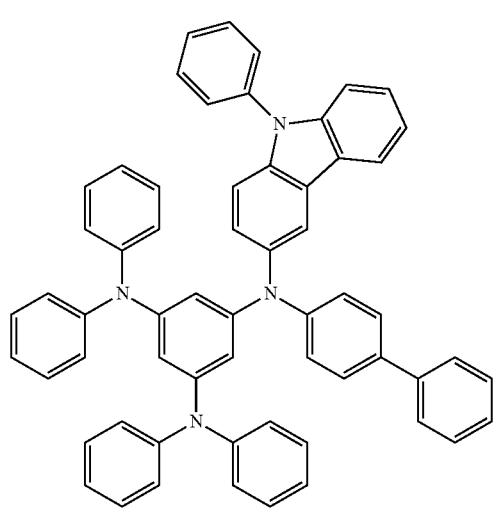

113
-continued
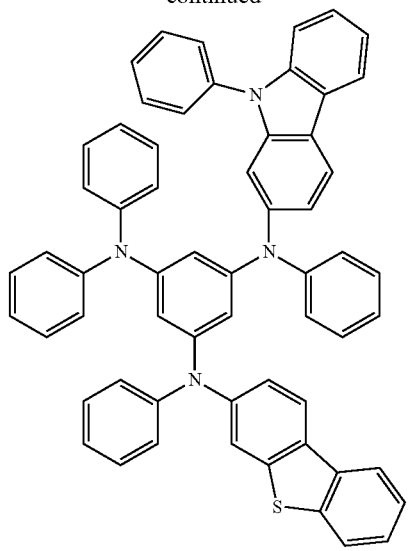
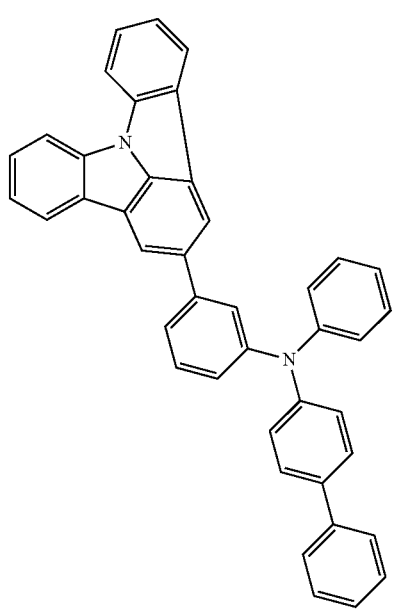
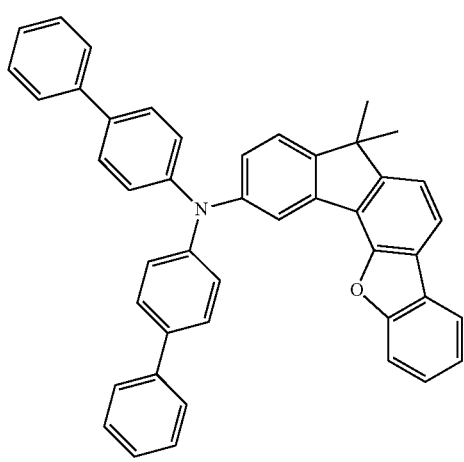 [SMILES: CC1(C)c2ccc(N(c3ccc(-c4ccccc4)cc3)c3ccc(-c4ccccc4)cc3)cc2-c2c1ccc1c2oc2ccccc21]
114
-continued
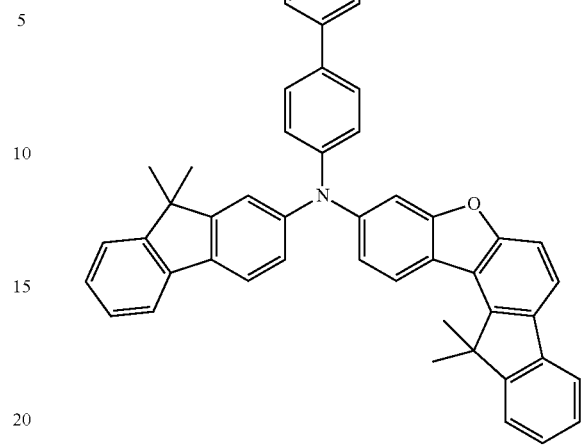
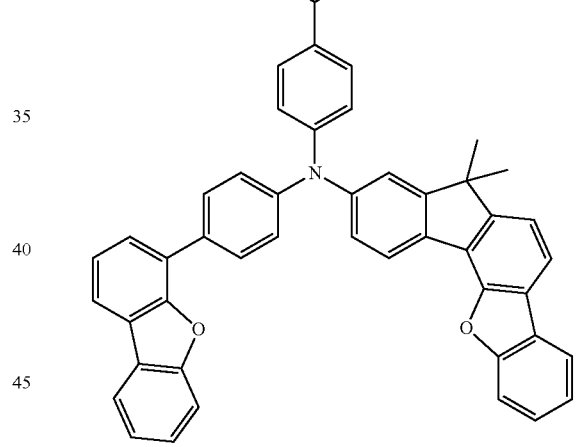
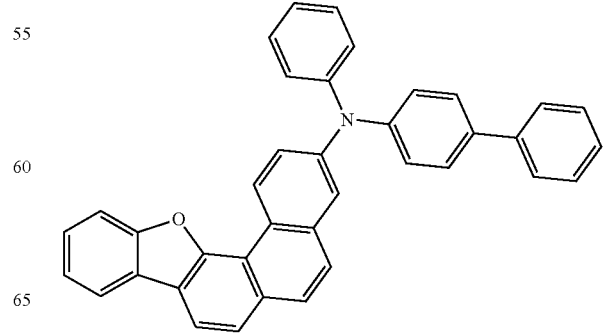
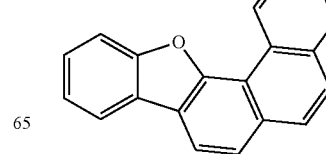

115
-continued
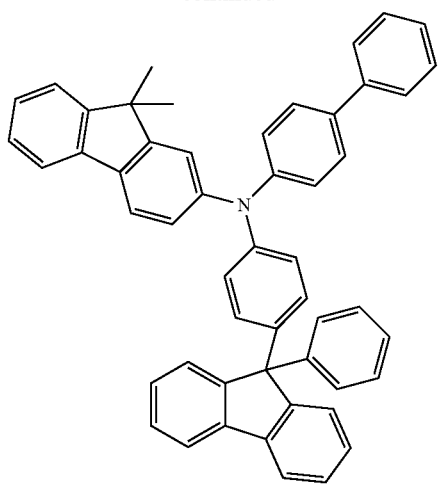 [SMILES: CC1(C)c2ccccc2-c2ccc(N(c3ccc(-c4ccccc4)cc3)c3ccc(C4(c5ccccc5)c5ccccc5-c5ccccc54)cc3)cc21]
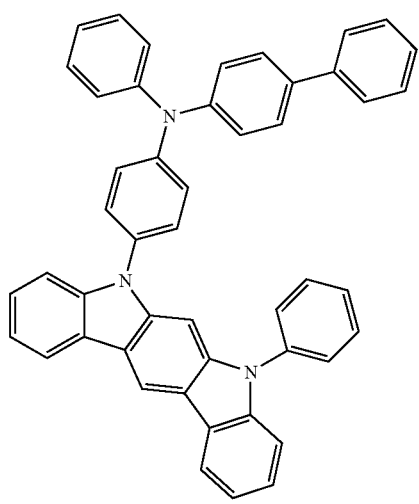
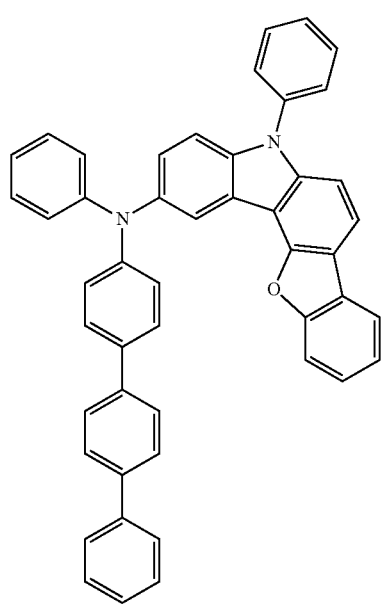
116
-continued
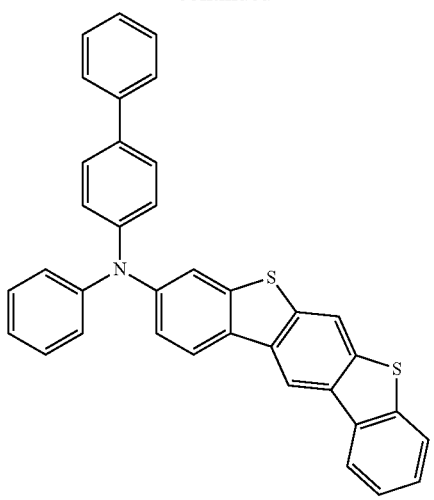
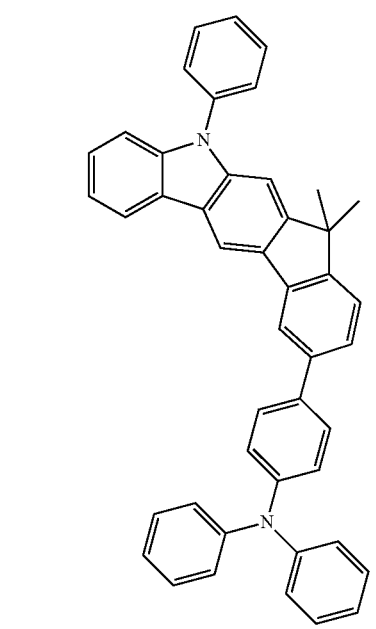 [SMILES: CC1(C)c2ccc(-c3ccc(N(c4ccccc4)c4ccccc4)cc3)cc2-c2cc3c4ccccc4n(-c4ccccc4)c3cc21]
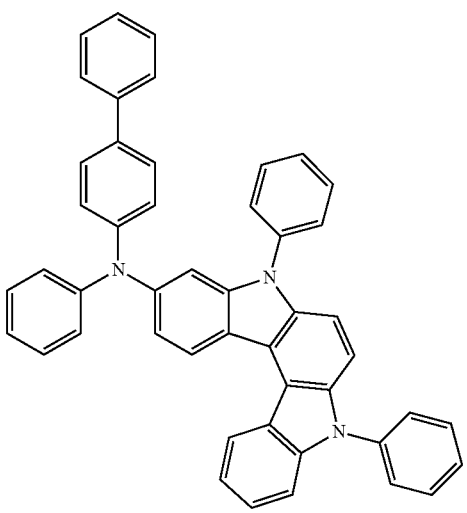

-continued

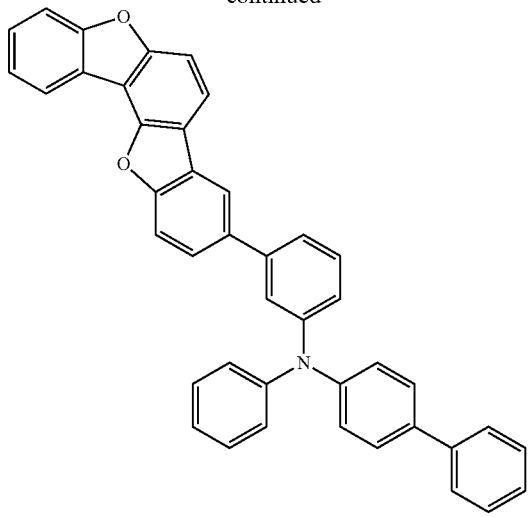

In addition to the aforementioned compounds, the hole transport auxiliary layer may also include other suitable compounds.

In an implementation, in FIG. 1 or 2, an organic light emitting diode may further include an electron transport layer, an electron injection layer, a hole injection layer, and the like as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic Optoelectronic Device

Synthesis Example 1: Synthesis of Intermediate Int-6

[Reaction Scheme 1]

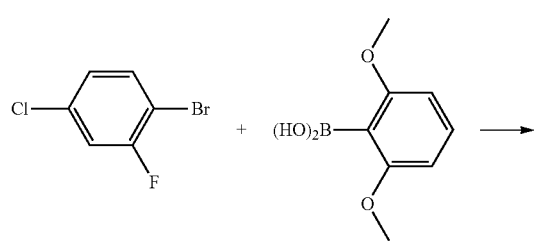

-continued

Step 1: Synthesis of Intermediate Int-1

1-Bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were put in a round-bottomed flask and dissolved in 500 ml of THF and 200 ml of distilled water and then, refluxed and stirred at 60° C. for 12 hours. When a reaction was complete, 38 g (51%) of Intermediate Int-1 was obtained through column chromatography (Hexane:DCM (20%)) after removing an aqueous layer therefrom.

Step 2: Synthesis of Intermediate Int-2

Intermediate Int-1 (38 g, 142 mmol) and pyridine hydrochloride (165 g, 1425 mmol) were put in a round-bottomed flask and then, refluxed and stirred at 200° C. for 24 hours.

When a reaction was complete, the resultant was cooled down to ambient temperature, slowly poured into distilled water and then, stirred for one hour. A solid therein was filtered to obtain 23 g (68%) of Intermediate Int-2.

Step 3: Synthesis of Intermediate Int-3

Intermediate Int-2 (23 g, 96 mmol) and K₂CO₃ (20 g, 144 mmol) were put in a round-bottomed flask and dissolved in 100 ml of NMP and then, refluxed and stirred at 180° C. for 12 hours. When a reaction was complete, the mixture was poured into an excess of distilled water. A solid therein was filtered, dissolved in ethyl acetate, and dried with MgSO₄, and an organic layer was removed therefrom under a reduced pressure. Subsequently, 16 g (76%) of Intermediate Int-3 was obtained through column chromatography (hexane:ethyl acetate (30%)).

Step 4: Synthesis of Intermediate Int-4

Intermediate Int-3 (16 g, 73 mmol) and pyridine (12 ml, 146 mmol) were put in a round bottomed flask and dissolved in 200 ml of DCM. A temperature was decreased down to 0° C., and trifluoromethanesulfonic anhydride (14.7 ml, 88 mmol) was slowly added thereto in a dropwise fashion. After stirring the mixture for 6 hours, when a reaction was complete, an excess of distilled water was added thereto and then, stirred for 30 minutes and extracted with DCM. After removing an organic solvent under a reduced pressure, the extract was vacuum-dried to obtain 22.5 g (88%) of Intermediate Int-4.

Step 5: Synthesis of Intermediate Int-5

Intermediate Int-4 (25 g, 71.29 mmol), 3-biphenylboronic acid (16.23 g, 81.78 mmol), K₂CO₃ (14.78 g, 106.93 mmol), and Pd(PPh₃)₄ (4.12 g, 3.56 mmol) were used in the same method as Step 1 to synthesize 21 g (83%) of Intermediate Int-5.

Step 6: Synthesis of Intermediate Int-6

Intermediate Int-5 (21 g, 59.18 mmol), bis(pinacolato)diboron (19.54 g, 76.94 mmol), Pd(dppf)Cl2 (2.42 g, 2.96 mmol), tricyclohexylphosphine (3.32 g, 11.84 mmol), and potassium acetate (11.62 g, 118.37 mmol) were put in a round-bottomed flask and dissolved in 320 ml of DMF. The mixture was refluxed and stirred at 120° C. for 10 hours. When a reaction was complete, the mixture was poured into an excess of distilled water and then, stirred for 1 hour. A solid therein was filtered and then, dissolved in DCM. MgSO₄ was used to remove moisture therefrom, and an organic solvent was filtered with a silica gel pad and removed under a reduced pressure. The solid was recrystallized with ethyl acetate and hexane to obtain 18.49 g (70%) of Intermediate Int-6.

Synthesis Example 2: Synthesis of Intermediate Int-14

[Reaction Scheme 2]

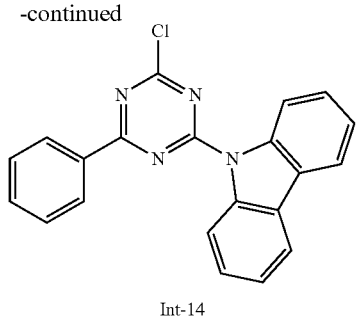

Int-14

2,4-Dichloro-6-phenyl-1,3,5-triazine (30 g, 132.71 mmol), carbazole (17.75 g, 106.17 mmol), and sodium tert-butoxide (14.03 g, 145.98 mmol) were put in a round-bottomed flask and then, stirred with 650 ml of THF at ambient temperature for 12 hours. A solid generated therein was filtered and then, stirred in an aqueous layer for 30 minutes. After the filtration, the solid was dried to obtain 20 g (42%) of Intermediate Int-14.

Synthesis Example 3: Synthesis of Compound 1-65

[Reaction Scheme 3]

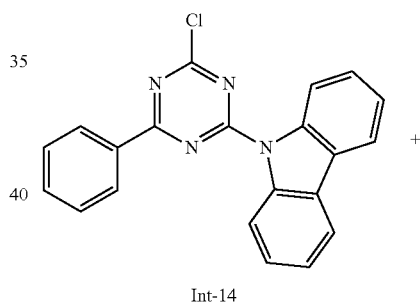

Int-14

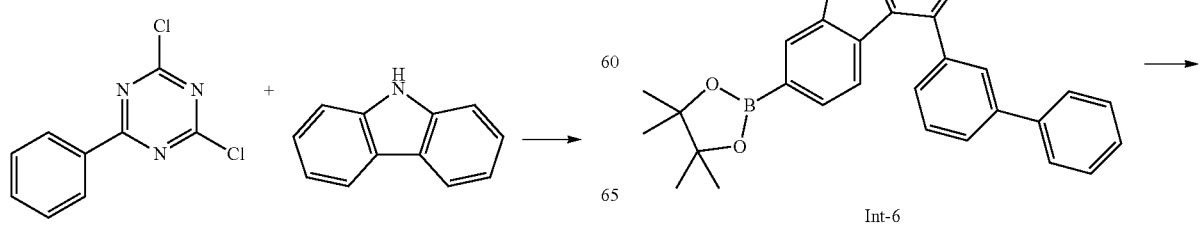

Int-6

121
-continued

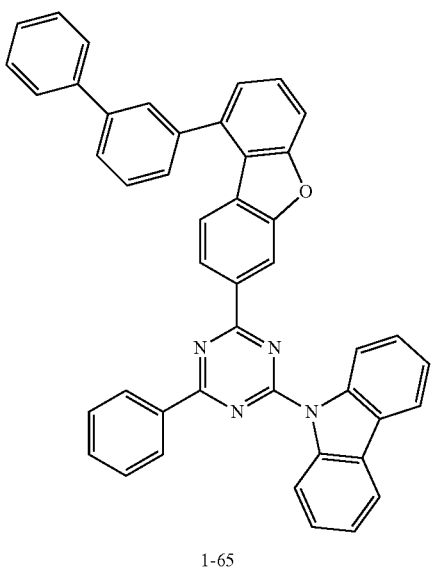

1-65

Intermediate Int-14 (9.5 g, 26.62 mmol), Int-6 (14.26 g, 31.95 mmol), $K_2CO_3$ (9.20 g, 66.56 mmol), and $Pd(PPh_3)_4$ (1.54 g, 1.33 mmol) were put in a round-bottomed flask and dissolved in 100 ml of THF and 40 ml of distilled water and then, refluxed and stirred at 70° C. for 12 hours. When a reaction was complete, the mixture was added to 500 mL of methanol, and a solid crystallized therein was filtered, dissolved in monochlorobenzene, filtered with silica gel/Celite, and after removing the organic solvent in an appropriate amount, recrystallized with methanol to obtain 13.14 g (77%) of Compound 1-65.

(LC/MS theoretical value: 640.23 g/mol, measured value: M+=641.39 g/mol)

Synthesis Example 4: Synthesis of Compound 1-66

[Reaction Scheme 4]

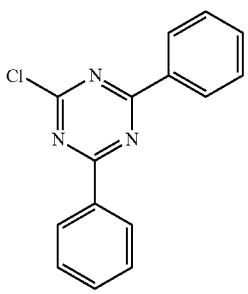

+

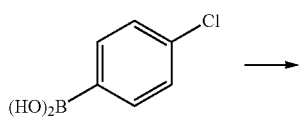

122
-continued

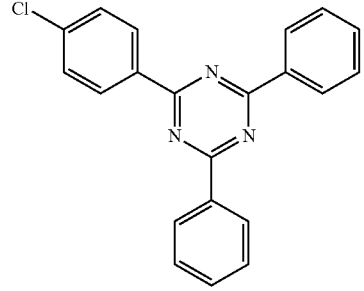

A-1-1

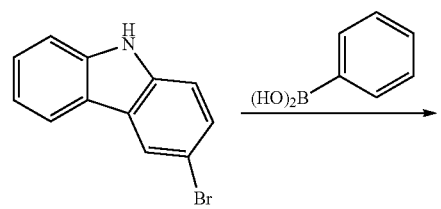

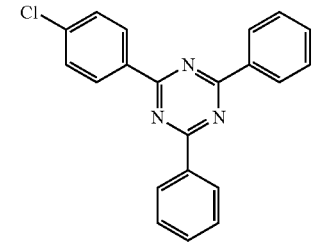

A-1-2

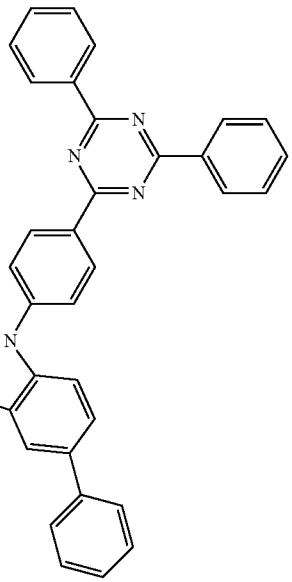

1-66

Step 1: Synthesis of Intermediate A-1-1

23.4 g (87.3 mmol) of 2-chloro-4,6-diphenyl-1,3,5-triazine was added to 100 mL of tetrahydrofuran, 100 mL of toluene, and 100 mL of distilled water in a 500 mL round-bottomed flask, 0.9 equivalents of (4-chlorophenyl)boronic acid, 0.03 equivalents of tetrakis(triphenylphosphine) palladium, and 2 equivalents of potassium carbonate were added thereto, and the mixture was heated and refluxed under a nitrogen atmosphere. The reaction solution was cooled down after 6 hours, an aqueous layer was removed, and an organic layer was dried under a reduced pressure. An obtained solid was washed with water and hexane, the solid was recrystallized with 200 mL of toluene to obtain 20 g (67% yield) of Intermediate A-1-1.

Step 2: Synthesis of Intermediate A-1-2

3-Bromocarbazole (35 g, 142 mmol) was dissolved in 0.5 L of tetrahydrofuran in a 1 L round-bottomed flask, and phenylboronic acid (17.3 g, 142 mmol) and tetrakis(triphenylphosphine) palladium (8.2 g, 7.1 mmol) were added thereto and stirred. Potassium carbonate saturated in water (49.1 g, 356 mmol) was added thereto and then, heated and refluxed at 80° C. for 12 hours. When a reaction was complete, water was added to the reaction solution, an extraction was performed using dichloromethane, and after removing moisture with anhydrous magnesium sulfite, the residue was filtered and concentrated under a reduced pressure. The obtained residue was separated and purified through column chromatography to obtain 22.0 g (64% yield) of Intermediate A-1-2.

Step 3: Synthesis of Compound 1-66

Intermediate A-1-2 (22.0 g, 90.4 mmol), Intermediate A-1-1 (31.1 g, 90.4 mmol), sodium t-butoxide (NaOtBu) (13.01 g, 135.6 mmol), Pd$_2$(dba)$_3$ (2.48 g, 2.7 mmol), and tri t-butylphosphine (P(tBu)$_3$) (5.49 g, 50% in toluene) were put in xylene (300 mL) and heated and refluxed for 12 hours under a nitrogen flow. After removing xylene, 200 mL of methanol was added to the obtained mixture and a solid crystallized therein was filtered, dissolved in monochlorobenzene, filtered with silica gel/Celite, and after concentrating the organic solvent in an appropriate amount to obtain Compound 1-66 (32 g, 64% yield). (LC/MS theoretical value: 550.22 g/mol, measured value: M+=551.23 g/mol)

Synthesis Example 5: Synthesis of Compound 1-15

[Reaction Scheme 5]

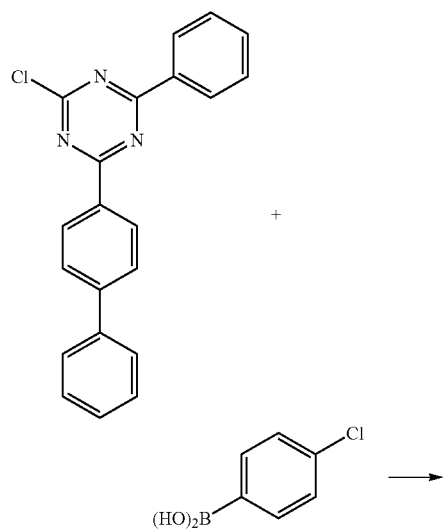

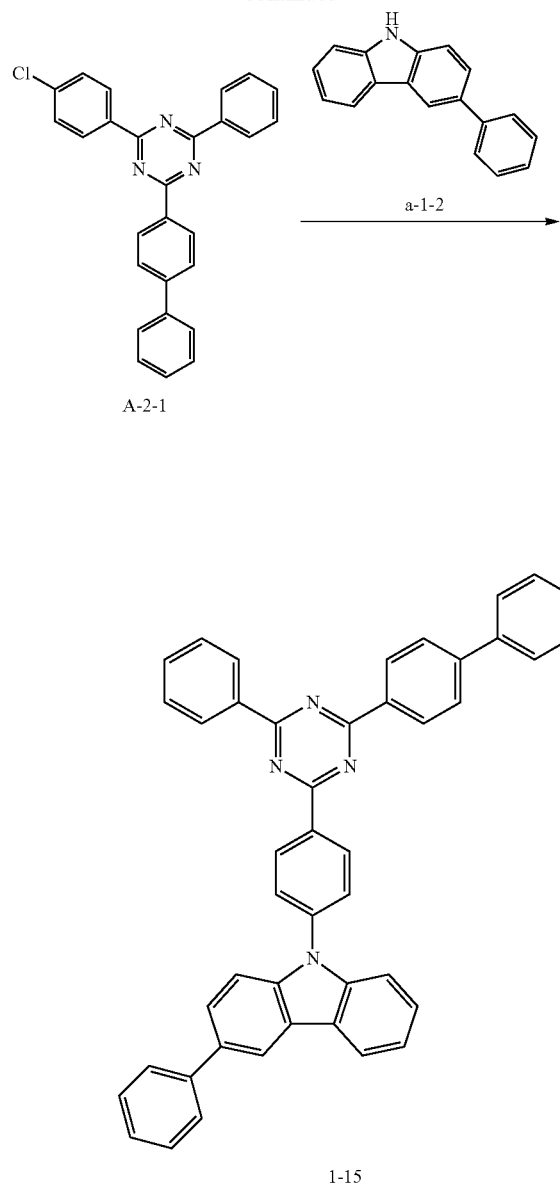

Step 1: Synthesis of Intermediate A-2-1

24 g (Yield=65%) of Intermediate A-2-1 was obtained according to the same synthesis method as in Step 1 of Synthesis Example 4 using 2-chloro-4-phenyl-6-(4-biphenyl)-1,3,5-triazine (30 g, 87.2 mmol).

Step 2: Synthesis of Compound 1-15

22.2 g (Yield=62%) of Compound 1-15 was obtained according to the same synthesis method as in Step 3 of Synthesis Example 4 using Intermediate A-2-1 (24 g, 57.2 mmol).

(LC/MS theoretical value: 626.25 g/mol, measured value: M+=627.44 g/mol)

Synthesis Example 6: Synthesis of Compound 1-63

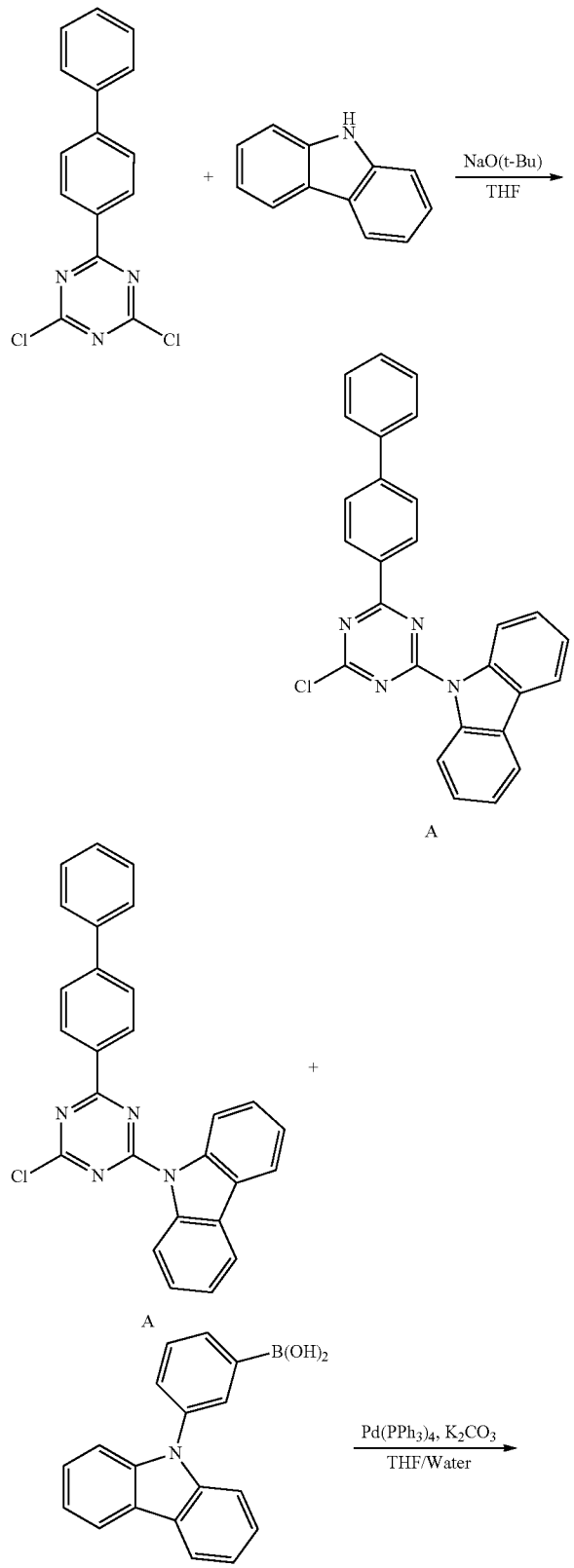

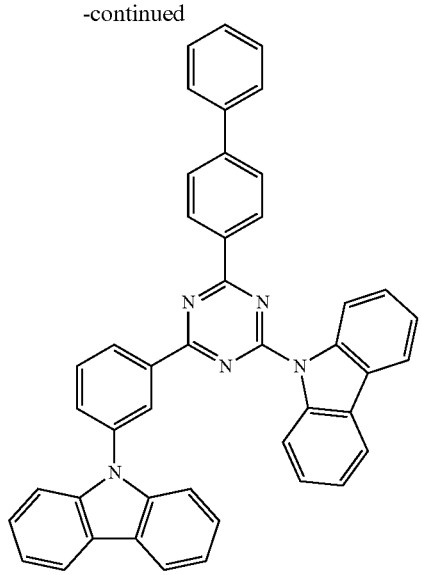

Step 1: Synthesis of Intermediate A 65.5 g (216.79 mmol) of 2-[1, 1'-biphenyl]-4-yl-4, 6-dichloro-1,3,5-triazine and 25 g (149.51 mmol) of carbazole were suspended in 800 ml of THF, and 15.09 g (156.99 mmol) of NaO(t-Bu) was slowly added thereto. After stirring the mixture for 12 hours at ambient temperature, a solid generated therein was filtered and then, washed sequentially with distilled water, acetone, and hexane in order to obtain 40.15 g of Intermediate A (Yield of 62%) as a target compound.

Step 2: Synthesis of Compound 1-63

10 g (23.10 mmol) of Intermediate A, 8.70 g (23.56 mmol) of 3-(9H-carbazol-9-yl)phenyl boronic acid, 0.8 g (0.69 mmol) of $Pd(PPh_3)_4$, and 6.39 g (46.2 mmol) of $K_2CO_3$ were suspended in 100 ml of THF and 50 ml of distilled water and then, refluxed and stirred for 12 hours. After the reaction, the mixture was cooled down to ambient temperature, and the produced solid was filtered and washed with distilled water and acetone. The washed solid was heated and dissolved in 200 ml of dichlorobenzene, silica gel-filtered, and recrystallized in 150 ml of dichlorobenzene to obtain 11 g of Compound 1-63 (Yield=74%).

(LC/MS: theoretical value: 639.75 g/mol, measured value: 640.40 g/mol)

Synthesis Example 7: Synthesis of Compound 2-2

The compound was synthesized by the method described in KR10-2017-0037277A.

Synthesis Example 8: Synthesis of Compound 2-72

The compound was synthesized by the method described in KR10-2018-0035196.

Synthesis Example 9: Synthesis of Compound 2-15

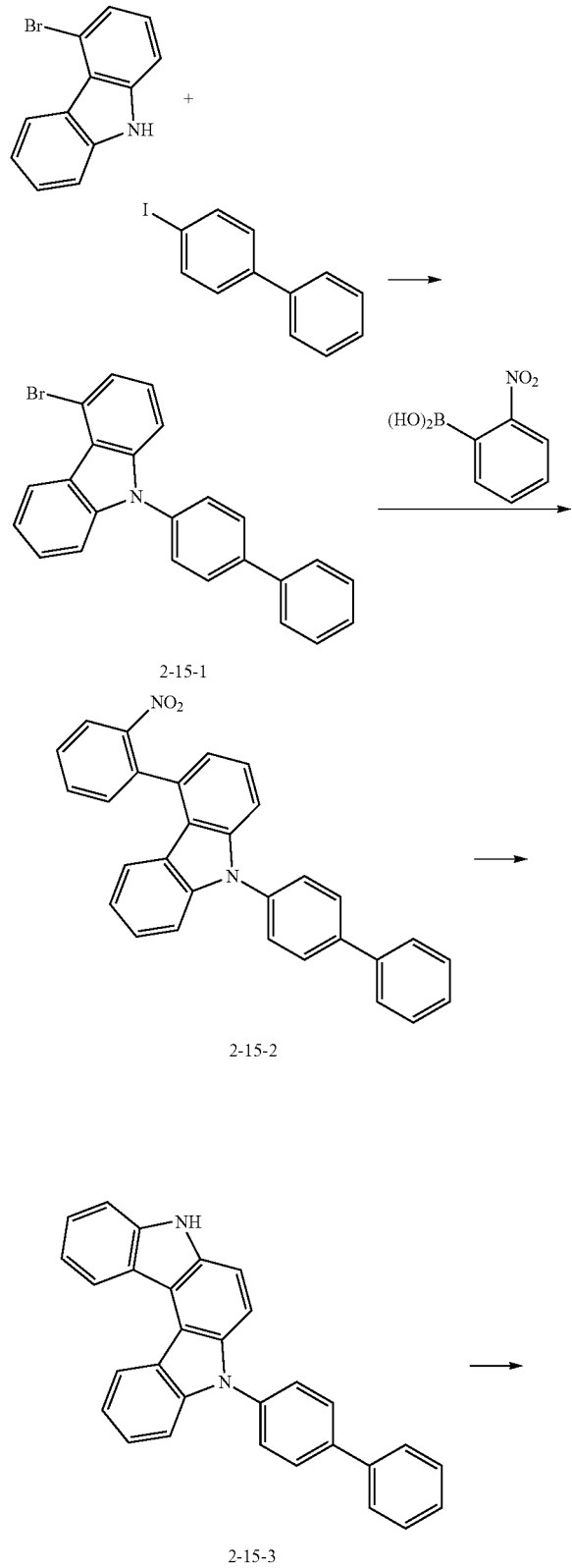

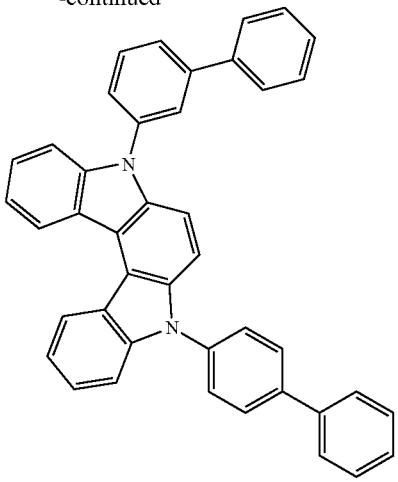

2-15

Step 1: Synthesis of Intermediate 2-15-1

10.44 g (42.41 mmol) of 4-Bromo-9H-carbazole, 11.88 g (42.41 mmol) of 4-iodo-1,1'-biphenyl (Sigma Aldrich Co., Ltd.), 0.388 g (0.424 mmol) of $Pd_2(dba)_3$, 0.206 g (0.848 mmol) of $P(t-Bu)_3$, and 6.11 g (63.61 mmol) of NaO(t-Bu) were suspended in 420 ml of toluene in a round-bottomed flask and then, stirred at 60° C. for 12 hours. After the reaction, distilled water was added thereto, the mixture was stirred for 30 minutes and extracted, and an organic layer therefrom was put through a silica gel column (hexane/dichloromethane=9:1 (v/v)) to obtain 14.70 g of Intermediate 2-15-1 (Yield=87%).

Step 2: Synthesis of Intermediate 2-15-2

15.50 g (38.92 mmol) of Intermediate 2-15-1 synthesized above, 7.15 g (42.81 mmol) of (2-nitrophenyl)-boronic acid, 16.14 g (116.75 mmol) of potassium carbonate, and 1.35 g (1.17 mmol) of tetrakis(triphenylphosphine)palladium (0) $(Pd(PPh_3)_4)$ were suspended in 150 ml of toluene and 70 ml of distilled water in a round-bottomed flask and then, refluxed and stirred for 12 hours. Subsequently, the mixture was extracted with dichloromethane and distilled water, and an organic layer therefrom was filtered with silica gel. After removing the organic solution, a solid product therein was recrystallized with dichloromethane and n-hexane to obtain 13.72 g (Yield=80%) of Intermediate 2-15-2.

Step 3: Synthesis of Intermediate 2-15-3

22.46 g (51.00 mmol) of Intermediate 2-15-2 synthesized above and 52.8 ml of triethyl phosphite were put in a round-bottomed flask, and after substituting nitrogen therein, the mixture was stirred for 12 hours at 160° C. After completing the reaction, 3 L of MeOH was added thereto, the obtained mixture was stirred and filtered, and a filtered solution therefrom was volatilized. A product therefrom was purified through column chromatography with hexane to obtain 10.42 g of Intermediate 2-15-3 (Yield=50%).

Step 4: Synthesis of Compound 2-15

Intermediate 2-15-3 and 1-iodo-3-phenylbenzene were used according to the same method as Step 1 of Synthesis Example 9 to synthesize Compound 2-15 (Yield=60%).

(LC/MS: theoretical value: 560.23 g/mol, measured value: 561.57 g/mol)

Synthesis Example 10: Synthesis of Compound 2-71

[Reaction Scheme 8]

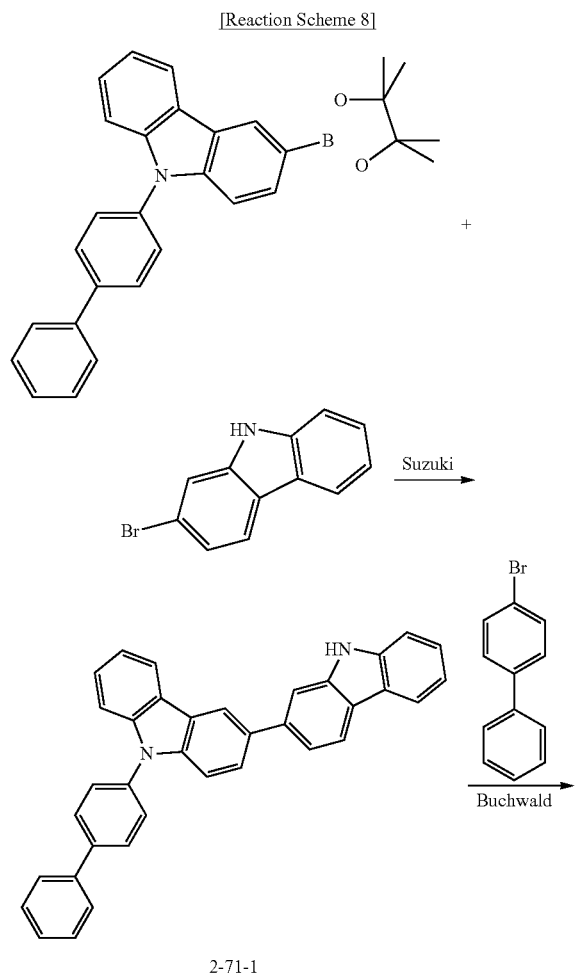

Step 1: Synthesis of Intermediate 2-71-1

18.23 g (40.94 mmol) of 9-(4-phenylphenyl)-3-(tetramethyl-1,3,2-dioxaborolane-2-yl)-9H-carbazole, 11.08 g (45.03 mmol) of 3-bromo-9H-carbazole, and 11.32 g (81.88 mmol) of potassium carbonate, and 1.42 g (1.23 mmol) of tetrakis(triphenylphosphine)palladium (0) (Pd(PPh$_3$)$_4$) were suspended in 180 ml of tetrahydrofuran (THF) and 75 ml of distilled water in a round-bottomed flask and then, refluxed and stirred for 12 hours. Subsequently, the mixture was extracted with dichloromethane and distilled water, and an organic layer therefrom was filtered with silica gel. The organic solution was then removed therefrom, and a solid product therefrom was recrystallized with dichloromethane and n-hexane to obtain 18.05 g of Intermediate 2-71-1 (Yield=91%).

Step 2: Synthesis of Compound 2-71

13.29 g (27.42 mmol) of Intermediate 2-71-1, 6.39 g (27.42 mmol) of 1-bromo-4-phenylbenzene, 0.25 g (0.274 mmol) of Pd$_2$(dba)$_3$, 0.133 g (0.274 mmol) of P(t-Bu)$_3$, and 3.95 g (41.13 mmol) of NaO(t-Bu) were suspended in 300 ml of toluene in a round-bottomed flask and then, stirred at 60° C. for 12 hours. After the reaction, distilled water was added thereto, the obtained mixture was stirred for 30 minutes and extracted, and an organic layer therefrom was put through a silica gel column (hexane/dichloromethane=9:1 (v/v)) to obtain 15.37 g of Compound 2-71 (Yield=88%).

LC-Mass (theoretical value: 636.26 g/mol, measured value: M+=637.40 g/mol)

Synthesis Example 11: Synthesis of Compound 2-73

The compound was synthesized by the method described in KR10-2017-0037277A.

Synthesis Example 12: Synthesis of Dopant Compound PtGD

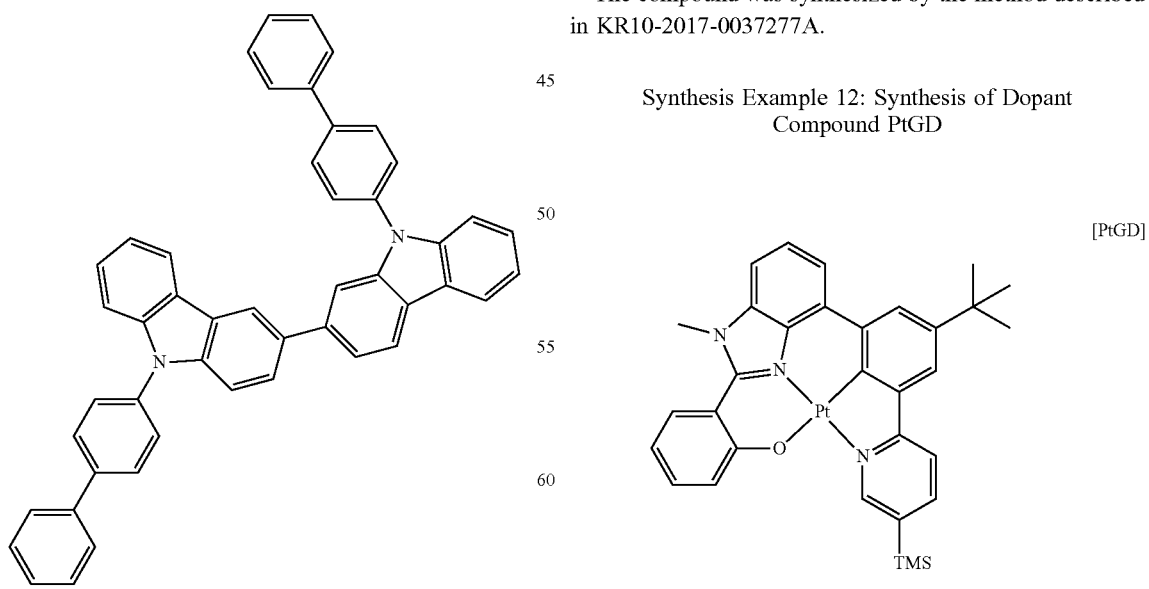

[PtGD]

The compound was synthesized by the method described in KR10-2018-0117919A.

Synthesis Example 13: Synthesis of Dopant Compound PhGD

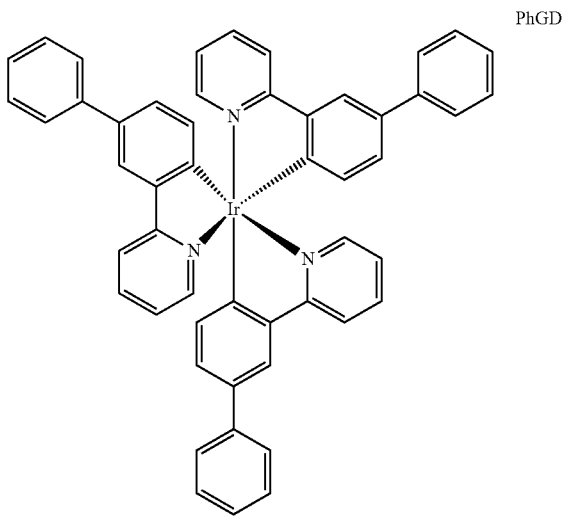

PhGD

The compound was synthesized by the method described in US 2004-0086743A.

Comparative Synthesis Example 1: Synthesis of Compound A-1

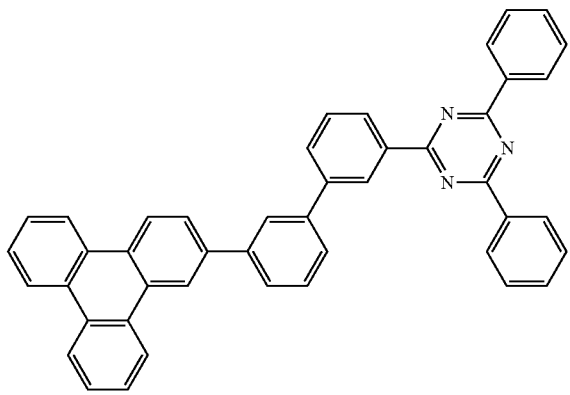

[Compound A-1]

The compound was synthesized by the method described in KR10-2017-0037277A.

Manufacture of Organic Light Emitting Diode

Example 1

A glass substrate coated with ITO (indium tin oxide) as a 1,500 Å-thick thin film was washed with distilled water. After washing with the distilled water, the glass substrate was ultrasonic wave-washed with isopropyl alcohol, acetone, or methanol and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 700 Å thick to form a hole transport layer. A 400 Å-thick hole transport auxiliary layer was formed on the hole transport layer by vacuum-depositing Compound C-1. A 400 Å-thick light emitting layer was formed on the hole transport auxiliary layer by simultaneously vacuum-depositing Compounds 1-65, 2-15, and 2-2 as a host doped with 15 wt % of PhGD as a dopant. Herein, Compounds 1-65, 2-15, and 2-2 were used in a weight ratio of 30:10:60, and in the other Examples and Comparative Examples, the ratios are described separately in the Tables below. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1,200 Å thick on the electron transport layer, manufacturing an organic light emitting diode.

The organic light emitting diode had a five-layered organic thin layer structure as follows:

a structure of ITO/Compound A (700 Å)/Compound B (50 Å)/Compound C (700 Å)/Compound C-1 (400 Å)/EML[Compound 1-65:2-15:2-2 [PhGD] (15 wt %)](400 Å)/Compound D: Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound C-1: N,N-di([1,1'-biphenyl]-4-yl)-7,7-dimethyl-7H-fluoreno[4,3-b]benzofuran-10-amine Compound D: 8-(4-(4,6-di(naphthalen-2-yl)-1,3,5-triazin-2-yl)phenyl)quinolone

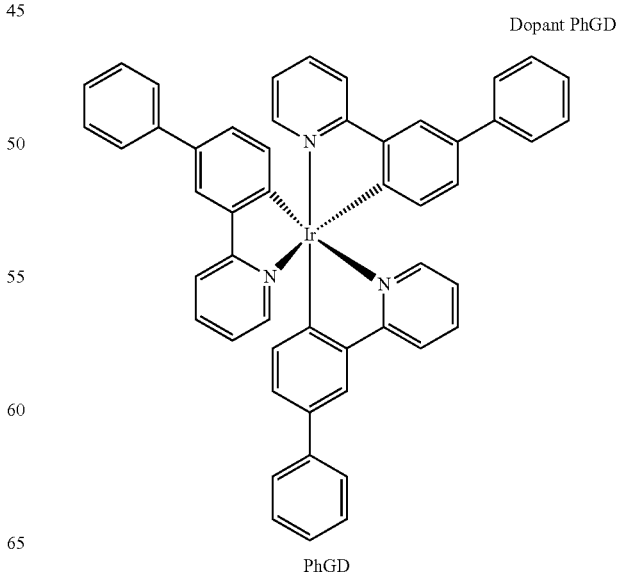

Dopant PhGD

PhGD

-continued

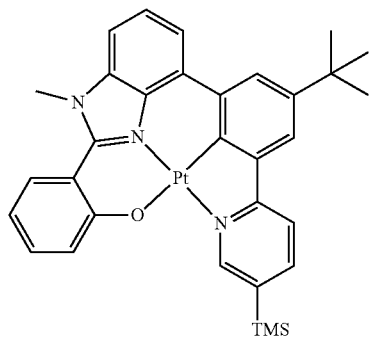

Dopant PtGD

Examples 2 to 4

Organic light emitting diodes were respectively manufactured according to the same method as Example 1 except for using the compositions including the hosts and dopants in Table 1 to Table 3.

Comparative Examples 1 to 3

Organic light emitting diodes were respectively manufactured according to the same method as Example 1 except for using the compositions including the hosts and dopants in Table 1 to Table 3.

Evaluation

Driving voltages and life-spans of the organic light emitting diodes according to Examples 1 to 4 and Comparative Examples 1 to 3 were measured.

Specific measurement methods are as follows, and the results are shown in Tables 1 to 3.

(1) Measurement of Life-Span

The results were obtained by measuring a time when current efficiency (cd/A) was decreased down to 97%, while luminance ($cd/m^2$) was maintained to be 9,000 $cd/m^2$.

(2) Measurement of Driving Voltage

A driving voltage of each diode was measured using a current-voltage meter (Keithley 2400) at 15 $mA/cm^2$ to obtain the result. Table 1 shows relative ratios using that of Comparative Example as a reference.

TABLE 1

| | First host | Second host | Third host | First host:Second host:Third host ratio (wt:wt) | Dopant | Driving voltage (V) | Life-span ratio (T97) (%) |
|---|---|---|---|---|---|---|---|
| Ex. 1 | 1-65 | 2-15 | 2-2 | 30:10:60 | PhGD, 15% | 4.1 | 158% |
| Comp. Ex. 1 | 1-65 | 2-15 | — | 30:70:0 | PhGD, 15% | 3.9 | 100% |

TABLE 2

| | First host | Second host | Third host | First host:Second host:Third host ratio (wt:wt) | Dopant | Driving voltage (V) | Life-span ratio (T97) (%) |
|---|---|---|---|---|---|---|---|
| Ex. 2 | 1-66 | 2-15 | 2-2 | 30:10:60 | PhGD, 15% | 4.1 | 113% |
| Comp. Ex. 2 | 1-66 | — | 2-2 | 30:0:70 | PhGD, 15% | 4.5 | 100% |

TABLE 3

| | First host | Second host | Third host | First host:Second host:Third host ratio (wt:wt) | Dopant | Driving voltage (V) | Life-span ratio (T97) (%) |
|---|---|---|---|---|---|---|---|
| Ex. 3 | 1-15 | 2-2 | 2-72 | 30:30:40 | PtGD, 15% | 3.8 | 429% |
| Ex. 4 | 1-63 | 2-2 | 2-71 | 30:25:45 | PtGD, 15% | 4.0 | 429% |
| Comp. Ex. 3 | A-1 | 2-2 | 2-73 | 30:60:10 | PtGD, 15% | 4.0 | 100% |

Referring to Tables 1 to 3, the organic light emitting diodes according to Examples 1 to 4 exhibited a significant improvement in life-span while maintaining similar driving voltages as compared with the organic light emitting diodes according to Comparative Examples 1 to 3.

One or more embodiments may provide a composition for an organic optoelectronic device capable of realizing an organic optoelectronic device having high efficiency and long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:

a first compound;

a second compound; and a third compound, wherein:

the first compound, the second compound, and the third compound are different from each other, the first compound, the second compound, and the third compound are a phosphorescent host, the composition is a green light emitting composition or a red light emitting composition, the first compound is represented by Chemical Formula I, the second compound is represented by one of Chemical Formulae II-1 to II-7 or one of Chemical Formulae III-1 to III-24, and the third compound is represented by one of Chemical Formulae II-1 to II-7 or one of Chemical Formulae III-1 to III-24:

[Chemical Formula I]

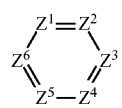

wherein, in Chemical Formula I, $Z^1$ is N or C-$L^1$-$R^1$, $Z^2$ is N or C-$L^2$-$R^2$, $Z^3$ is N or C-$L^3$-$R^3$, $Z^4$ is N or C-$L^4$-$R^4$, $Z^5$ is N or C-$L^5$-$R^5$, $Z^6$ is N or C-$L^6$-$R^6$, only two or three of $Z^1$ to $Z^6$ are N, $L^1$ to $L^6$ are independently a single bond, a substituted or unsubstituted C6 to C20 arylene group, a substituted or unsubstituted C2 to C20 heterocyclic group, or a combination thereof, $R^1$ to $R^6$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^1$ to $R^6$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, and when $R^1$ to $R^6$ are separate, at least one of $R^1$ to $R^6$ is a substituted or unsubstituted C2 to C30 heterocyclic group;

[Chemical Formula II-1]

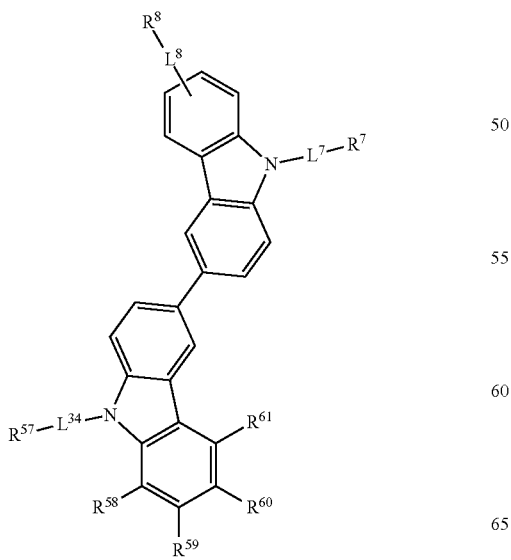

[Chemical Formula II-2]

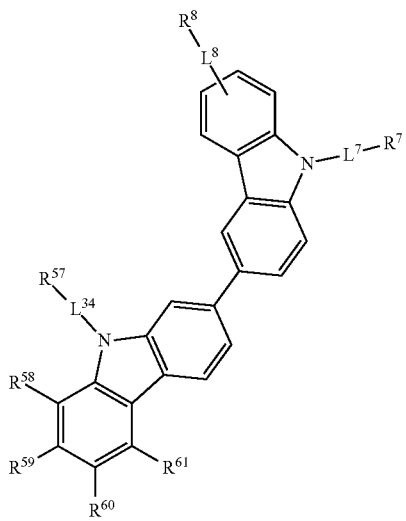

[Chemical Formula II-3]

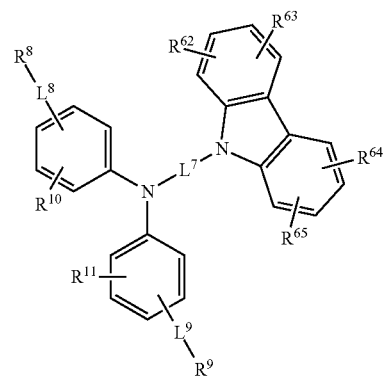

[Chemical Formula II-4]

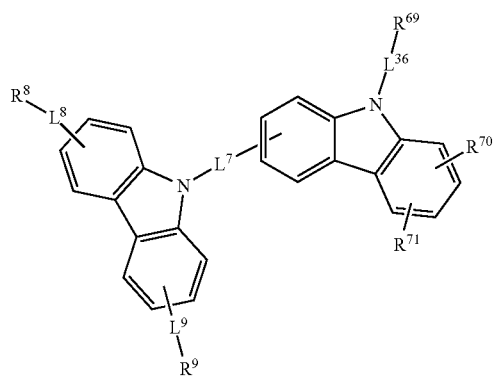

-continued

[Chemical Formula II-5]

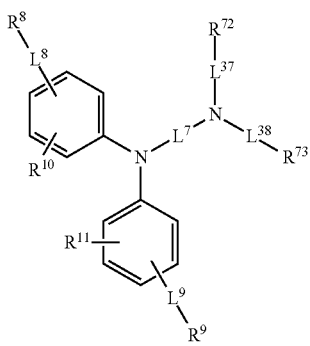

[Chemical Formula II-6]

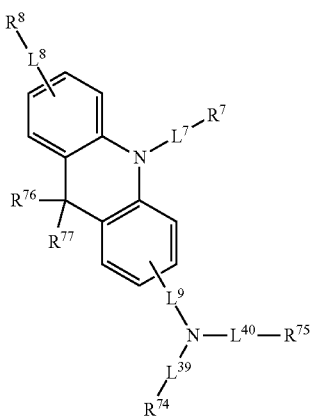

[Chemical Formula II-7]

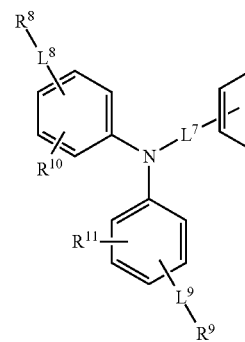

wherein, in Chemical Formulae II-1 to II-7, $X^9$ is O, S, or $CR^qR^r$, $L^7$ to $L^9$, $L^{34}$, and $L^{36}$ to $L^{40}$ are independently a single bond, a substituted or unsubstituted C6 to C20 arylene group, a substituted or unsubstituted C2 to C20 heterocyclic group, or a combination thereof, $R^q$, $R^r$, $R^7$ to $R^{11}$, $R^{57}$ to $R^{65}$, and $R^{69}$ to $R^{81}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof, $R^8$ and $R^{10}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^9$ and $R^{11}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^q$ and $R^r$ are separate or adjacent groups thereof are linked with each other to form a substituted or unsubstituted aromatic monocyclic or polycyclic ring, $R^{58}$ to $R^{61}$ are separate or adjacent groups thereof are linked with each other to form a substituted or unsubstituted aromatic monocyclic or polycyclic ring, and $R^{78}$ to $R^{81}$ are separate or adjacent groups thereof are linked with each other to form a substituted or unsubstituted aromatic monocyclic or polycyclic ring,

[Chemical Formula III-1]

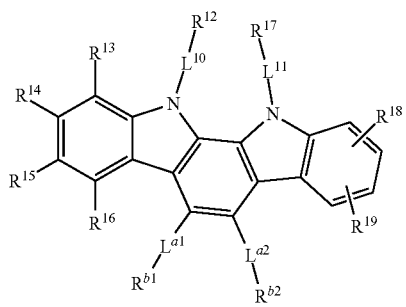

[Chemical Formula III-2]

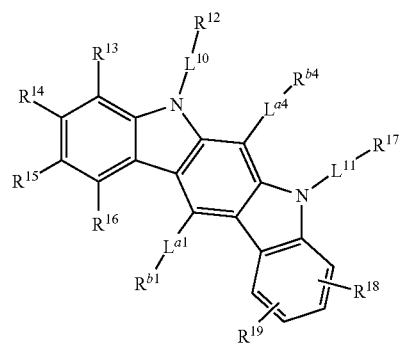

[Chemical Formula III-3]

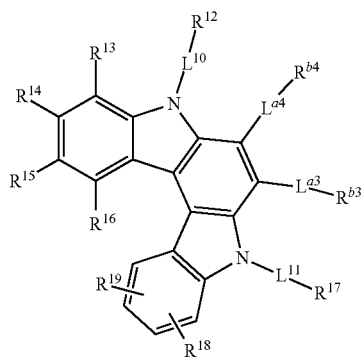

-continued
[Chemical Formula III-4]
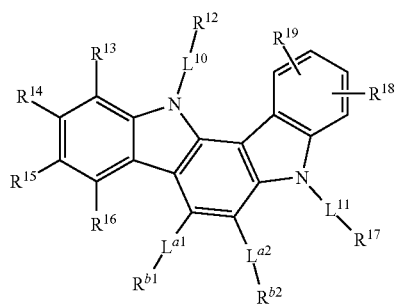
[Chemical Formula III-5]
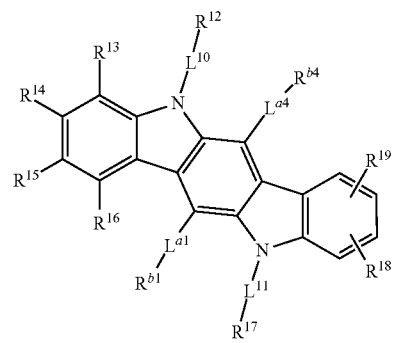
[Chemical Formula III-6]
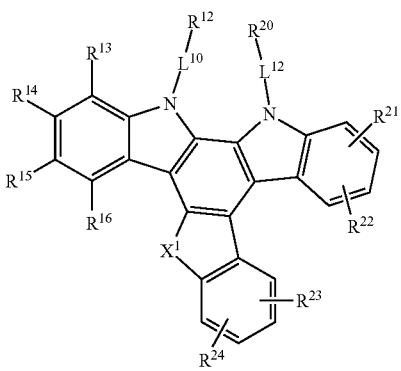
[Chemical Formula III-7]
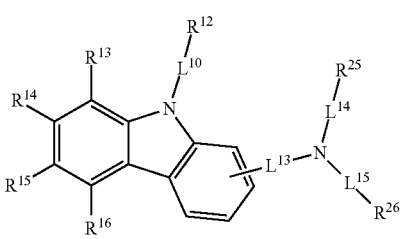
[Chemical Formula III-8]
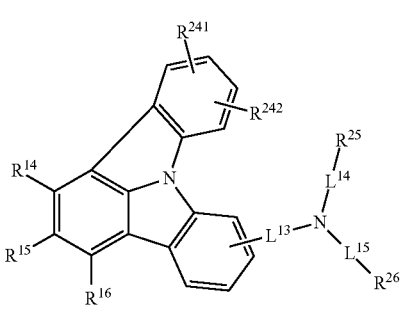
-continued
[Chemical Formula III-9]
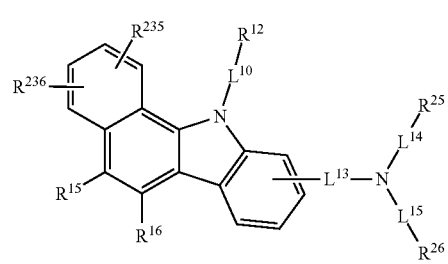
[Chemical Formula III-10]
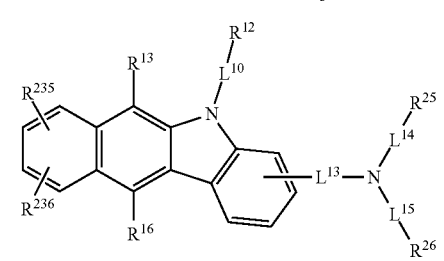
[Chemical Formula III-11]
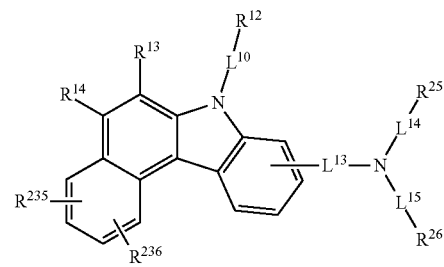
[Chemical Formula III-12]
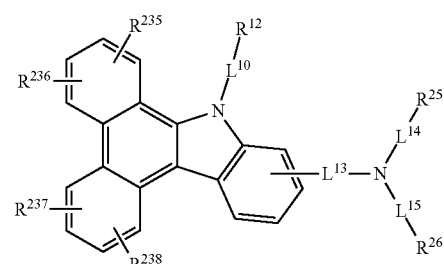
[Chemical Formula III-13]
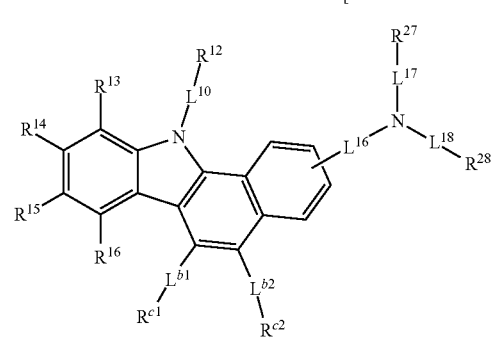

[Chemical Formula III-14]
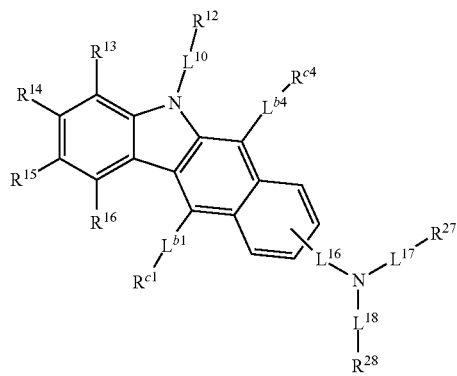
[Chemical Formula III-15]
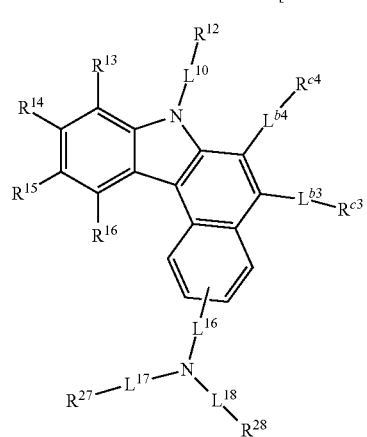
[Chemical Formula III-16]
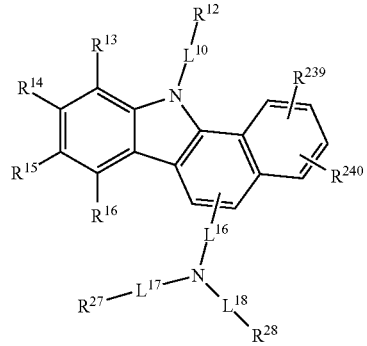
[Chemical Formula III-17]
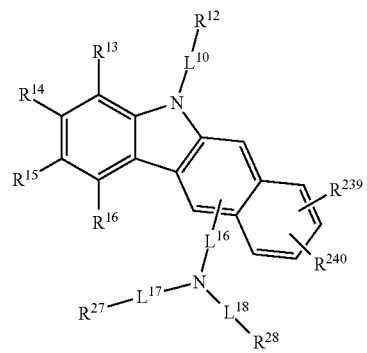
[Chemical Formula III-18]
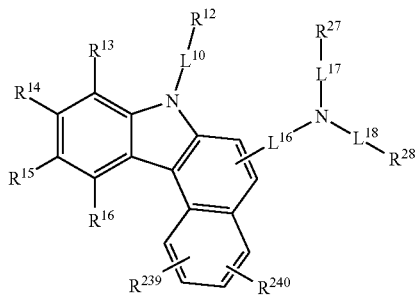
[Chemical Formula III-19]
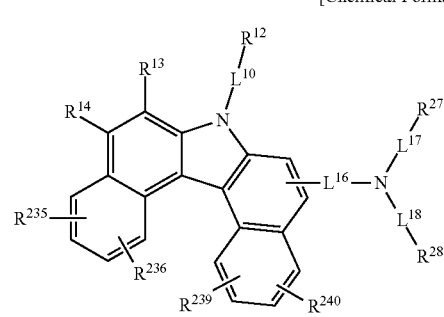
[Chemical Formula III-20]
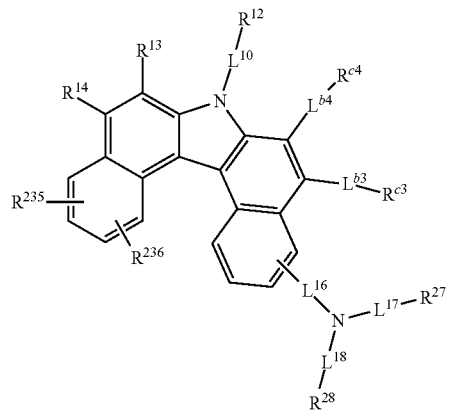
[Chemical Formula III-21]
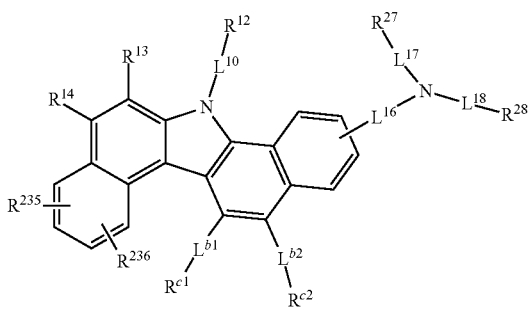

-continued

[Chemical Formula III-22]

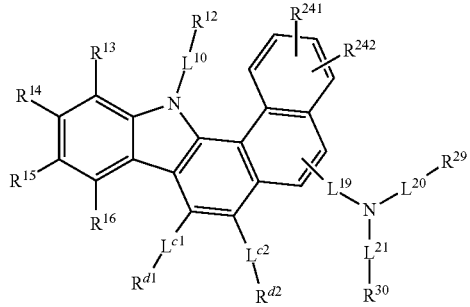

[Chemical Formula III-23]

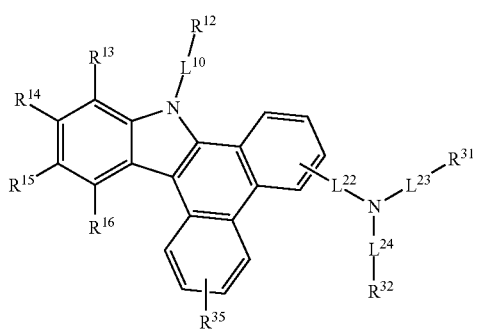

[Chemical Formula III-24]

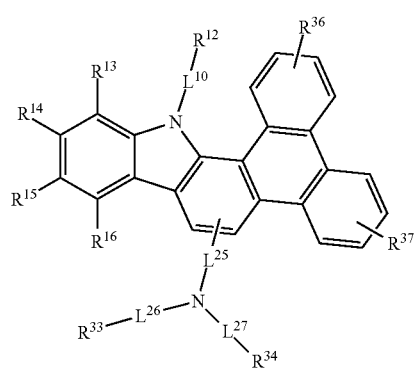

wherein, in Chemical Formulae III-1 to III-24,
$X^1$ is O, S, or $NR^a$,
$L^{a1}$ to $L^{a4}$, $L^{b1}$ to $L^{b4}$, $L^{c1}$, $L^{c2}$, and $L^{10}$ to $L^{27}$ are independently a single bond, a substituted or unsubstituted C6 to C20 arylene group, a substituted or unsubstituted C2 to C20 heterocyclic group, or a combination thereof,
$R^a$, $R^{b1}$ to $R^{b4}$, $R^{c1}$ to $R^{c4}$, $R^{d1}$, $R^{d2}$, $R^{12}$ to $R^{22}$, and $R^{25}$ to $R^{37}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and
$R^{235}$ to $R^{242}$ are independently hydrogen, deuterium, a substituted or unsubstituted C1 to C10 alkyl group, a substituted or unsubstituted C6 to C20 aryl group, a halogen, a cyano group, or a combination thereof.

2. The composition as claimed in claim 1, wherein the first compound represented by Chemical Formula I is represented by one of Chemical Formula I-1 to Chemical Formula I-4:

[Chemical Formula I-1]

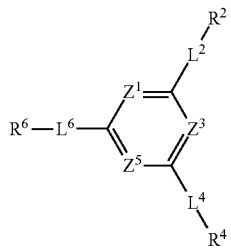

[Chemical Formula I-2]

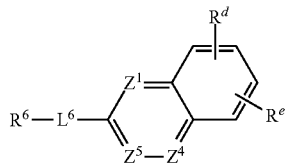

[Chemical Formula I-3]

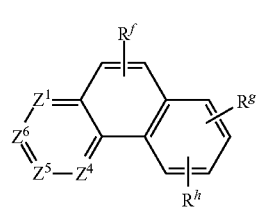

[Chemical Formula I-4]

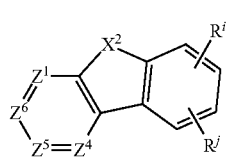

wherein, in Chemical Formula I-1 to Chemical Formula I-4,
$X^2$ is O or S,
$Z^1$ is N or $C-L^1-R^1$,
$Z^3$ is N or $C-L^3-R^3$,
$Z^4$ is N or $C-L^4-R^4$,
$Z^5$ is N or $C-L^5-R^5$,
$Z^6$ is N or $C-L^6-R^6$,
two or three of $Z^1$, $Z^3$, and $Z^5$ are N,
two or three of $Z^1$, $Z^4$, and $Z^5$ are N,
two or three of $Z^1$, and $Z^4$ to $Z^6$ are N,
$L^1$ to $L^6$ are independently a single bond or a substituted or unsubstituted C6 to C20 arylene group, a substituted or unsubstituted C2 to C20 heterocyclic group, or a combination thereof,
$R^d$ to $R^j$ and $R^1$ to $R^6$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and
at least one of $R^2$, $R^4$, and $R^6$ of Chemical Formula I-1 is a substituted or unsubstituted C2 to C30 heterocyclic group.

3. The composition as claimed in claim 2, wherein:
the first compound is represented by Chemical Formula I-1, and
Chemical Formula I-1 is represented by one of Chemical Formula I-1A to Chemical Formula I-1C:

[Chemical Formula I-1A]

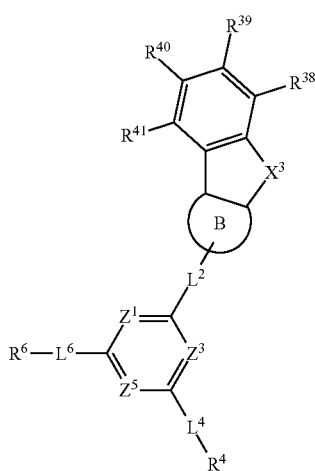

[Chemical Formula I-1B]

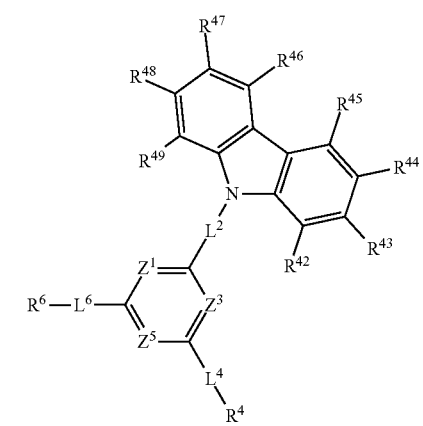

[Chemical Formula I-1C]

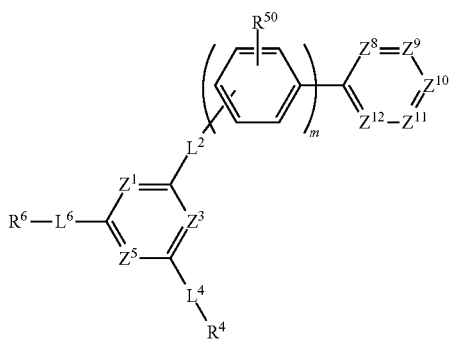

wherein, in Chemical Formula I-1A to Chemical Formula I-1C,
$X^3$ is O, S, or $NR^k$,
$Z^1$, $Z^3$, and $Z^5$ are independently N or CH,
two or three of $Z^1$, $Z^3$, and $Z^5$ are N,
$Z^8$ is N or $C-L^{28}-R^{51}$,
$Z^9$ is N or $C-L^{29}-R^{52}$,
$Z^{10}$ is N or $C-L^{30}-R^{53}$,
$Z^{11}$ is N or $C-L^{31}-R^{54}$,
$Z^{12}$ is N or $C-L^{32}-R^{55}$,
at least one of $Z^8$ to $Z^{12}$ is N,
$L^2$, $L^4$, $L^6$, and $L^{28}$ to $L^{32}$ are independently a single bond, a substituted or unsubstituted C6 to C20 arylene group, a substituted or unsubstituted C2 to C20 heterocyclic group, or a combination thereof, $R^k$, $R^4$, and $R^6$ are independently a substituted or unsubstituted C6 to C30 aryl group, a substituted or unsubstituted C2 to C30 heterocyclic group, or a combination thereof, $R^{38}$ to $R^{55}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{38}$ to $R^{41}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{42}$ to $R^{45}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{46}$ to $R^{49}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{51}$ to $R^{55}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, m is an integer of 0 to 3, and
B is a moiety represented by Chemical Formula B-1 or B-2,

[Chemical Formula B-1]

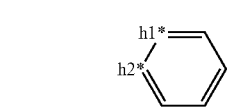

[Chemical Formula B-2]

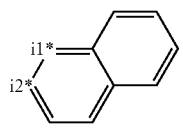

wherein, in Chemical Formula B-1 and Chemical Formula B-2, h1* and h2* and i1* and i2* are each a linking C.

4. The composition as claimed in claim 3, wherein:
the first compound is represented by Chemical Formula I-1A, and
Chemical Formula I-1A is represented by one of Chemical Formulae I-1A-1 to I-1A-6:

[Chemical Formula I-1A-1]
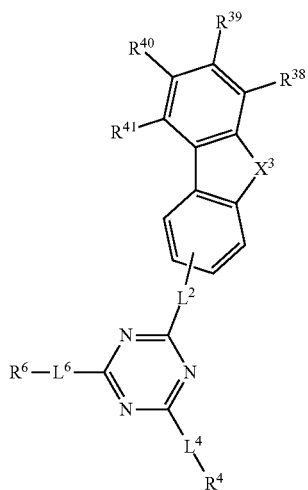
[Chemical Formula I-1A-2]
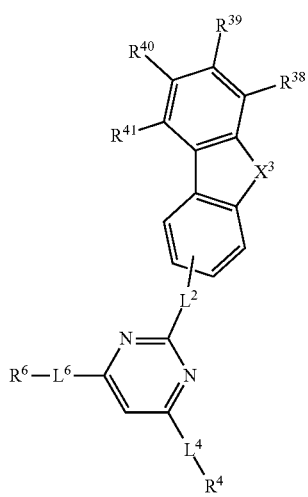
[Chemical Formula I-1A-3]
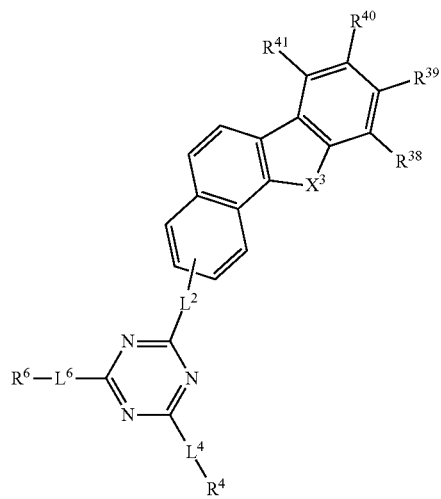
[Chemical Formula I-1A-4]
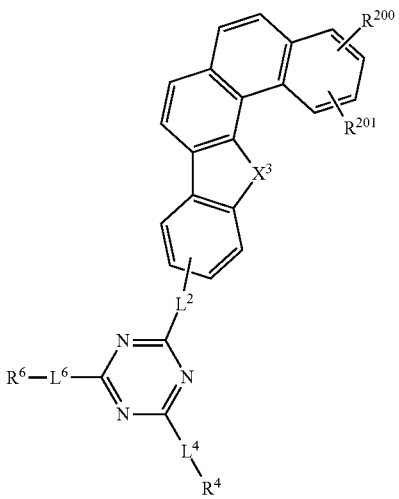
[Chemical Formula I-1A-5]
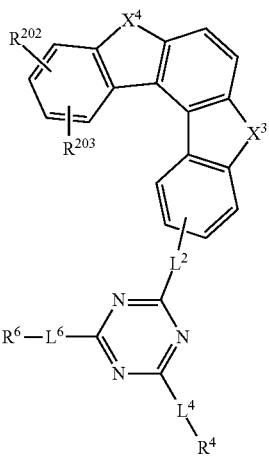
[Chemical Formula I-1A-6]
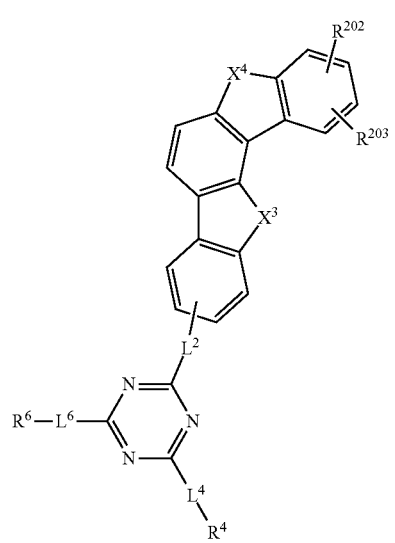
wherein, in Chemical Formulae I-1A-1 to I-1A-6,
$X^3$ is O, S, or $NR^k$,
$X^4$ is O, S, or $NR^l$,
$L^2$, $L^4$, and $L^6$ are independently a single bond, a substituted or unsubstituted C6 to C20 arylene group, a substituted or unsubstituted C2 to C20 heterocyclic group, or a combination thereof, $R^k$, $R^l$, $R^4$, and $R^6$ are independently a substituted or unsubstituted C6 to C30 aryl group, a substituted or unsubstituted C2 to C30 heterocyclic group, or a combination thereof, $R^{38}$ to $R^{41}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{200}$ to $R^{203}$ are independently hydrogen, deuterium, a substituted or unsubstituted C1 to C10 alkyl group, a substituted or unsubstituted C6 to C20 aryl group, a halogen, a cyano group, or a combination thereof.

5. The composition as claimed in claim 3, wherein:

the first compound is represented by Chemical Formula I-1B, and

Chemical Formula I-1B is represented by one of Chemical Formula I-1B-1 to Chemical Formula I-1B-8:

[Chemical Formula I-1B-1]

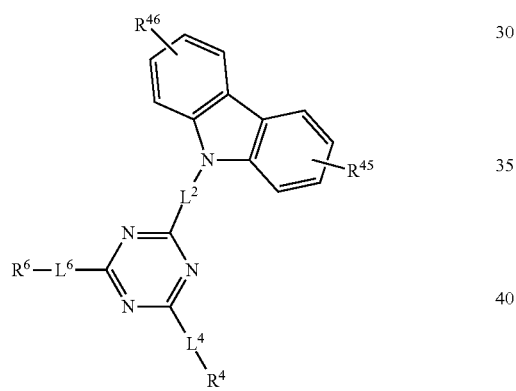

[Chemical Formula I-1B-2]

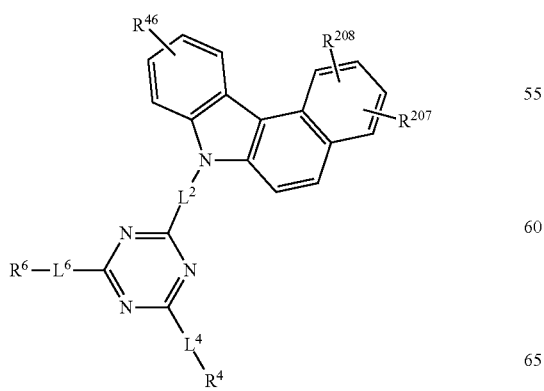

[Chemical Formula I-1B-3]

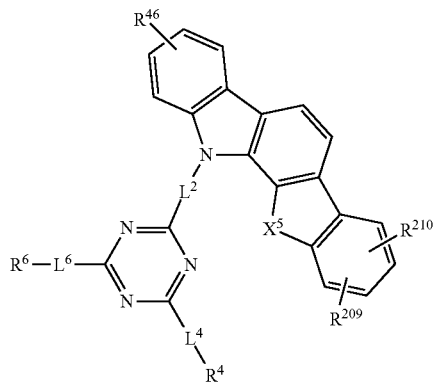

[Chemical Formula I-1B-4]

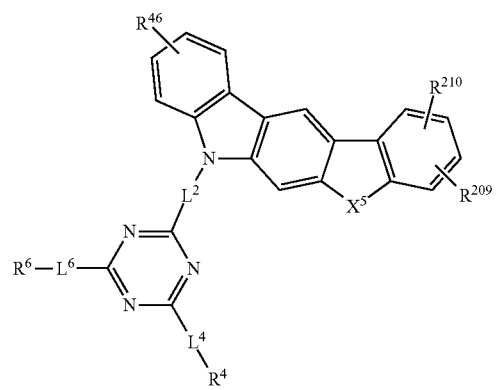

[Chemical Formula I-1B-5]

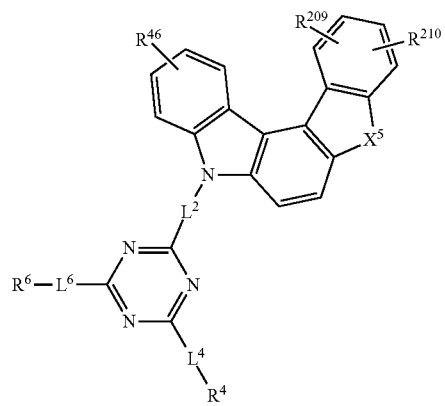

[Chemical Formula I-1B-6]

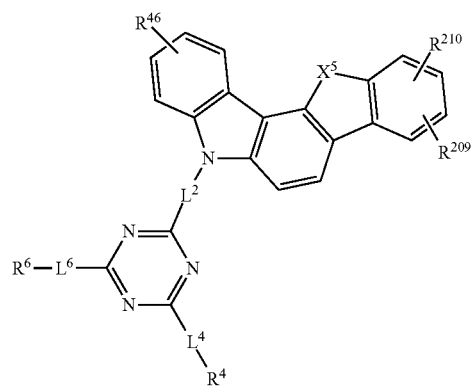

[Chemical Formula I-1B-7]

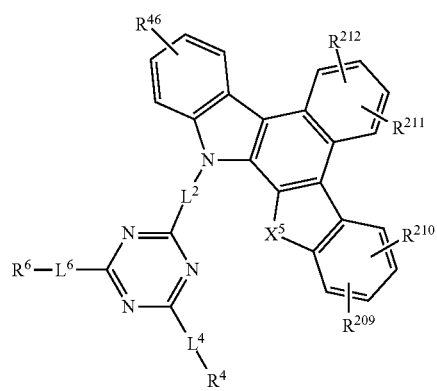

[Chemical Formula I-1B-8]

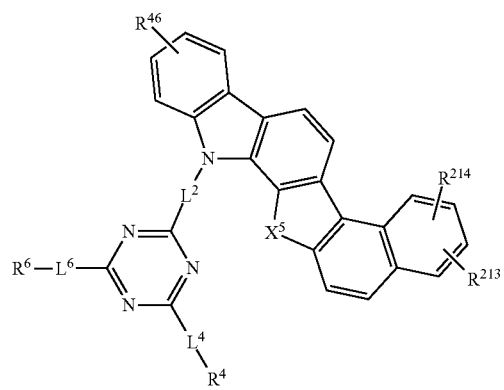

wherein, in Chemical Formula I-1B-1 to Chemical Formula I-1B-8, $X^5$ is O, S, $CR^{205}R^{206}$, or $NR^m$, $L^2$, $L^4$, and $L^6$ are independently a single bond, a substituted or unsubstituted C6 to C20 arylene group, a substituted or unsubstituted C2 to C20 heterocyclic group, or a combination thereof, $R^m$, $R^4$, and $R^6$ are independently a substituted or unsubstituted C6 to C30 aryl group, a substituted or unsubstituted C2 to C30 heterocyclic group, or a combination thereof, $R^{45}$ and $R^{46}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{205}$ to $R^{214}$ are independently hydrogen, deuterium, a substituted or unsubstituted C1 to C10 alkyl group, a substituted or unsubstituted C6 to C20 aryl group, a halogen, a cyano group, or a combination thereof.

6. The composition as claimed in claim 2, wherein:

the first compound is represented by Chemical Formula I-2, and

Chemical Formula I-2 is represented by Chemical Formula I-2A or Chemical Formula I-2B:

[Chemical Formula I-2A]

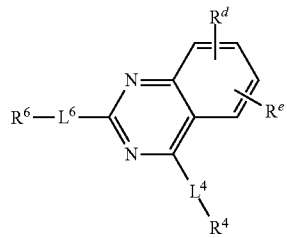

[Chemical Formula I-2B]

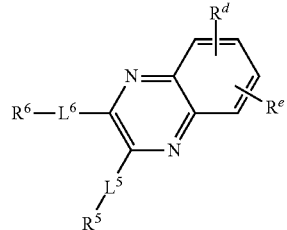

wherein, in Chemical Formula I-2A and Chemical Formula I-2B, $L^4$ to $L^6$ are independently a single bond, a substituted or unsubstituted C6 to C20 arylene group, a substituted or unsubstituted C2 to C20 heterocyclic group, or a combination thereof, $R^4$ to $R^6$ are independently a substituted or unsubstituted C6 to C30 aryl group, a substituted or unsubstituted C2 to C30 heterocyclic group, or a combination thereof, and $R^d$ and $R^e$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

7. The composition as claimed in claim 6, wherein:

the first compound is represented by Chemical Formula I-2A, and

Chemical Formula I-2A is represented by one of Chemical Formulae I-2A-1 to I-2A-4:

[Chemical Formula I-2A-1]

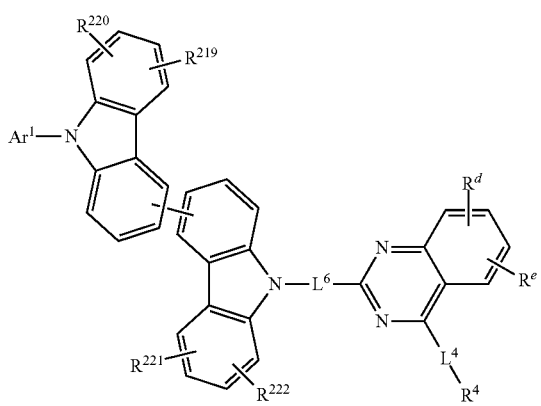

-continued

[Chemical Formula I-2A-2]

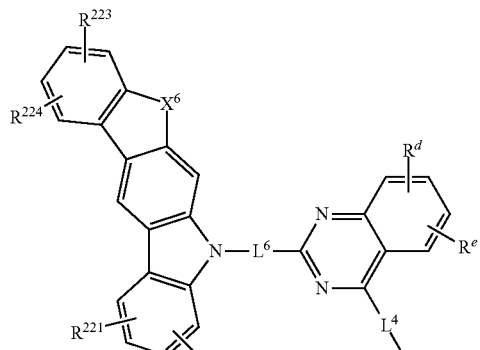

[Chemical Formula I-2A-3]

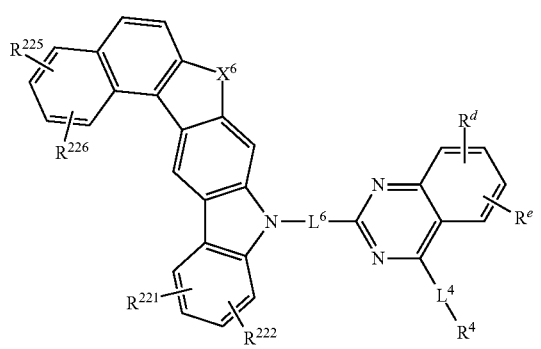

[Chemical Formula I-2A-4]

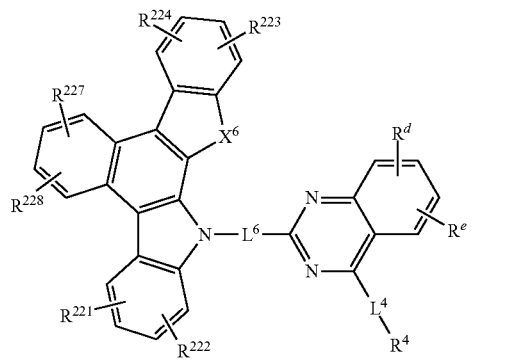

wherein, in Chemical Formulae I-2A-1 to I-2A-4,
$X^6$ is O, S, or $NR''$,
$Ar^1$ is a substituted or unsubstituted C6 to C30 aryl group, a substituted or unsubstituted C2 to C30 heterocyclic group, or a combination thereof,
$L^4$ and $L^6$ are independently a single bond, a substituted or unsubstituted C6 to C20 arylene group, a substituted or unsubstituted C2 to C20 heterocyclic group, or a combination thereof,
$R''$ and $R^4$ are independently a substituted or unsubstituted C6 to C30 aryl group, a substituted or unsubstituted C2 to C30 heterocyclic group, or a combination thereof,
$R^d$ and $R^e$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and
$R^{219}$ to $R^{228}$ are independently hydrogen, deuterium, a substituted or unsubstituted C1 to C10 alkyl group, a substituted or unsubstituted C6 to C20 aryl group, a halogen, a cyano group, or a combination thereof.

8. The composition as claimed in claim 6, wherein:
the first compound is represented by Chemical Formula I-2B, and
Chemical Formula I-2B is represented by one of Chemical Formula I-2B-1 to Chemical Formula I-2B-3:

[Chemical Formula I-2B-1]

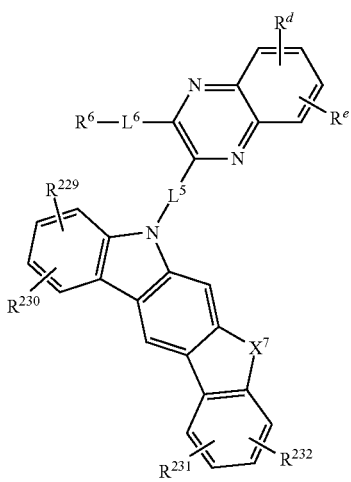

[Chemical Formula I-2B-2]

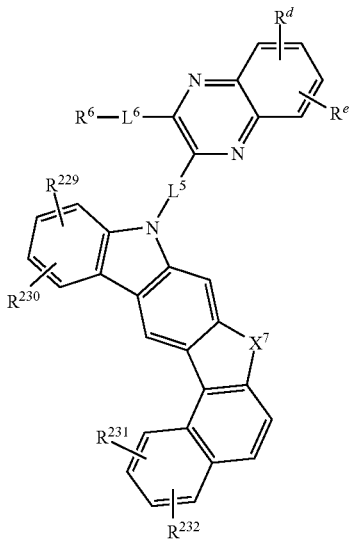

155
-continued

[Chemical Formula I-2B-3]

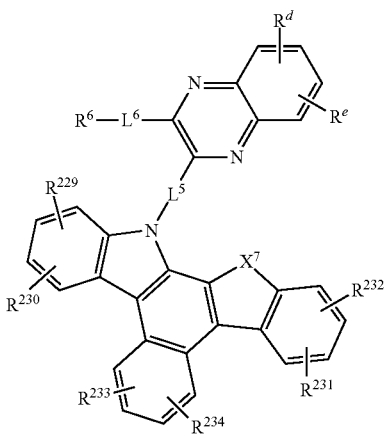

wherein, in Chemical Formula I-2B-1 to Chemical Formula I-2B-3, $X^7$ is O, S, or $NR^o$, $L^5$ and $L^6$ are independently a single bond, a substituted or unsubstituted C6 to C20 arylene group, a substituted or unsubstituted C2 to C20 heterocyclic group, or a combination thereof, $R^o$ and $R^6$ are independently a substituted or unsubstituted C6 to C30 aryl group, a substituted or unsubstituted C2 to C30 heterocyclic group, or a combination thereof, $R^d$ and $R^e$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{229}$ to $R^{234}$ are independently hydrogen, deuterium, a substituted or unsubstituted C1 to C10 alkyl group, a substituted or unsubstituted C6 to C20 aryl group, a halogen, a cyano group, or a combination thereof.

9. The composition as claimed in claim 2, wherein:

the first compound is represented by Chemical Formula I-3, and

Chemical Formula I-3 is represented by Chemical Formula I-3A or Chemical Formula I-3B:

[Chemical Formula I-3A]

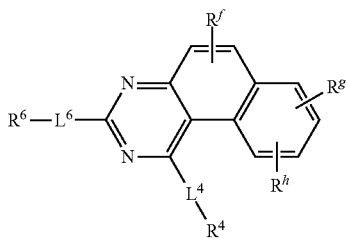

156
-continued

[Chemical Formula I-3B]

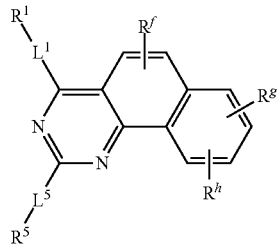

wherein, in Chemical Formula I-3A and Chemical Formula I-3B, $L^1$ and $L^4$ to $L^6$ are independently a single bond, a substituted or unsubstituted C6 to C20 arylene group, a substituted or unsubstituted C2 to C20 heterocyclic group, or a combination thereof, $R^1$ and $R^4$ to $R^6$ are independently a substituted or unsubstituted C6 to C30 aryl group, a substituted or unsubstituted C2 to C30 heterocyclic group, or a combination thereof, and $R^f$, $R^g$, and $R^h$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

10. The composition as claimed in claim 9, wherein:

the first compound is represented by Chemical Formula I-3A, and

Chemical Formula I-3A is represented by one of Chemical Formulae I-3A-1 to I-3A-3:

[Chemical Formula I-3A-1]

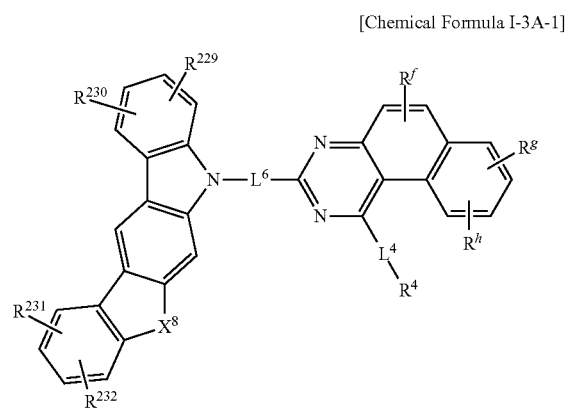

[Chemical Formula I-3A-2]

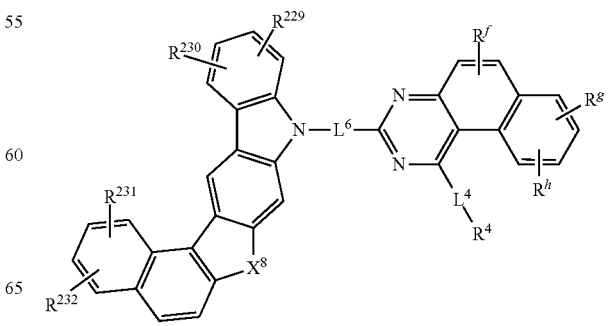

[Chemical Formula I-3A-3]

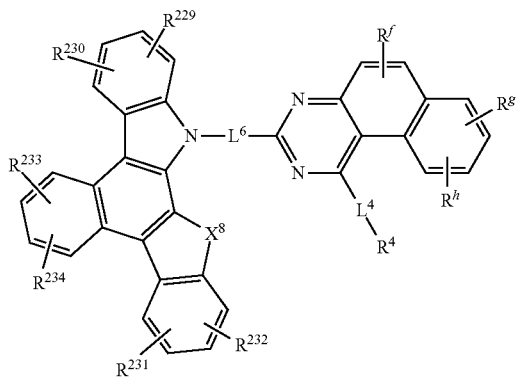

wherein, in Chemical Formula I-3A-1 to Chemical Formula I-3A-3, $X^8$ is O, S, or $NR^p$, $L^4$ and $L^6$ are independently a single bond, a substituted or unsubstituted C6 to C20 arylene group, a substituted or unsubstituted C2 to C20 heterocyclic group, or a combination thereof, $R^p$ and $R^4$ are independently a substituted or unsubstituted C6 to C30 aryl group, a substituted or unsubstituted C2 to C30 heterocyclic group, or a combination thereof, $R^f$, $R^g$, and $R^h$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{229}$ to $R^{234}$ are independently hydrogen, deuterium, a substituted or unsubstituted C1 to C10 alkyl group, a substituted or unsubstituted C6 to C20 aryl group, a halogen, a cyano group, or a combination thereof.

11. The composition as claimed in claim 9, wherein:
the first compound is represented by Chemical Formula I-3B, and
Chemical Formula I-3B is represented by one of Chemical Formulae I-3B-1 to I-3B-3:

[Chemical Formula I-3B-1]

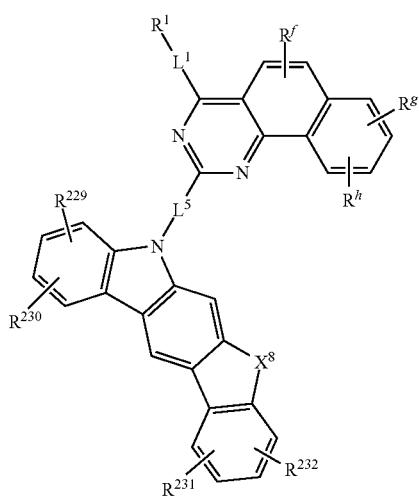

[Chemical Formula I-3B-2]

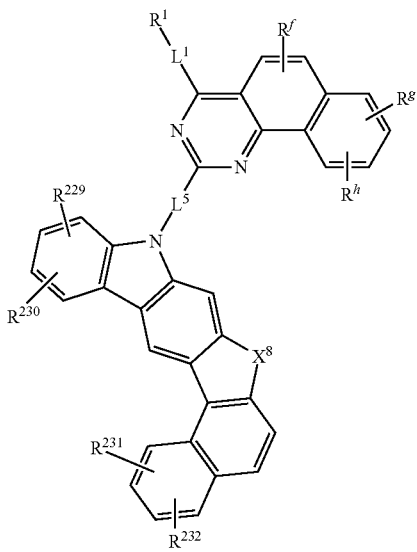

[Chemical Formula I-3B-3]

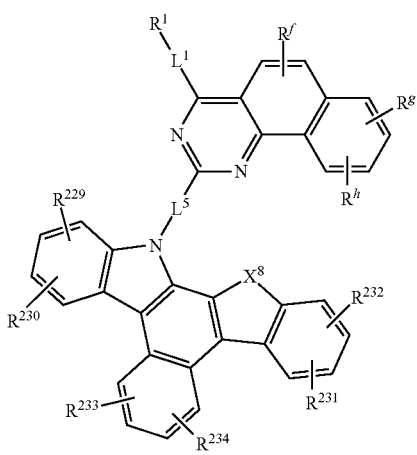

wherein, in Chemical Formula I-3B-1 to Chemical Formula I-3B-3, $X^8$ is O, S, or $NR^p$, $L^1$ and $L^5$ are independently a single bond, a substituted or unsubstituted C6 to C20 arylene group, a substituted or unsubstituted C2 to C20 heterocyclic group, or a combination thereof, $R^p$ and $R^1$ are independently a substituted or unsubstituted C6 to C30 aryl group, a substituted or unsubstituted C2 to C30 heterocyclic group, or a combination thereof, $R^f$, $R^g$, and $R^h$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{229}$ to $R^{234}$ are independently hydrogen, deuterium, a substituted or unsubstituted C1 to C10 alkyl group, a substituted or unsubstituted C6 to C20 aryl group, a halogen, a cyano group, or a combination thereof.

12. The composition as claimed in claim 2, wherein:
the first compound is represented by Chemical Formula I-4, and Chemical Formula I-4 is represented by Chemical Formula I-4A or Chemical Formula I-4B:

[Chemical Formula I-4A]

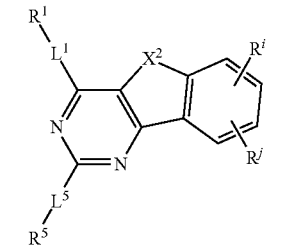

[Chemical Formula I-4B]

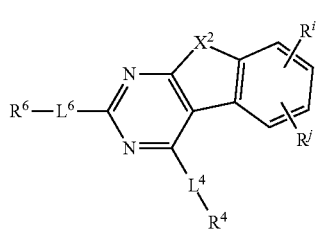

wherein, in Chemical Formula I-4A and Chemical Formula I4B, $X^2$ is O or S, $L^1$ and $L^4$ to $L^6$ are independently a single bond, a substituted or unsubstituted C6 to C20 arylene group, a substituted or unsubstituted C2 to C20 heterocyclic group, or a combination thereof, $R^1$ and $R^5$ are independently a substituted or unsubstituted C6 to C30 aryl group, a substituted or unsubstituted C2 to C30 heterocyclic group, or a combination thereof, and $R^i$, $R^j$, $R^4$, and $R^6$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

13. The composition as claimed in claim 12, wherein:

the first compound is represented by Chemical Formula I-4A, and

Chemical Formula I-4A is represented by one of Chemical Formula I-4A-1 to Chemical Formula I-4A-4:

[Chemical Formula I-4A-1]

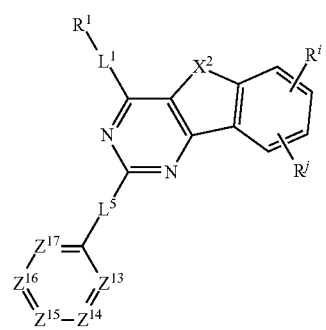

[Chemical Formula I-4A-2]

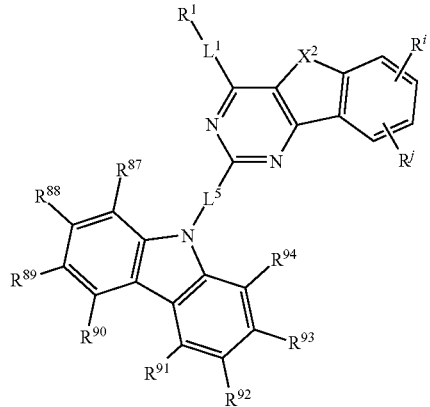

[Chemical Formula I-4A-3]

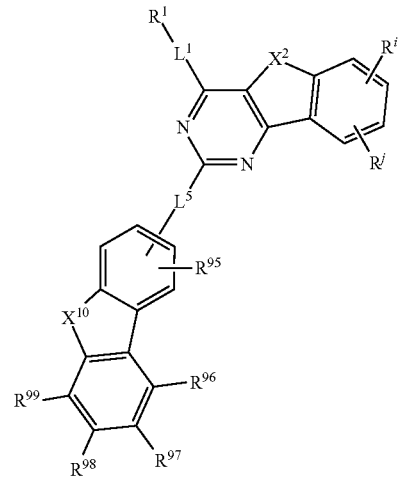

[Chemical Formula I-4A-4]

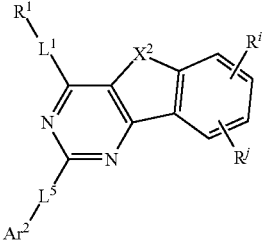

wherein, in Chemical Formula I-4A-1 to Chemical Formula I-4A-4, $X^2$ is O or S, $X^{10}$ is N, S, or $NR^s$, $Z^{13}$ is N or $C\text{-}L^{41}\text{-}R^{82}$, $Z^{14}$ is N or $C\text{-}L^{42}\text{-}R^{83}$, $Z^{15}$ is N or $C\text{-}L^{43}\text{-}R^{84}$, $Z^{16}$ is N or $C\text{-}L^{44}\text{-}R^{85}$, $Z^{17}$ is N or $C\text{-}L^{45}\text{-}R^{86}$, at least one of $Z^{13}$ to $Z^{17}$ is N, $L^1$, $L^5$, and $L^{41}$ to $L^{45}$ are independently a single bond, a substituted or unsubstituted C6 to C20 arylene group, a substituted or unsubstituted C2 to C20 heterocyclic group, or a combination thereof, $R^i$, $R^j$, and $R^{82}$ to $R^{99}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^1$ and $R^s$ are independently a substituted or unsubstituted C6 to C30 aryl group, a substituted or unsubstituted C2 to C30 heterocyclic group, or a combination thereof, and $Ar^2$ is a substituted or unsubstituted C6 to C30 aryl group.

14. The composition as claimed in claim 12, wherein:

the first compound is represented by Chemical Formula I-4B, and

Chemical Formula I-4B is represented by one of Chemical Formula I-4B-1 to Chemical Formula I-4B-4:

[Chemical Formula I-4B-1]

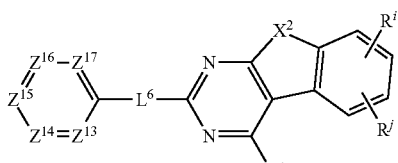

[Chemical Formula I-4B-2]

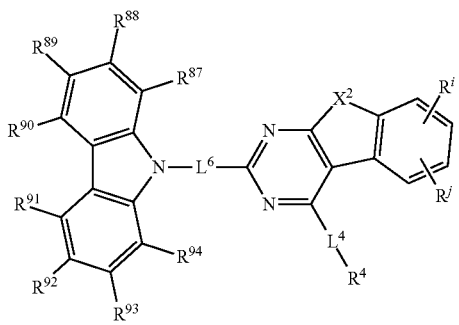

[Chemical Formula I-4B-3]

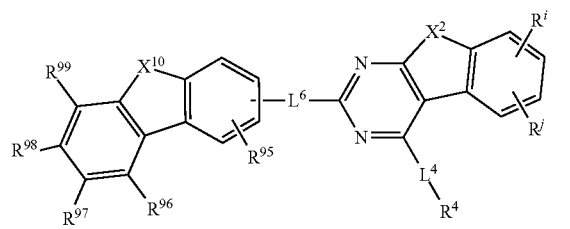

[Chemical Formula I-4B-4]

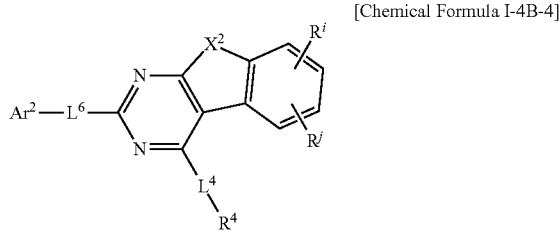

wherein, in Chemical Formula I-4B-1 to Chemical Formula I-4B-4, $X^2$ is O or S, $X^{10}$ is O, S, or $NR^s$, $Z^{13}$ is N or $C-L^{41}-R^{82}$, $Z^{14}$ is N or $C-L^{42}-R^{83}$, $Z^{15}$ is N or $C-L^{43}-R^{84}$, $Z^{16}$ is N or $C-L^{44}-R^{85}$, $Z^{17}$ is N or $C-L^{45}-R^{86}$, at least one of $Z^{13}$ to $Z^{17}$ is N, $L^4$, $L^6$, and $L^{41}$ to $L^{45}$ are independently a single bond, a substituted or unsubstituted C6 to C20 arylene group, a substituted or unsubstituted C2 to C20 heterocyclic group, or a combination thereof, $R^i$, $R^j$, and $R^{82}$ to $R^{99}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^4$ and $R^s$ are independently a substituted or unsubstituted C6 to C30 aryl group, a substituted or unsubstituted C2 to C30 heterocyclic group, or a combination thereof, and $Ar^2$ is a substituted or unsubstituted C6 to C30 aryl group.

15. The composition as claimed in claim 1, wherein:

the first compound is represented by Chemical Formula I-1A-1 or I-1B-1:

[Chemical Formula I-1A-1]

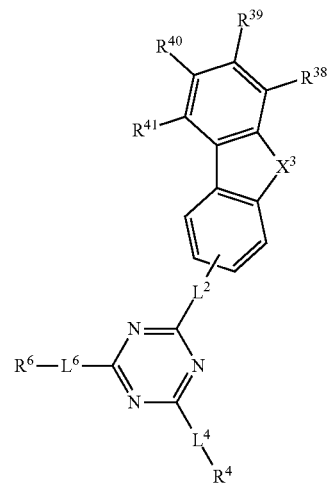

[Chemical Formula I-1B-1]

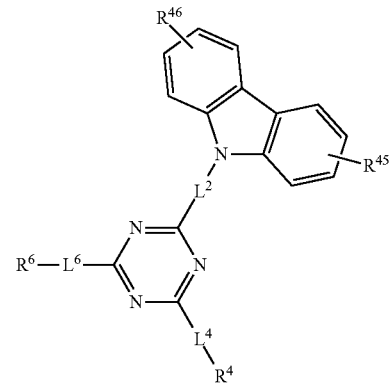

wherein, in Chemical Formulae I-1A-1 and I-1B-1, $X^3$ is O, S, or $NR^k$, $L^2$, $L^4$, and $L^6$ are independently a single bond or a substituted or unsubstituted phenylene group, $R^k$, $R^4$, and $R^6$ are independently a substituted or unsubstituted C6 to C30 aryl group, a substituted or unsubstituted C2 to C30 heterocyclic group, or a combination thereof, $R^{38}$ to $R^{41}$, $R^{45}$, and $R^{46}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

16. The composition as claimed in claim 1, further comprising a dopant.

17. The composition as claimed in claim 16, wherein the dopant is represented by Chemical Formula IV or Chemical Formula V:

[Chemical Formula IV]

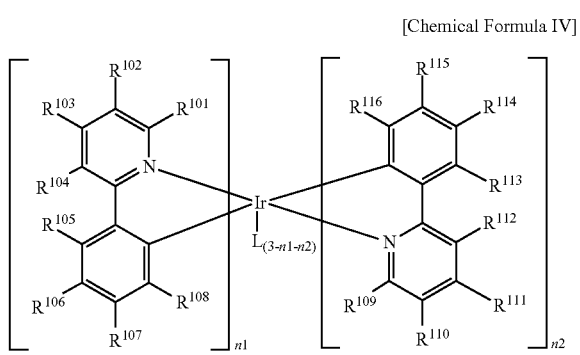

[Chemical Formula V]

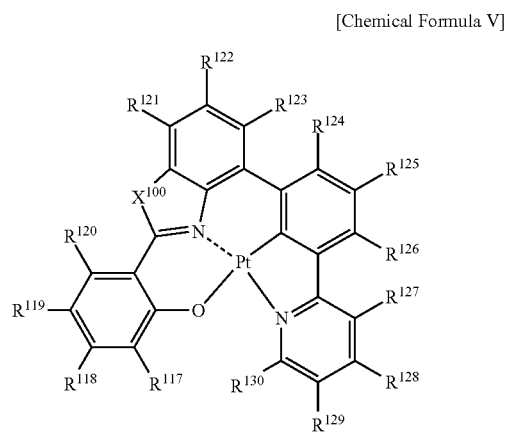

wherein, in Chemical Formula IV and Chemical Formula V, $X^{100}$ is selected from O, S, and $NR^{131}$, $R^{101}$ to $R^{131}$ are independently hydrogen, deuterium, a substituted or unsubstituted C1 to C10 alkyl group, a substituted or unsubstituted C6 to C20 aryl group, or $-SiR^{132}R^{133}R^{134}$, $R^{132}$ to $R^{134}$ are independently C1 to C6 alkyl group, at least one of $R^{101}$ to $R^{116}$ is a functional group represented by Chemical Formula IV-1, L is a bidentate ligand of a monovalent anion, which is a ligand that coordinates to iridium through a non-covalent electron pair of carbon or heteroatom, and n1 and n2 are independently an integer of 0 to 3, provided that n1+n2 is an integer of 1 to 3,

[Chemical Formula IV-1]

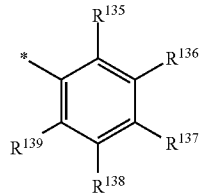

wherein, in Chemical Formula IV-1, $R^{135}$ to $R^{139}$ are independently hydrogen, deuterium, a substituted or unsubstituted C1 to C10 alkyl group, a substituted or unsubstituted C6 to C20 aryl group, or $-SiR^{132}R^{133}R^{134}$,

* indicates a linking point, and at least one of $R^{117}$ to $R^{131}$ is $-SiR^{132}R^{133}R^{134}$ or a tert-butyl group.

18. An organic optoelectronic device, comprising
an anode and a cathode facing each other, and
at least one organic layer between the anode and the cathode,
wherein the organic layer includes the composition as claimed in claim 1.

19. The organic optoelectronic device as claimed in claim 18, wherein:
the organic layer includes a light emitting layer, and
the light emitting layer includes the composition.

20. A display device comprising the organic optoelectronic device as claimed in claim 18.

21. A composition for an organic optoelectronic device, the composition comprising:
a first compound;
a second compound; and
a third compound,
wherein:
the first compound, the second compound, and the third compound are different from each other,
the first compound is represented by one of Chemical Formulae I-1A-1 to I-1A-6,
the second compound is represented by Chemical Formula II or Chemical Formula III, and
the third compound is represented by Chemical Formula II or Chemical Formula III:

[Chemical Formula I-1A-1]

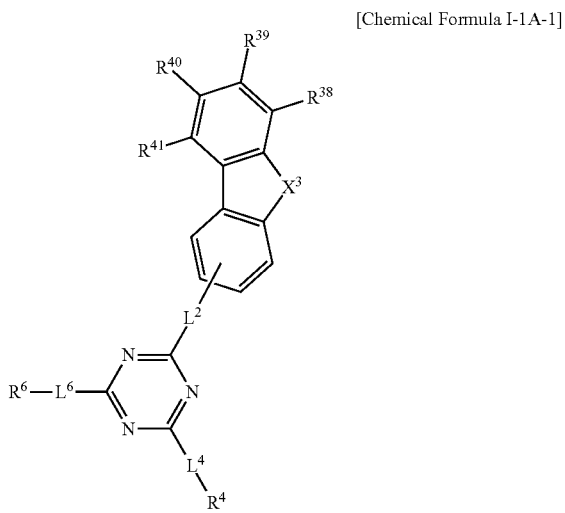

[Chemical Formula I-1A-2]

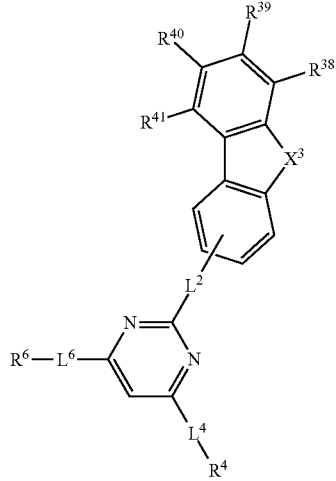

[Chemical Formula I-1A-3]

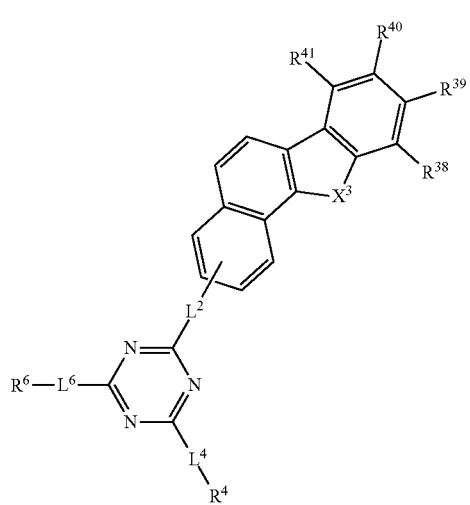

[Chemical Formula I-1A-4]

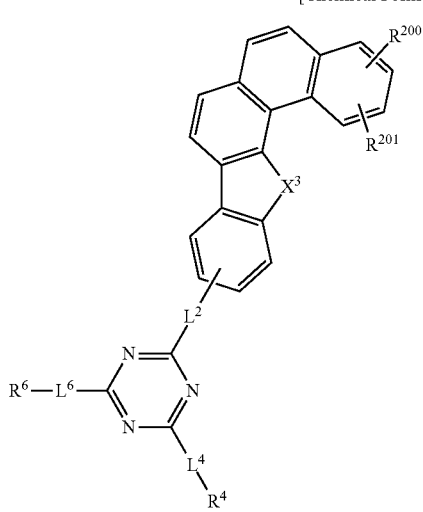

[Chemical Formula I-1A-5]

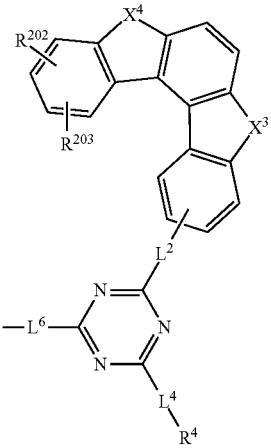

[Chemical Formula I-1A-6]

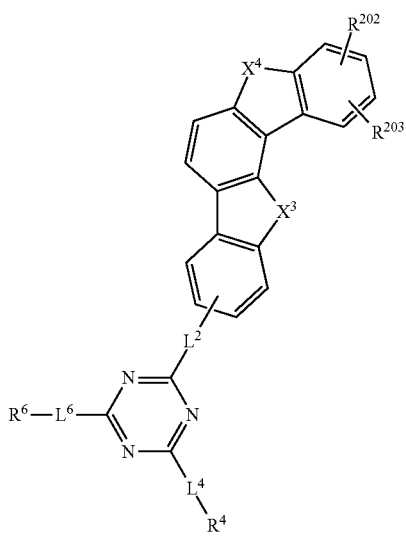

wherein, in Chemical Formulae I-1A-1 to I-1A-6, $X^3$ is O, S, or $NR^k$, $X^4$ is O, S, or $NR^l$, $L^2$, $L^4$, and $L^6$ are independently a single bond, a substituted or unsubstituted C6 to C20 arylene group, a substituted or unsubstituted C2 to C20 heterocyclic group, or a combination thereof, $R^k$, $R^l$, $R^4$, and $R^6$ are independently a substituted or unsubstituted C6 to C30 aryl group, a substituted or unsubstituted C2 to C30 heterocyclic group, or a combination thereof, $R^{38}$ to $R^{41}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{200}$ to $R^{203}$ are independently hydrogen, deuterium, a substituted or unsubstituted C1 to C10 alkyl group, a substituted or unsubstituted C6 to C20 aryl group, a halogen, a cyano group, or a combination thereof,

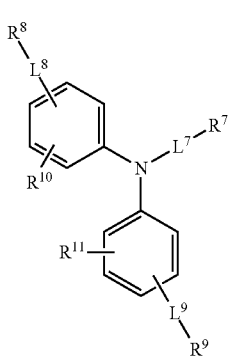
[Chemical Formula II]

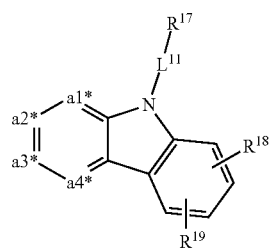
[Chemical Formula A-1]

wherein, in Chemical Formula II, $L^7$ to $L^9$ are independently a single bond, a substituted or unsubstituted C6 to C20 arylene group, a substituted or unsubstituted C2 to C20 heterocyclic group, or a combination thereof, $R^7$ to $R^{11}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^8$ to $R^{11}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring;

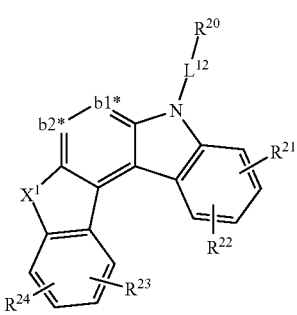
[Chemical Formula A-2]

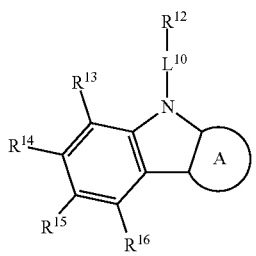
[Chemical Formula III]

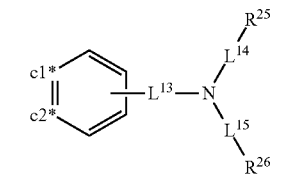
[Chemical Formula A-3]

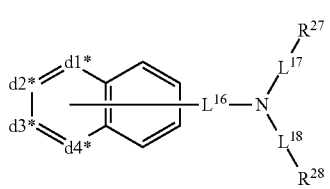
[Chemical Formula A-4]

wherein, in Chemical Formula III, $L^{10}$ is a single bond, a substituted or unsubstituted C6 to C20 arylene group, a substituted or unsubstituted C2 to C20 heterocyclic group, or a combination thereof, $R^{12}$ to $R^{16}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{12}$ to $R^{16}$ are separate or adjacent groups thereof are linked with each other to form a substituted or unsubstituted aromatic monocyclic or polycyclic ring, and A is a moiety represented by one of Chemical Formulae A-1 to A-7,

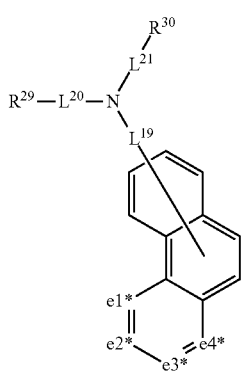
[Chemical Formula A-5]

-continued

[Chemical Formula A-6]

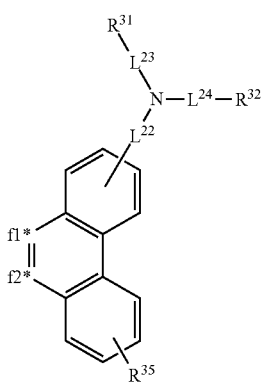

[Chemical Formula A-7]

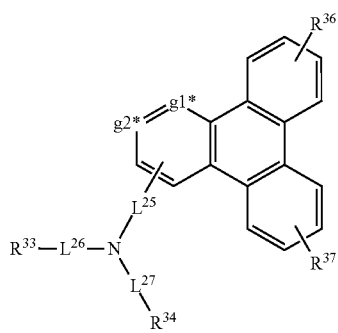

wherein, in Chemical Formulae A-1 to A-7,
X¹ is O, S, or NR$^a$,
a1* to a4* are independently a linking C or C-L$^a$-R$^b$,
adjacent two of a1* to a4* are the linking C and the remaining two are C-L$^a$-R$^b$,
d1* to d4* are independently a linking C or C-L$^b$-R$^c$,
adjacent two of d1* to d4* are the linking C and the remaining two are C-L$^b$-R$^c$,
e1* to e4* are independently a linking C or C-L$^c$-R$^d$,
adjacent two of e1* to e4* are the linking C and the remaining two are C-L$^c$-R$^d$,
b1* and b2*, c1* and c2*, f1* and f2*, and g1* and *g2 are each a linking C,
L$^a$, L$^b$, L$^c$, and L$^{11}$ to L$^{27}$ are independently a single bond, a substituted or unsubstituted C6 to C20 arylene group, a substituted or unsubstituted C2 to C20 heterocyclic group, or a combination thereof, and
R$^a$, R$^b$, R$^c$, R$^d$, and R$^{17}$ to R$^{37}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

22. An organic optoelectronic device, comprising:
an anode and a cathode facing each other, and
at least one organic layer between the anode and the cathode,
wherein the organic layer includes a green light emitting composition or a red light emitting composition, the composition including:
a first compound;
a second compound; and
a third compound,
wherein:
the first compound, the second compound, and the third compound are different from each other,
the first compound is represented by Chemical Formula I,
the second compound is represented by Chemical Formula II or Chemical Formula III, and
the third compound is represented by Chemical Formula II or Chemical Formula III:

[Chemical Formula I]

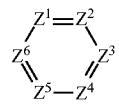

wherein, in Chemical Formula I,
Z¹ is N or C-L¹-R¹,
Z² is N or C-L²-R²,
Z³ is N or C-L³-R³,
Z⁴ is N or C-L⁴-R⁴,
Z⁵ is N or C-L⁵-R⁵,
Z⁶ is N or C-L⁶-R⁶,
only two or three of Z¹ to Z⁶ are N,
L¹ to L⁶ are independently a single bond, a substituted or unsubstituted C6 to C20 arylene group, a substituted or unsubstituted C2 to C20 heterocyclic group, or a combination thereof,
R¹ to R⁶ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof,
R¹ to R⁶ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, and
when R¹ to R⁶ are separate, at least one of R¹ to R⁶ is a substituted or unsubstituted C2 to C30 heterocyclic group;

[Chemical Formula II]

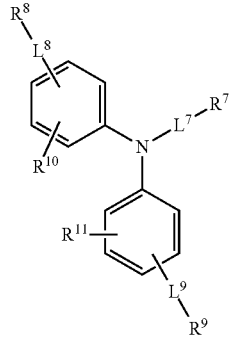

wherein, in Chemical Formula II,
L⁷ to L⁹ are independently a single bond, a substituted or unsubstituted C6 to C20 arylene group, a substituted or unsubstituted C2 to C20 heterocyclic group, or a combination thereof,
R⁷ to R¹¹ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and R$^8$ to R$^{11}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring;

[Chemical Formula III]

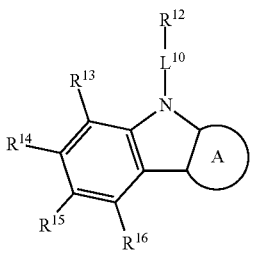

wherein, in Chemical Formula III,

L$^{10}$ is a single bond, a substituted or unsubstituted C6 to C20 arylene group, a substituted or unsubstituted C2 to C20 heterocyclic group, or a combination thereof, R$^{12}$ to R$^{16}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, R$^{12}$ to R$^{16}$ are separate or adjacent groups thereof are linked with each other to form a substituted or unsubstituted aromatic monocyclic or polycyclic ring, and A is a moiety represented by one of Chemical Formulae A-1 to A-7,

[Chemical Formula A-1]

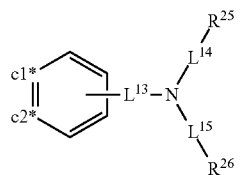

[Chemical Formula A-2]

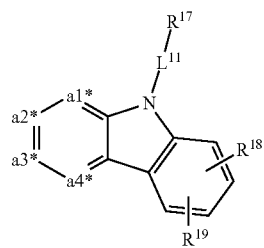

[Chemical Formula A-3]

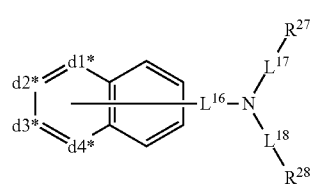

[Chemical Formula A-4]

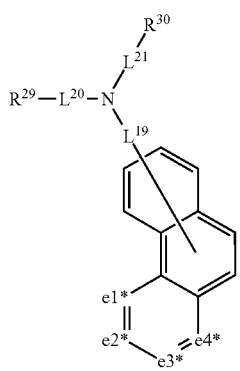

[Chemical Formula A-5]

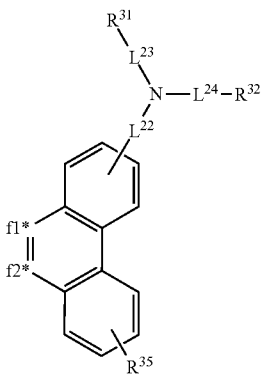

[Chemical Formula A-6]

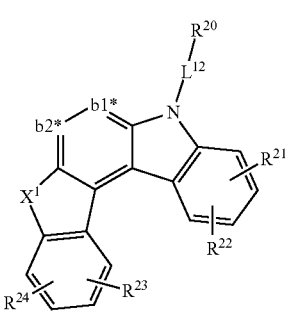

[Chemical Formula A-7]

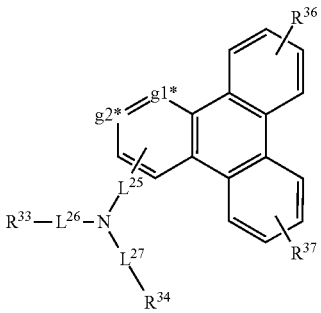

wherein, in Chemical Formulae A-1 to A-7,

X$^1$ is O, S, or NR$^a$, a1* to a4* are independently a linking C or C-L$^a$-R$^b$, adjacent two of a1* to a4* are the linking C and the remaining two are C-L$^a$-R$^b$, d1* to d4* are independently a linking C or C-L$^b$-R$^c$, adjacent two of d1* to d4* are the linking C and the remaining two are C-L$^b$-R$^c$, e1* to e4* are independently a linking C or C-$L^c$-$R^d$,
adjacent two of e1* to e4* are the linking C and the remaining two are C-$L^c$-$R^d$,
b1* and b2*, c1* and c2*, f1* and f2*, and g1* and *g2 are each a linking C,
$L^a$, $L^b$, $L^c$, and $L^{11}$ to $L^{27}$ are independently a single bond, a substituted or unsubstituted C6 to C20 arylene group, a substituted or unsubstituted C2 to C20 heterocyclic group, or a combination thereof, and
$R^a$, $R^b$, $R^c$, $R^d$, and $R^{17}$ to $R^{37}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

* * * * *